United States Patent
Saidara et al.

(10) Patent No.: US 7,399,277 B2
(45) Date of Patent: Jul. 15, 2008

(54) SYSTEM FOR MONITORING PHYSIOLOGICAL CHARACTERISTICS

(75) Inventors: Frank Saidara, Los Angeles, CA (US); John Joseph Mastrototaro, Los Angeles, CA (US); Charles Vallet Tolle, Van Nuys, CA (US); John C. Mueller, Jr., Simi Valley, CA (US); Jeff B. Sanders, Moorpark, CA (US); Edward S. Nielsen, Castaic, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 250 days.

(21) Appl. No.: 10/860,114

(22) Filed: Jun. 3, 2004

(65) Prior Publication Data

US 2005/0038332 A1 Feb. 17, 2005

Related U.S. Application Data

(63) Continuation-in-part of application No. 10/750,080, filed on Dec. 31, 2003, now abandoned, and a continuation-in-part of application No. 10/034,139, filed on Dec. 27, 2001, now Pat. No. 7,002,072.

(51) Int. Cl.
*A61B 5/00* (2006.01)
(52) U.S. Cl. ............... 600/300; 600/347; 600/365; 340/573.1
(58) Field of Classification Search .......... 600/346, 600/365
See application file for complete search history.

(56) References Cited

U.S. PATENT DOCUMENTS

| | | | |
|---|---|---|---|
| 3,701,345 A | 10/1972 | Heilman et al. | |
| 4,385,272 A | 5/1983 | Whitehead | |
| 4,498,479 A | 2/1985 | Martio et al. | |
| 4,510,346 A | 4/1985 | Bursh, Jr. et al. | |
| 4,562,751 A | 1/1986 | Nason et al. | |
| 4,573,994 A | 3/1986 | Fischell et al. | |
| 4,619,646 A | 10/1986 | Fernandez-Tresguerres Hernandez et al. | |
| 4,676,568 A | 6/1987 | Nault et al. | |
| 4,678,408 A | 7/1987 | Nason et al. | |
| 4,685,903 A | 8/1987 | Cable et al. | |
| 4,731,726 A | 3/1988 | Allen, III | |
| 4,747,824 A | 5/1988 | Spinello | |
| 4,760,730 A | 8/1988 | Frank et al. | |
| 4,857,857 A | 8/1989 | Valenti et al. | |
| 5,080,653 A | 1/1992 | Voss et al. | |
| 5,097,122 A | 3/1992 | Colman et al. | |
| 5,124,661 A | 6/1992 | Zelin et al. | |
| 5,219,099 A | 6/1993 | Spence et al. | |
| 5,233,986 A | 8/1993 | Robson | |
| 5,376,070 A | 12/1994 | Purvis et al. | |
| 5,390,671 A | 2/1995 | Lord et al. | |
| 5,391,250 A | 2/1995 | Cheney, II et al. | |
| 5,414,213 A | 5/1995 | Hillburn | |
| 5,482,473 A | 1/1996 | Lord et al. | |
| 5,523,534 A | 6/1996 | Meister et al. | |
| 5,557,210 A | 9/1996 | Cappa et al. | |
| 5,569,186 A | 10/1996 | Lord et al. | |
| 5,586,553 A | 12/1996 | Halili et al. | |
| 5,660,163 A | 8/1997 | Schulman et al. | |
| 5,665,065 A | 9/1997 | Colman et al. | |
| 5,683,270 A | 11/1997 | Warislohner | |
| 5,781,024 A | 7/1998 | Blomberg et al. | |
| 5,792,068 A | 8/1998 | Bowman et al. | |
| 5,822,715 A | 10/1998 | Worthington et al. | |
| 5,824,959 A | 10/1998 | Mista et al. | |
| 5,834,699 A | 11/1998 | Buck et al. | |
| 5,954,643 A | 9/1999 | VanAntwerp et al. | |
| 6,030,346 A | 2/2000 | Buck et al. | |
| 6,113,537 A | 9/2000 | Castano | |
| 6,117,083 A | 9/2000 | Buck et al. | |
| 6,155,267 A * | 12/2000 | Nelson | 128/899 |
| 6,175,752 B1 * | 1/2001 | Say et al. | 600/345 |
| 6,238,338 B1 * | 5/2001 | DeLuca et al. | 600/300 |
| 6,366,794 B1 * | 4/2002 | Moussy et al. | 600/345 |
| 6,551,276 B1 | 4/2003 | Mann et al. | |
| 6,558,351 B1 | 5/2003 | Steil et al. | |
| 2001/0011224 A1 | 8/2001 | Brown | |
| 2003/0100040 A1 | 5/2003 | Bonnecaze et al. | |
| 2003/0125612 A1 | 7/2003 | Fox et al. | |
| 2003/0187336 A1 | 10/2003 | Odagiri et al. | |
| 2003/0208113 A1 | 11/2003 | Mault et al. | |
| 2005/0203360 A1 * | 9/2005 | Brauker et al. | 600/345 |

FOREIGN PATENT DOCUMENTS

| | | |
|---|---|---|
| DE | 101 08 862 A1 | 2/2001 |
| EP | 1 102 194 | 5/2001 |

(Continued)

*Primary Examiner*—Robert L. Nasser, Jr.
*Assistant Examiner*—Patricia Mallari
(74) *Attorney, Agent, or Firm*—Gates & Cooper LLP

(57) ABSTRACT

Apparatuses and methods for medical monitoring physiological characteristic values such as blood glucose levels for the treatment of diabetes, are presented. The apparatuses and methods provide for preventing any negative consequence in the operation of a monitor and/or infusion device as a result of disorientation that may occur from waking from slumber with a low blood glucose level. In addition, a graphical display is disclosed incorporating a variety of enhancements which readily conveys to the user historical as well as real time information regarding the measured characteristic value.

27 Claims, 29 Drawing Sheets

FOREIGN PATENT DOCUMENTS

| | | |
|---|---|---|
| EP | 1 127 544 | 8/2001 |
| WO | WO 96/25088 | 8/1996 |
| WO | WO 96/35370 | 11/1996 |
| WO | WO 98/56078 | 12/1998 |
| WO | WO 98/56293 | 12/1998 |
| WO | WO 00/18449 | 4/2000 |
| WO | WO 00/19887 | 4/2000 |
| WO | WO 02/44865 | 6/2002 |
| WO | WO 2004/008956 | 1/2004 |
| WO | WO 2004/009161 | 1/2004 |

* cited by examiner

NOTES
1. Appears only if the Sensor Feature is on.
2. Appears only if the Bolus Wizard is enabled and the Sensor Feature is on.
3. Appears only when High Glucose Limit and Sensor Feature is enabled.
4. Appears only when Low Glucose Limit and Sensor Feature is enabled.
5. Appears only when a new sensor has been connected.
6. Appears only when an old sensor has been reconnected.
7. When this screen times out it returns to the idle screen. Pressing any key on the idle returns you to this screen.

| Name | Default Value | Limit | Warning | Step Size | Max Entries |
|---|---|---|---|---|---|
| Sensor On/Off | Off | N/A | N/A | N/A | 1 |
| High Glucose | 200 mg/dL | Low Glucose +10 mg/dL to 400 mg/dL Max range is 60 mg/dL to 400 mg/dL. | N/A | 1 mg/dL | 1 |
| High Snooze | 1:00 | 0:05 - 3:00 | N/A | 0:05 | 1 |
| Low Glucose | 50 mg/dL | Shutoff Limit +10 mg/dL to High Glucose -10 mg/dL. Max range is 50 mg/dL to 390 mg/dL. | N/A | 1 mg/dL | 1 |
| Low Snooze | 0:20 | 0:05 - 1:00 | N/A | 0:05 | 1 |
| Shutoff Limit | 40 mg/dL | 40 mg/dL to Low Glucose -10 mg/dL. Max range is 40 mg/dL to 120 mg/dL. | N/A | 1 mg/dL | 1 |
| Alarm Snooze | 0:05 | 0:05 - 1:00 | N/A | 0:05 | 1 |
| Cal Reminder | 1:00 | 0:05 - 4:00 | N/A | 0:05 | 1 |
| Missed Data | 0:20 | 0:05 - 0:40 | N/A | 0:05 | 1 |

FIG. 9D

SYSTEM FOR MONITORING PHYSIOLOGICAL CHARACTERISTICS

CROSS-REFERENCE TO RELATED APPLICATIONS

This continuation-in-part application claims priority under 35 U.S.C. §120 from U.S. patent application Ser. No. 10/034,139, filed Dec. 27, 2001, now U.S. Pat. No. 7,022,072 and entitled "SYSTEM FOR MONITORING PHYSIOLOGICAL CHARACTERISTICS," and U.S. patent application Ser. No. 10/750,080, filed Dec. 31, 2003, now abandoned and entitled "SYSTEM FOR MONITORING PHYSIOLOGICAL CHARACTERISTICS," which are both incorporated herein by reference.

BACKGROUND OF THE INVENTION

1. Field of the Invention

This invention relates generally to medical monitoring systems. More specifically, this invention relates to methods and systems for monitoring physiological characteristics in individuals including those associated with physiological conditions (e.g. monitoring blood glucose levels in diabetics).

2. Description of the Related Art

A variety of electrochemical sensors have been developed for detecting and/or quantifying specific agents or compositions in a patient's blood. Notably, glucose sensors have been developed for use in obtaining an indication of blood glucose levels in a diabetic patient. Such readings are useful in monitoring and/or adjusting a treatment program which typically includes the regular administration of insulin to the patient. Periodic blood glucose readings significantly improve medical therapies using semi-automated medication infusion devices. Some exemplary external infusion devices are described in U.S. Pat. Nos. 4,562,751, 4,678,408 and 4,685,903, while some examples of automated implantable medication infusion devices are described in U.S. Pat. No. 4,573,994, all of which are herein incorporated by reference.

Electrochemical sensors can be used to obtain periodic measurements over an extended period of time. Such sensors can include a plurality of exposed electrodes at one end for subcutaneous placement in contact with a user's interstitial fluid, blood, or the like. A corresponding plurality of conductive contacts can be exposed at another end for convenient external electrical connection with a suitable monitoring device through a wire or cable. Exemplary sensors are described in U.S. Pat. Nos. 5,299,571; 5,390,671; 5,391,250; 5,482,473; and 5,586,553, which are all incorporated by reference herein.

Conventional glucose monitoring systems are somewhat limited in features that they provide to facilitate the monitoring of blood glucose levels. Typically, a glucose monitor can take readings as directed by the user and might provide a warning if a reading is deemed at an unsafe level (e.g., a hyper- or hypoglycemic condition). However, by the time the warning occurs, the user may already be experiencing negative symptoms. Furthermore, it may be unacceptable to address this by simply reducing (or raising) the value which triggers an indicator (e.g. a display, an alarm or the like) of an unsafe condition, because this may prompt a user to take "remedial" action (such as administering an additional bolus) when no unsafe condition would have actually materialized. Such an approach merely increases the occurrence of false positive alarms. As a consequence, the unnecessary "remedial" action can actually provoke an unsafe condition. As described above, although existing glucose monitors adequately detect blood glucose levels upon entering the hyperglycemic (or hypoglycemic) range, they do not anticipate these conditions.

As is known in the art, a glucose crash occurs when blood glucose levels of an individual are in a state of rapid decline and its symptoms are similar to those associated with hypoglycemia. The symptoms are caused by the dynamics of a declining glucose level and not by an absolute glucose level. Specific symptoms can include a feeling of light headedness, sweating, tremors, nervousness and/or disorientation. Disorientation is a particular risk to the patient. If the patient becomes disoriented while operating machinery, the patient could harm himself or others. A glucose crash can be caused by any of the following events: excess insulin administration; an unexpected increase in insulin sensitivity; a fall of free fatty acids in the blood; heavy exercise; or mental or physical stress. As previously mentioned, ordinary glucose monitors provide only for detection of hypoglycemic and hyperglycemic levels.

Impaired fasting glucose (IFG) is another condition which is not predicted by conventional glucose monitors. The American Diabetes Association (ADA) identifies IFG as an undesirable glucose condition, defined as a 126 mg/dL or higher blood glucose level at wakeup. Repeated IFG events can contribute to diabetic morbidity. One cause of IFG is an inadequate nocturnal insulin basal infusion rate. Although a patient can deal with the IFG after waking by administering an insulin bolus, it is preferable for the patient to avoid IFG incidents entirely.

Conventional monitors are designed to alert the user of unsafe conditions; however, many other factors and situations are also important to the user in managing treatment. For example, events such as meals or exercise, as well as entering calibration values are not tied to reminders issued by conventional monitors. Typical monitors provide only a single alarm to call attention to the user. This can be problematic in contexts of varying physiological states because a user is not made aware of the specific condition and/or the appropriate degree of urgency. In conventional alarm systems, until the user investigates, there is often no indication of the reason for the alarm or the severity of the situation.

Furthermore, the alarm settings and features for many monitoring systems are very limited. Such systems can provide duplicative warnings that can frustrate users and become ignored if they are excessive. In addition, typical monitoring systems can alarm during predictable periods during which a user does not wish to be disturbed.

Thus, conventional glucose monitoring systems are somewhat limited in features they provide to facilitate the monitoring of blood glucose levels. There is a need for monitoring systems for a physiological characteristic (such as blood glucose levels) with convenient features and settings that allow users flexibility in tailoring the system's operation to their personal needs and lifestyle. Particularly, there is a need for such systems that provide advanced alarm functions to reduce or eliminate redundant alarms. In addition, there is a need for monitoring systems that allow a convenient review of measurement and alarm histories. These and other needs are met by the present invention.

SUMMARY OF THE INVENTION

The invention as embodied and disclosed herein pertains to apparatuses and methods for monitoring physiological characteristics such as blood glucose levels. Embodiments of the invention include dynamic monitoring functions that can perform predictive analyses to anticipate harmful conditions, such as hyperglycemic (or hyperglycemic) incidents, before they occur. These dynamic functions can be used to monitor normal physiological functions, as well as in a variety of other contexts including the optimization of athletic performance. Other embodiments of the invention include advanced alarm and reminder functions, as well as advanced data display presentation tools. Embodiments of the invention disclosed herein facilitate the convenient and efficient management of diseases such as diabetes.

One embodiment of the invention includes a method of monitoring a physiological characteristic of a user using a device including an input element capable of receiving a signal from a sensor that is based on a sensed physiological characteristic value of the user, and a processor for analyzing the received signal. In typical embodiments of the invention, the processor determines a dynamic behavior of the physiological characteristic value and provides an observable indicator based upon the dynamic behavior of the physiological characteristic value so determined. In a preferred embodiment, the physiological characteristic value is a measure of the concentration of blood glucose in the user. In another embodiment, the process of analyzing the received signal and determining a dynamic behavior includes repeatedly measuring the physiological characteristic value to obtain a series of physiological characteristic values to determine how the physiological characteristic is changing over time.

Embodiments of the invention include devices which display data from measurements of a sensed physiological characteristic (e.g. blood glucose concentrations) in a manner and format tailored to allow a user of the device to easily monitor and, if necessary, modulate the physiological status of that characteristic (e.g. modulation of blood glucose concentrations via insulin administration). An illustrative embodiment of the invention is a device comprising a sensor input capable of receiving a signal from a sensor, the signal being based on a sensed physiological characteristic value of a user; a memory for storing a plurality of measurements of the sensed physiological characteristic value of the user from the received signal from the sensor; and a display for presenting a text and/or graphical representation of the plurality of measurements of the sensed physiological characteristic value (e.g. text, a line graph or the like, a bar graph or the like, a grid pattern or the like or a combination thereof). Preferably, the graphical representation displays real time measurements of the sensed physiological characteristic value. Such devices can be used in a variety of contexts, for example in combination with other medical apparati. In preferred embodiments of the invention, the device is used in combination with at least one other medical device (e.g. a glucose sensor). An illustrative system consists of a glucose sensor, a transmitter and pump receiver and a glucose meter. In this system, radio signals from the transmitter can be sent to the pump receiver every 5 minutes to provide providing real-time sensor glucose (SG) values. Values/graphs are displayed on a monitor of the pump receiver so that a user can self monitor blood glucose and deliver insulin using their own insulin pump. Typically an embodiment of device disclosed herein communicates with a second medical device via a wired or wireless connection. Wireless communication can include for example the reception of emitted radiation signals as occurs with the transmission of signals via RF telemetry, infrared transmissions, optical transmission, sonic and ultrasonic transmissions and the like. Most preferably, the device is an integral part of a medication infusion pump (e.g. an insulin pump). Typically in such devices, the physiological characteristic values includes a plurality of measurements of blood glucose.

In typical embodiments of the invention, the physiological characteristic value measurement is displayed in a graphical format, a text format or a combination thereof. In an illustrative example, the graphical representation can comprise a color coded set of one or more indicators of the status of the physiological characteristic. In a specific embodiment, the graphical representation comprises one or more trend indicators, indicating an approximate rate trend in the sensed physiological characteristic value over a recent series of the plurality of measurements (e.g. the four most recent measurements of the sensed physiological characteristic value). Optionally the graphical representation further comprises a vertical cursor which allows a user to alternatively select measurements of a sensed physiological characteristic value from the graphical format or from a text format. For example, the display can include a scrolling vertical cursor, allowing individual Blood Glucose measurements in the graphics plot to be selected, with the Blood Glucose value and the time the measurement was made displayed in a text portion of the screen.

Embodiments of the invention include devices designed to adapt to a number of situations in which a user may exhibit different behaviors shortly after being awakened as compared to when they are completely awake. For example, in a situation where the characteristic value is a blood glucose level, it has been observed that when a user of the monitor is awakened from sleep by low blood glucose alarm from the monitor, there is often a period of disorientation. The disorientation may be particularly significant because the effect of low blood glucose level is made more severe at night. In this context, another illustrative embodiment of the invention is a device comprising a sensor input capable of receiving a signal from a sensor, the signal being based on a sensed physiological characteristic value of a user of the device; and a processor coupled to the sensor input for operating an alarm based on the received signal from the sensor, wherein the processor activates the alarm according to a first criteria when the user is awake; and a second criteria when the user is asleep.

A typical example of this embodiment is a device comprising a sensor input capable of receiving a signal from a sensor, the signal being based on a sensed physiological characteristic. In preferred embodiments of the invention, the sensed physiological characteristic is a measurement of glucose and the device provides an alarm warning at an earlier timepoint when the user is asleep as compared to when the user is awake by altering a threshold criteria for the activation an alarm during sleeping hours. Alternatively one can provide an alarm having a different tone or audibility. Exemplary threshold criteria include glucose concentrations reaching a predetermined value; or glucose concentrations exhibiting a predetermined rate of change. Optionally one can provide earlier or different alarm warnings to the user by using multiple alarms. For example the device can activate the alarm to provide earlier alarm warning by monitoring a rate of change in the sensed physiological characteristic value and adjusting an alarm threshold value when the rate exceeds a predetermined rate limit.

A related embodiment of the invention is a device comprising a sensor input capable of receiving a signal from a sensor, the signal being based on a sensed physiological characteristic value of a user; and a processor coupled to the sensor input for operating an alarm based on the sensed physiological characteristic value of the user from the received signal from the sensor; wherein the processor activates the alarm and delays accepting input from the user when the alarm awakens the user. In a specific embodiment of the invention, the physiological characteristic value is a blood glucose measurement and delaying accepting input from the user is applied to a low blood glucose alarm or a high blood glucose alarm. In preferred embodiments of the invention, the processor delays accepting input from the user until the user provides a predetermined input such as entering a numeric code or executing a button sequence. Optionally, delaying accepting input from a user who is most likely asleep when the alarm sounds is set according to a schedule based on a time of day, or alternatively, is set by the user before sleeping.

Yet another embodiment of the invention is a device comprising a sensor input capable of receiving at least one signal from a sensor, the signal being based on a plurality of sensed physiological characteristic values of a user of the device; and a processor coupled to the sensor input for operating a plurality of alarms based on the received signal from the sensor; wherein the processor is capable of activating each of the plurality of alarms according to a mathematical analysis of the relationship between the plurality of sensed physiological characteristic values. Preferably, the plurality of sensed physiological characteristic values include the blood glucose concentrations in the user; and the rate of change of blood glucose concentrations in the user over a predetermined time period. In such devices, a first alarm can be activated when glucose concentrations exhibit a predetermined rate of change and a second alarm can be activated when glucose concentrations reach a predetermined value. Optionally the criteria for activating the first alarm are more stringent than the criteria for activating the second alarm. In a preferred embodiment of the invention, the processor is capable of activating an alarm based on an evaluation of both the blood glucose concentrations in the user and the rate of change of blood glucose concentrations and the alarm is activated based on a mathematical comparison of the blood glucose concentrations in the user and the rate of change of blood glucose concentrations in the user. In an exemplary embodiment, the alarm is activated when the relationship between the blood glucose concentrations in the user and the rate of change of blood glucose concentrations in the user meet a certain criteria. Optionally such criteria are determined by one or more mathematical formulae or algorithms that are based upon calculations that consider the specific the relationship between the blood glucose concentrations in the user and the rate of change of blood glucose concentrations in situations typically considered dangerous to the user. Optionally this device further includes a relay that automatically dials a predetermined telephone number as part of a notification scheme for an event that has not been acknowledged and/or addressed by the user.

In some embodiments of the invention, each of the series of physiological characteristic values includes a smoothing filtered group of repeated physiological characteristic value readings. In such embodiments, a slope of a line fit to the series of physiological characteristic values can be calculated if a most recent of the series of physiological characteristic values is within a qualifying range. In some embodiments of the invention, the physiological characteristic value readings may be decreasing and the slope is negative. Typically, the indicator can also include a warning alarm that is responsive to the dynamic behavior profile of the physiological characteristic value. The warning alarm can also announce an anticipated glucose crash or merely low glucose levels, depending on the operating parameters of the particular dynamic analysis, including comparison of the slope to a threshold rate (e.g., 1% to 3% per minute) and comparison of the current measured value to a qualifying range (e.g., 60 to 150 mg/dL). In typical embodiments, the series of values analyzed is taken from a defined span of time (e.g., ten to thirty minutes).

In other typical embodiments of the invention, an anticipated physiological characteristic value is determined from an extrapolated curve based upon the series of physiological characteristic values. In such embodiments the indicator can provide a warning of an anticipated morning glucose incident. In preferred embodiments, the series of values analyzed can also be taken from a defined span of time (e.g. one hour). In one embodiment, the extrapolated curve is determined from a slope of a line fit to the series of physiological characteristic values and an average of the series of physiological characteristic values. In another illustrative embodiment, the anticipated physiological characteristic value can be determined approximately three hours before an anticipated wakeup time. In addition, in certain embodiments, the indicator can be provided if the anticipated value is outside a qualifying range (e.g., approximately 60 mg/dL to 126 mg/dL).

In related embodiments of the invention, a slope of a line fit to the series of physiological characteristic values is calculated if a most recent of the series of physiological characteristic values exceeds a threshold value and the slope is positive. In such embodiments, the indicator can provide a warning of an anticipated hyperglycemic incident. In an illustrative embodiment, the series of physiological characteristic values spans a time period of approximately thirty minutes and the indicator can be provided if the slope is steeper than a threshold rate. In this context a typical threshold rate can be approximately 3% per minute and the threshold value can be approximately 180 mg/dL. In such other embodiments, the indicator can provide a warning of an anticipated hypoglycemic incident. In an illustrative embodiment, the series of physiological characteristic values spans a time period of approximately thirty minutes and the indicator can be provided if the slope is steeper than a threshold rate. In this context a typical threshold rate can be approximately 3% per minute and the threshold value can be approximately 70 mg/dL.

Another embodiment of the invention includes a physiological characteristic monitor (and corresponding methods for its use) including an input device capable of receiving a signal from a sensor and a processor capable of analyzing the received signal and providing multiple alarms, each of which can be based upon different conditions associated with the physiological characteristic value of the user. In preferred embodiments, the signal is based on a physiological characteristic value of a user. In some embodiments, the multiple alarms are distinguishable from each other and can include any one of a wide variety of signals such as audible signals, visual signals, tactile signals, displays, and/or the like.

In some embodiments of the invention, the processor determines a physiological characteristic value from the received signal and the multiple alarms are based upon that value. In such embodiments, each of the multiple alarms can then be triggered if the physiological characteristic value exceeds an associated threshold value.

In other embodiments of the invention, one of a first pair of the multiple alarms can be triggered when a narrow range of physiological characteristic values is exceeded. The first pair of the multiple alarms is typically associated with a first upper threshold value and a first lower threshold value, respectively. In further embodiments, a second pair of multiple alarms can be triggered by a wider range of physiological characteristic values (e.g. exceeding a predetermined value). The second pair of the multiple alarms can be associated with a second upper threshold value and a second lower threshold value, respectively.

In yet another embodiment of the invention, a physiological characteristic monitoring method and device are disclosed which include an input device capable of receiving a signal from a sensor and a processor for analyzing the received signal. Typically, the signal is based on a physiological characteristic value of a user. In preferred embodiments, the processor initiates a timer based upon a condition associated with the physiological characteristic value of the user and provides a reminder to the user following expiration of the timer. In some embodiments of the invention, the reminder can include an alarm signal selected from the group consisting of an audible signal, a visual signal, a tactile signal, a display, and/or the like. Typically, the duration of the timer is preset based upon the specific initiating condition.

In preferred embodiments of the invention, conditions which trigger the one or more alarms can vary. For example, the conditions which trigger the one or more alarms can be an event marker such as meal markers, exercise markers, high blood glucose markers and low blood glucose markers. The condition(s) which trigger the one or more alarms can further be a reference value that is entered into the monitor and the reminder can indicate that a new reference value should be entered.

In other embodiments of the invention, the processor can determine a physiological characteristic value from the received signal and the triggering condition is then based upon that physiological characteristic value. For example, the triggering condition can be situations where the physiological characteristic value exceeds a predetermined threshold value.

Other embodiments of the invention include a physiological characteristic monitor including an input device capable of receiving a signal from a sensor, a processor for analyzing the received signal and determining physiological characteristic value data of the user from the received signal, a memory for storing the physiological characteristic value data of the user and a display. Typically, the signal is based on a physiological characteristic value of a user. In preferred embodiments, the display provides a retrospective display of the physiological characteristic value data. In some embodiments of the invention, the stored physiological characteristic value data includes a minimum and maximum blood glucose value and the retrospective display shows the minimum and maximum blood glucose value with a respective time and date. In other embodiments, the stored physiological characteristic value data can include a first number of excursions above an upper blood glucose value and a second number of excursions below a lower blood glucose value and the retrospective display shows the first and second number.

In other embodiments of the invention, the stored physiological characteristic value data can include a distribution of blood glucose values and the retrospective display shows a first portion of the blood glucose values above an upper blood glucose value, a second portion of the blood glucose values below a lower blood glucose value and a third portion of the blood glucose values between the upper value and the lower value. In preferred embodiments, the portions can be shown as percentages, times or numbers of readings. The display can include a total time for the physiological characteristic value data as well as the total number of readings for the physiological characteristic value data. In preferred embodiments of the invention, the first portion and the second portion can be shown as integrated values. The integrated values can be based on the sums of magnitude differences from the upper blood glucose value and the lower blood glucose value for the first and second portion, respectively. In such embodiments, the integrated values can be divided by a respective duration of sensor use.

In yet other embodiments of the invention, further advanced alarm functions are employed such as an alarm repeat delay to prevent redundant alarms for a specified period and an alarm snooze function to prevent alarms generally for a specified period. In addition, embodiments of the invention include a monitor that performs a status check routine based on sensor activity, sensor calibration and telemetry. Other embodiments of the invention include a measurement entry time and value display for a monitor as well as a real-time and historical measurement display function.

BRIEF DESCRIPTION OF THE DRAWINGS

Referring now to the drawings in which like reference numbers represent corresponding parts throughout.

Figure 8A:
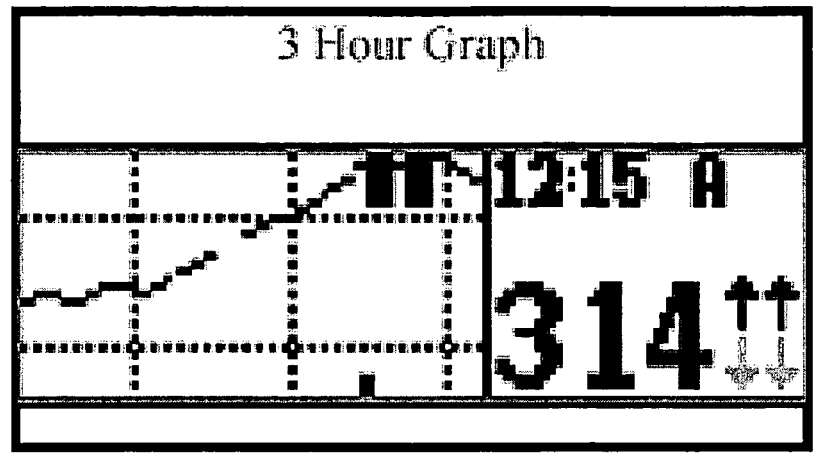
FIG. 8A illustrates a screen employing a graphical display of measurements of a physiological characteristic value with a three hour time scale.
Figure 8B:
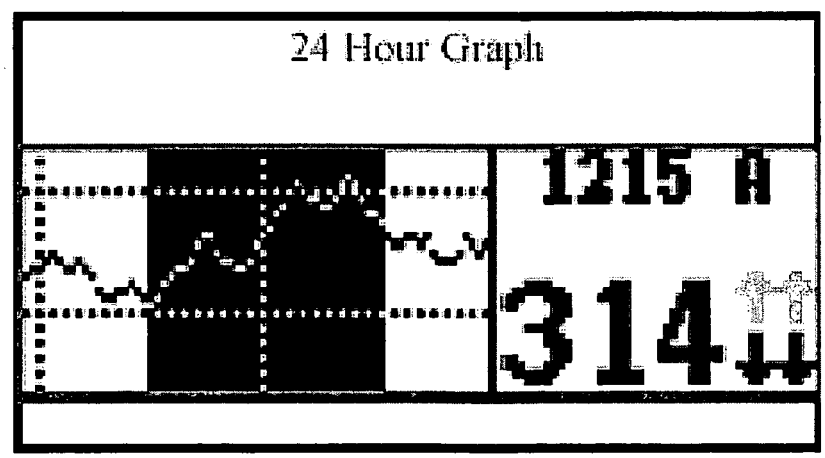
FIG. 8B illustrates a screen employing a graphical display of measurements of a physiological characteristic value with a twenty-four hour time scale.
Figure 8C:
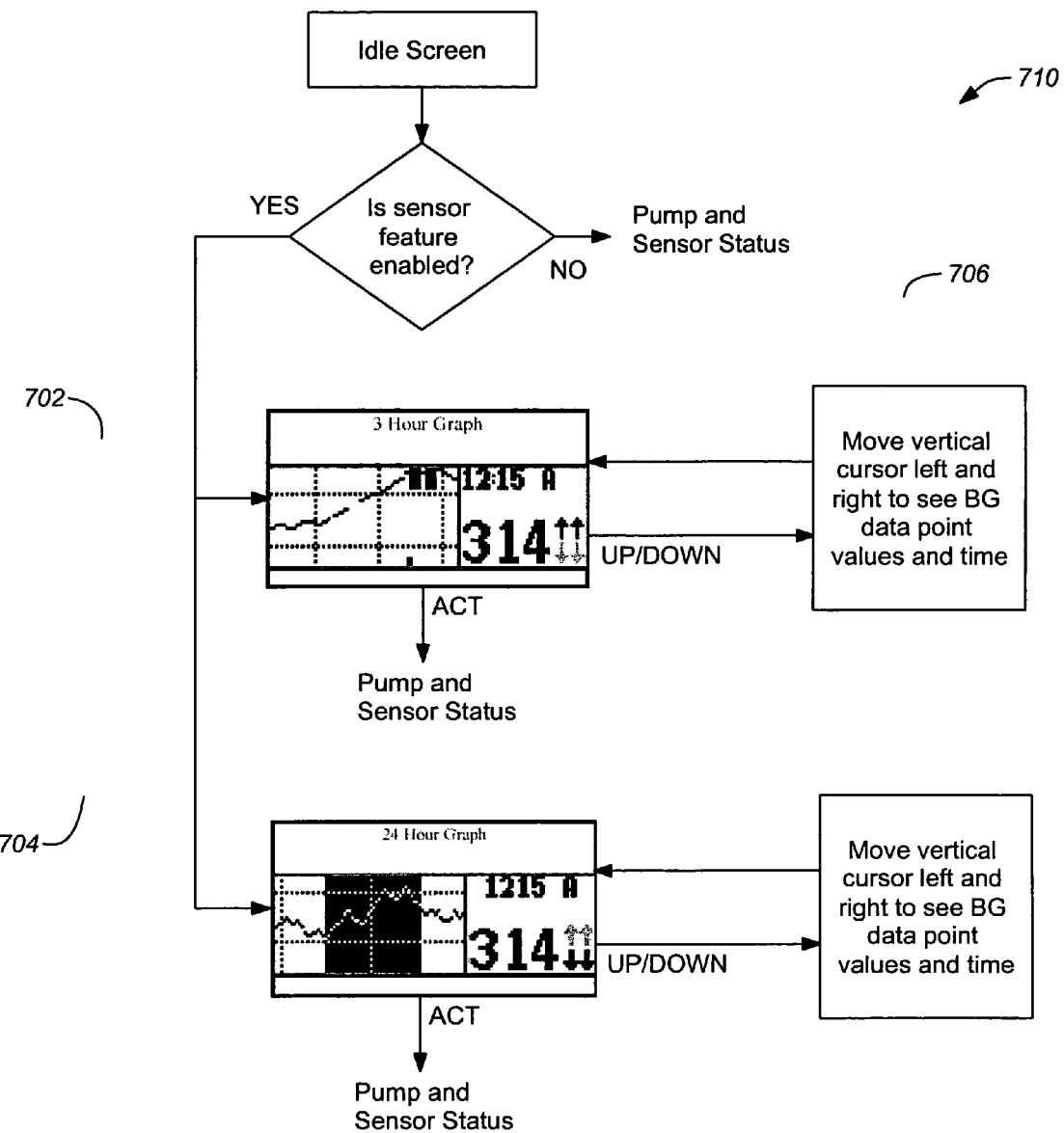
FIG. 8C illustrates control of the graphical display of measurements of a physiological characteristic value.
Figure 8D:
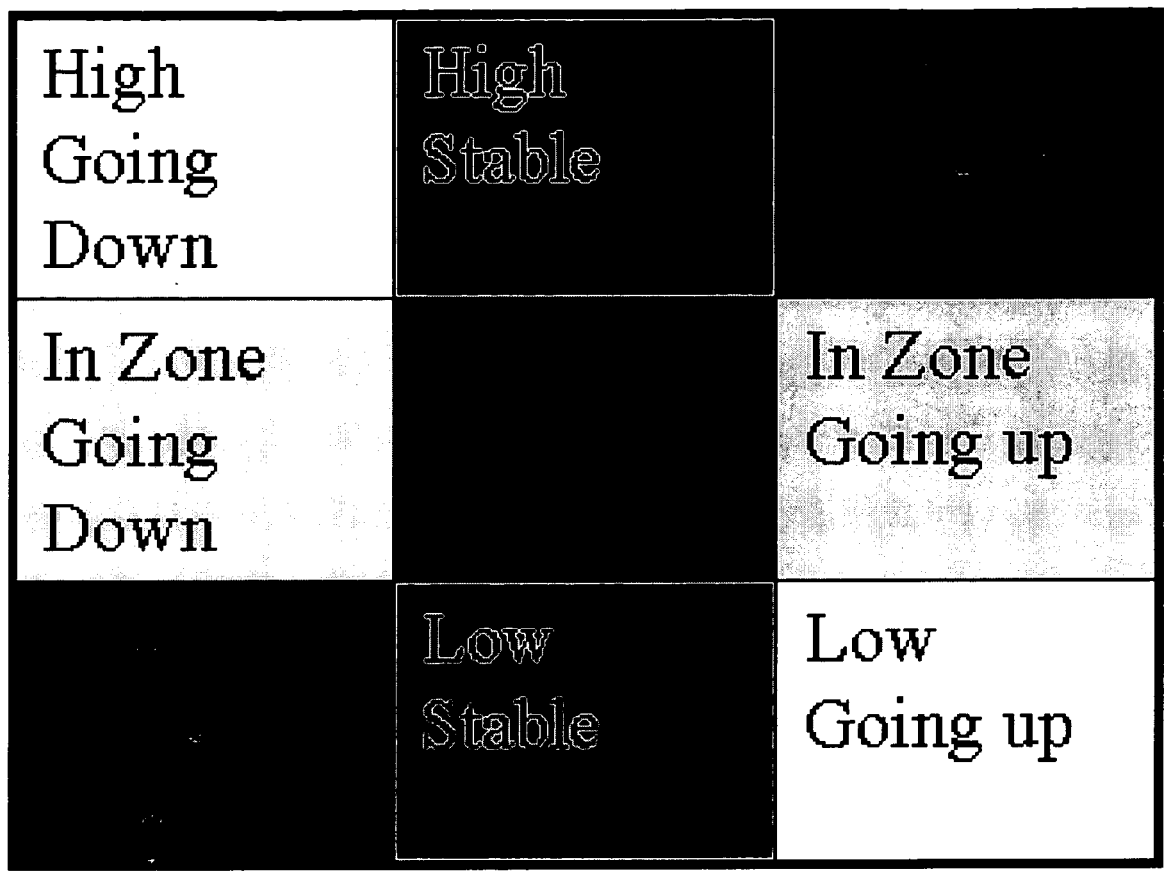
FIG. 8D illustrates a screen employing a graphical display of measurements of a physiological characteristic value in a grid display pattern which is further color coded to clearly delineate data which includes both physiological characteristic levels as well as physiological characteristic trends (e.g.
Figure 8E:
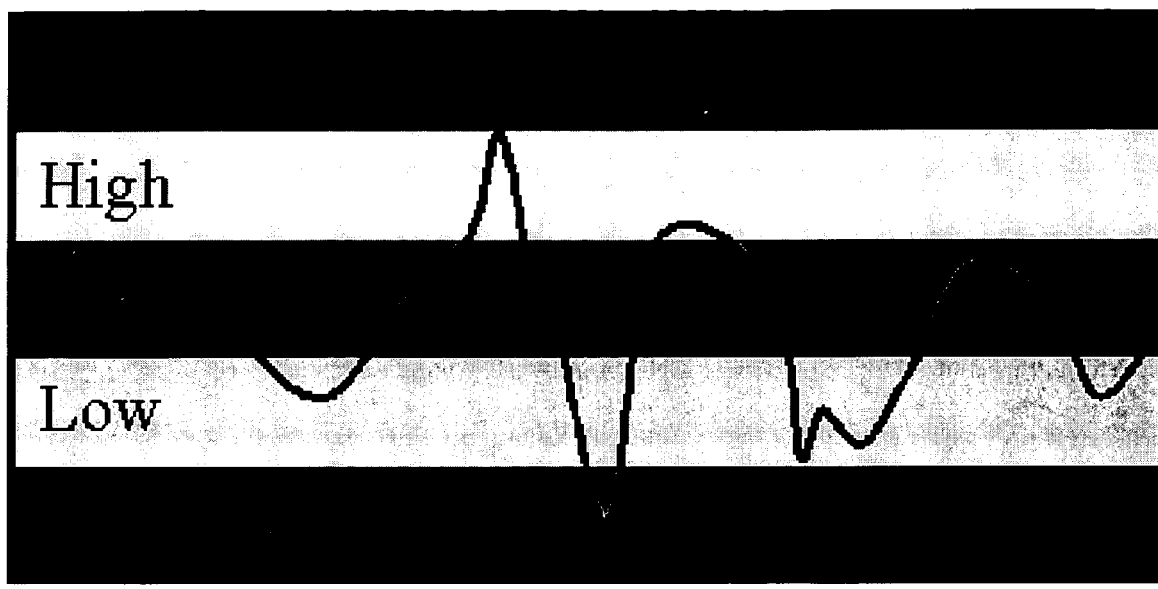
Figure 9A:
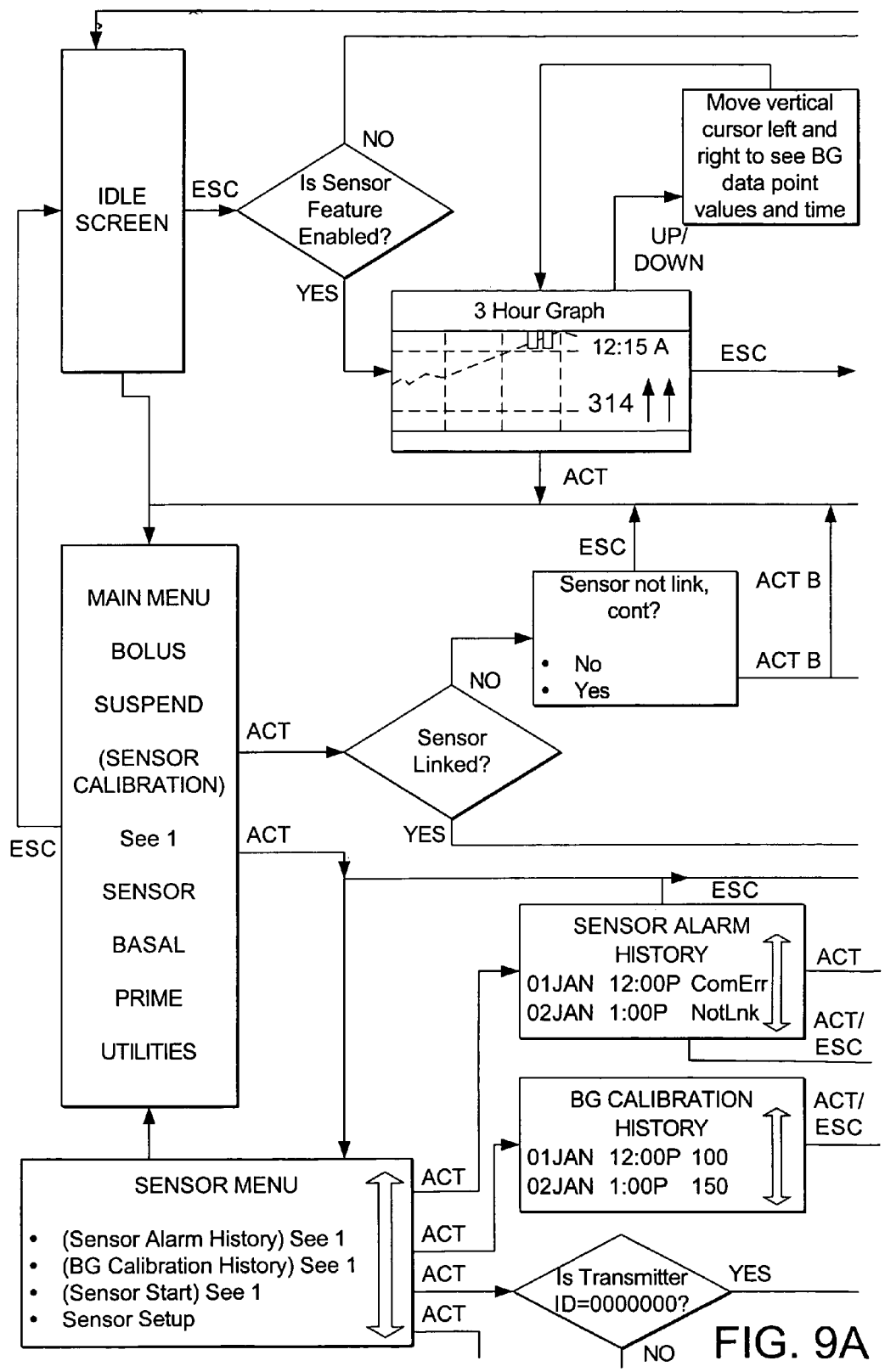
Figure 9B:
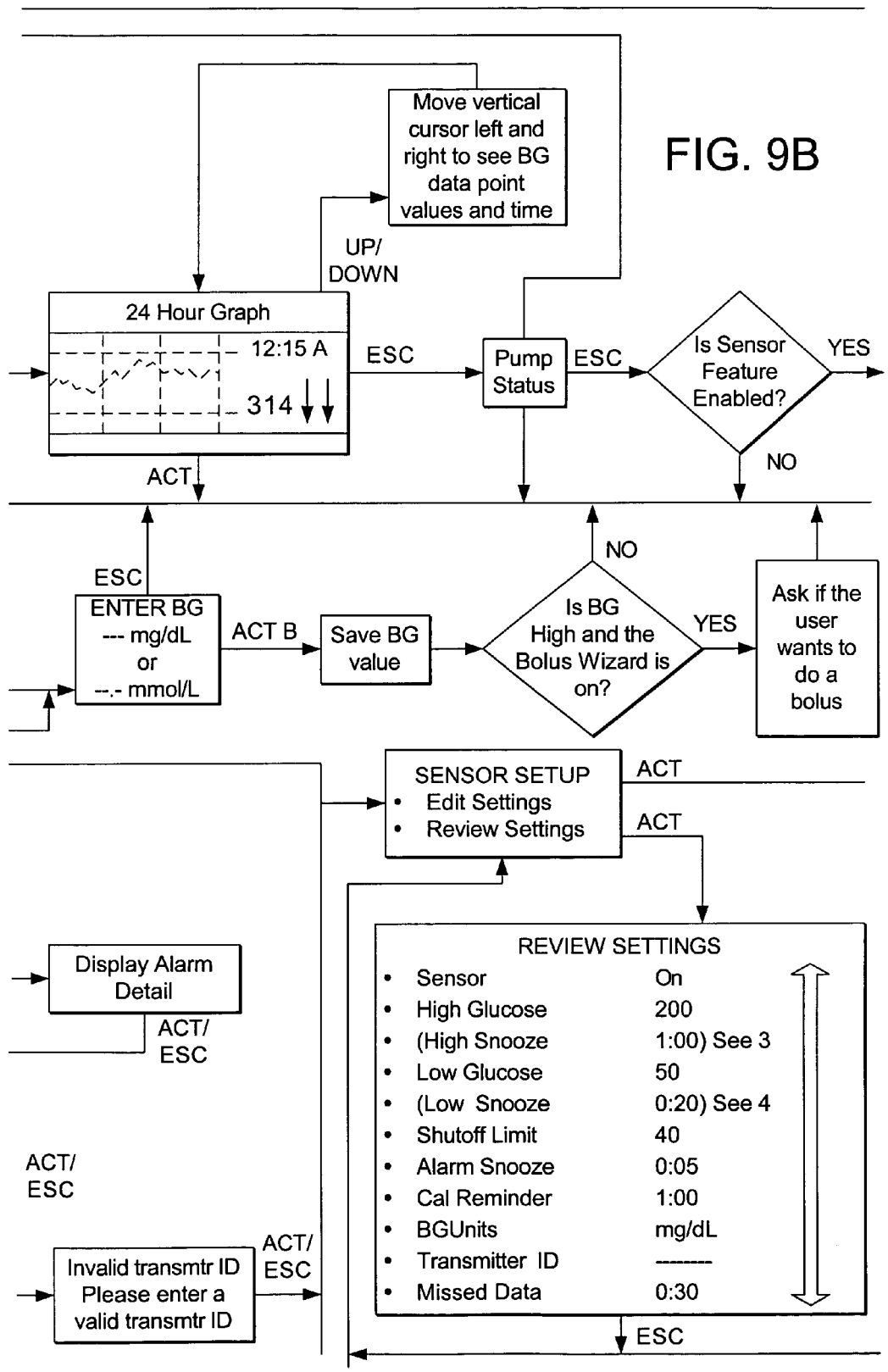
Figure 9C:
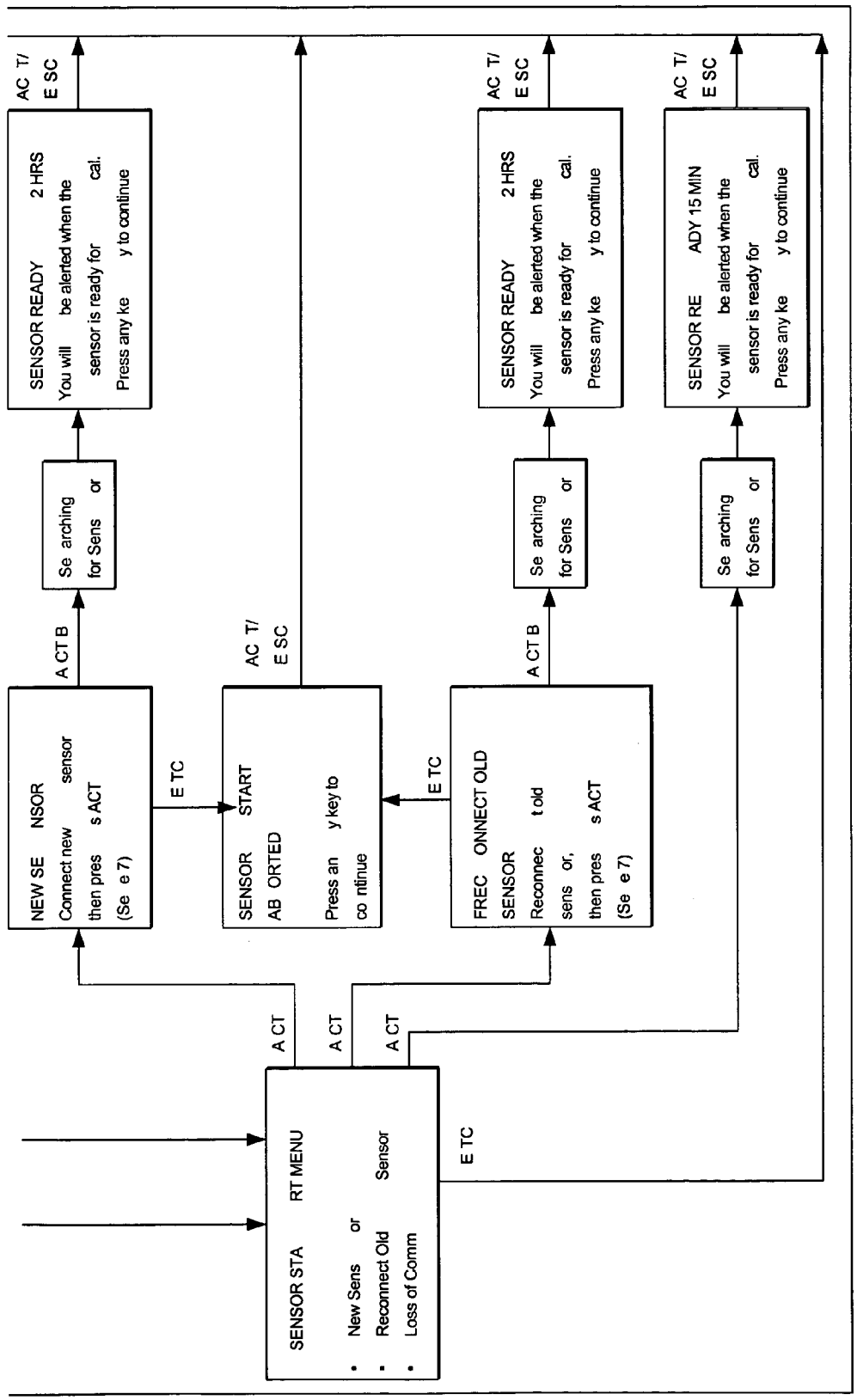
Figure 9E:
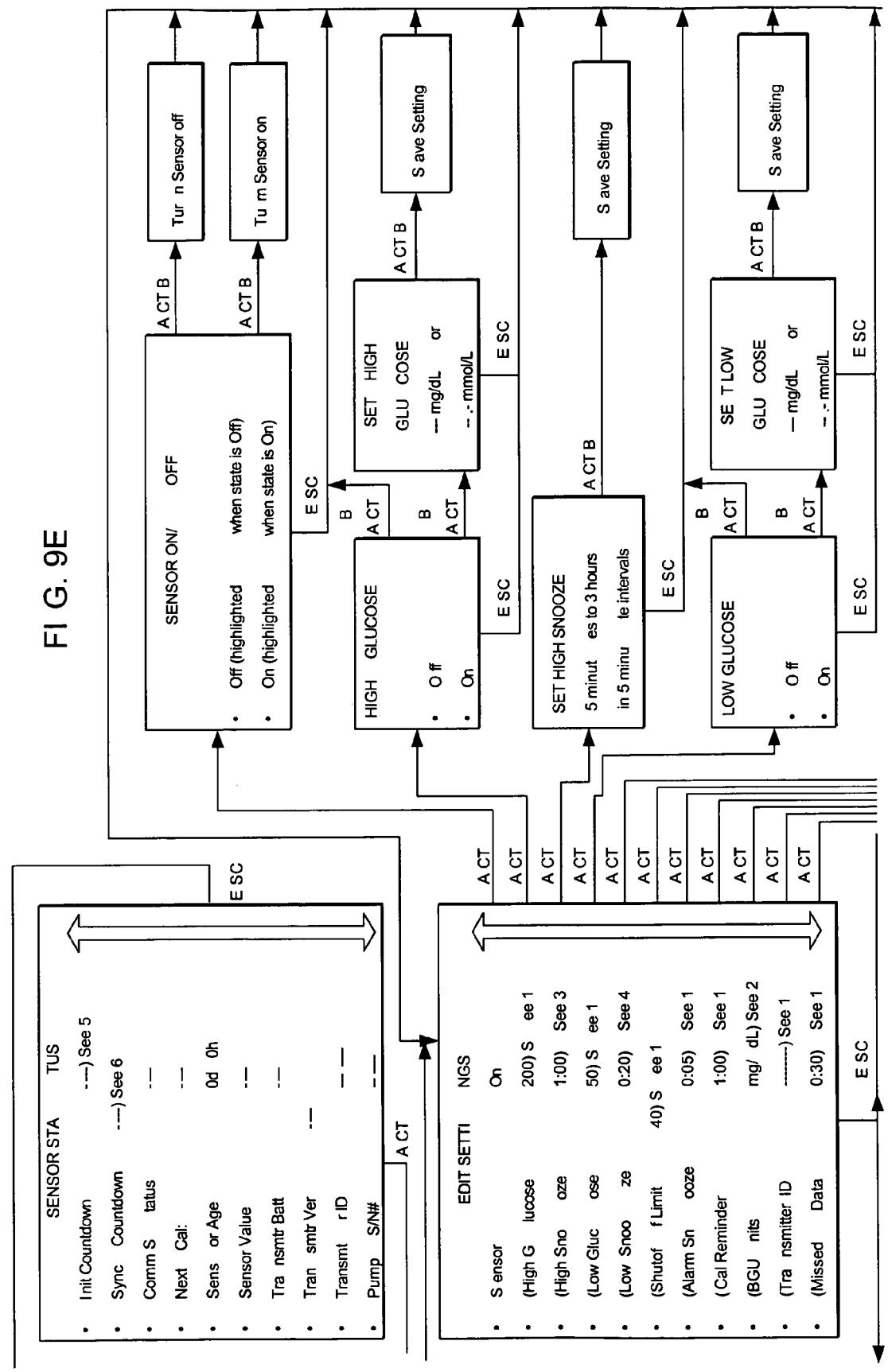
Figure 9F:
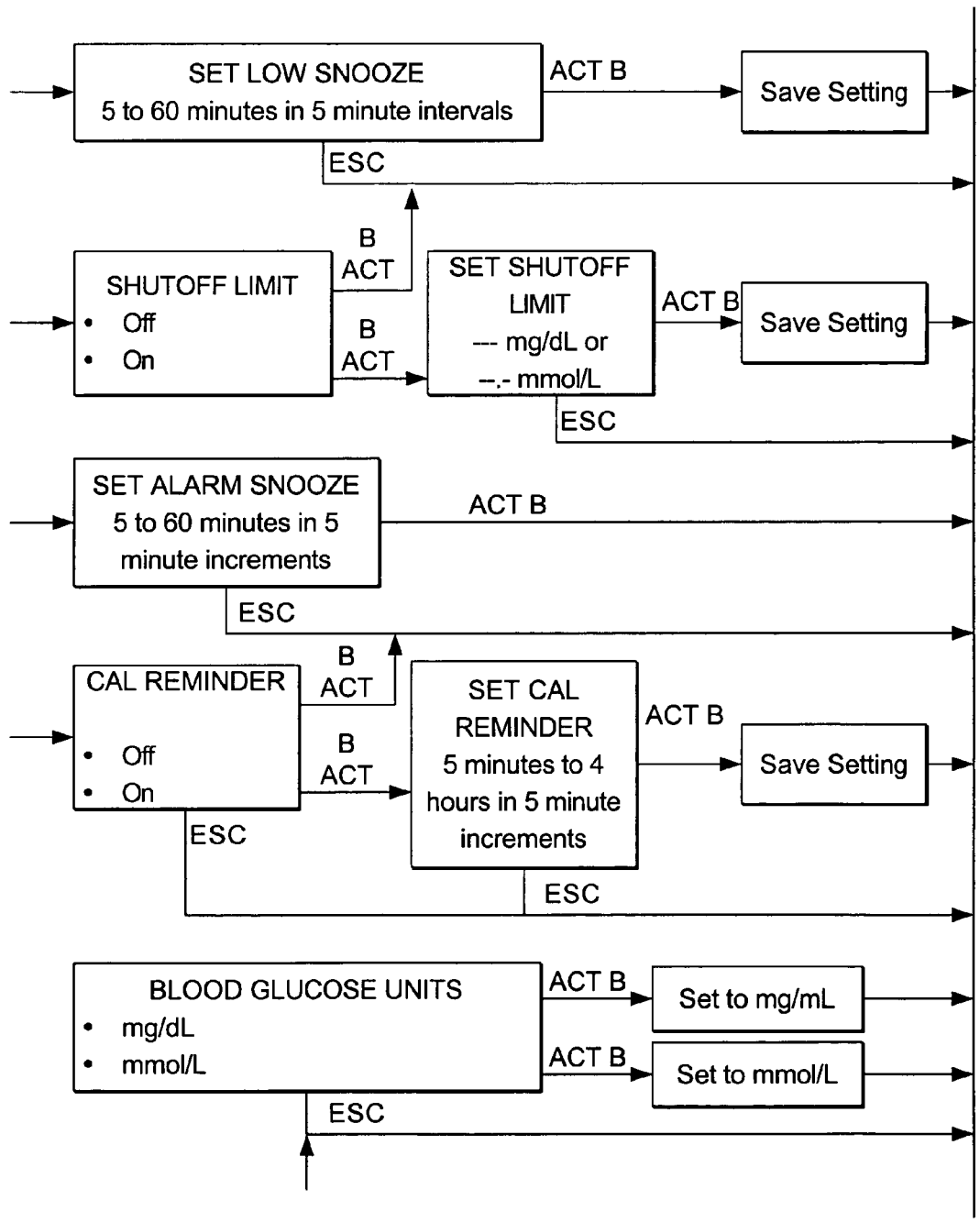
Figure 9G:
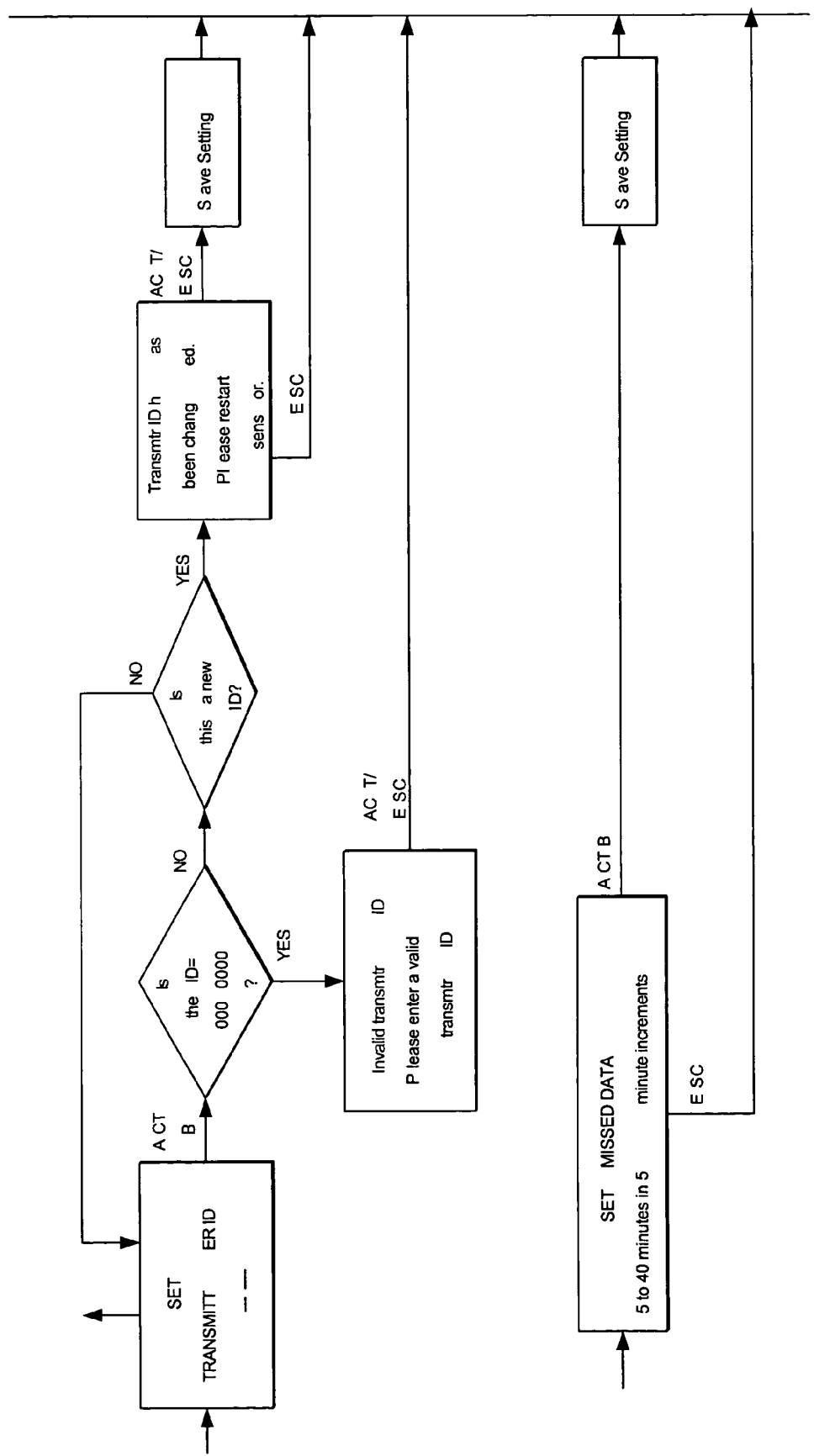

high and going down, high and stable, high and going up, in zone going down, in zone in zone stable, in zone going up etc.);

FIG. 8E illustrates a screen employing a graphical display of which provides the concentrations of a physiological characteristic over a specific time scale as well as information regarding the physiological significance of that concentration (e.g. too high, in zone, too low etc.) where the information regarding the physiological significance of that concentration is delineated in a row-like display pattern. Alternative embodiments of this type of display pattern include a gradual transition between the stripes of the row-like display pattern as well as embodiments where stripe colors (e.g. yellow and red) can vary over time and represent warning levels that are preselected (e.g. set by the user);

FIGS. 9A-9G provide a flow chart which illustrates various aspects of a system for monitoring physiological characteristics in individuals including the manner in which various interrelated elements of the system can be designed to interact.

DETAILED DESCRIPTION OF THE PREFERRED EMBODIMENT

1. Overview

Embodiments of the present invention encompass methods and systems for the convenient operation of monitoring physiological characteristics ("characteristic monitoring systems"). The description provided here encompasses the architecture of the apparatus as well as its control and convenience features. The control and convenience features of the present invention can be implemented in a wide range of detailed characteristic monitoring system designs. Although embodiments of the present invention are primarily described in the context of glucose monitors used in the treatment of diabetes, the embodiments of the invention are applicable to a wide variety of patient treatment programs where a physiological characteristic is periodically monitored to use in estimating the responsive treatment. For example, embodiments of the invention can be used to determine the status and/or levels of a variety of characteristics including those associated with agents such as hormones, cholesterol, medication concentrations, pH, oxygen saturation, viral loads (e.g., HIV), or the like. As is known in the art, a sensor for the characteristic monitor can be implanted in and/or through subcutaneous, dermal, sub-dermal, inter-peritoneal or peritoneal tissue. Such sensors typically communicate a signal from the sensor set to the characteristic monitor.

Embodiments of the invention include specific features associated with a physiological characteristic monitoring apparatus (e.g. a continuous glucose monitor, glucose test strip meters and the like) that are designed to facilitate a users monitoring and/or control of a physiological characteristic of interest (e.g. blood glucose concentrations). Typically such physiological characteristic monitoring devices are coupled to one or more complementary medical apparati (e.g. sensor sets, infusion pumps and the like). In preferred embodiments, the sensor set and monitor are for determining glucose levels in the blood and/or body fluids of the user without the use of, or necessity of, a wire or cable connection between the transmitter and the monitor. Physiological characteristic monitors of the invention can be incorporated in to a wide variety of medical systems known in the art such as with infusion pump systems that designed to control the rate that medication is infused into the body of a user. Such infusion pump systems can include a physiological characteristic monitor which provides information to a user that facilitates the user's subsequent use of a drug delivery system (e.g. one that calculates a dose to be delivered by a medication infusion pump). In such contexts, the meter associated with the physiological characteristic monitor may also transmit commands to, and be used to remotely control, the delivery system. Preferably, the physiological characteristic monitor is used to monitor the glucose concentration in the body of the user, and the therapeutic agent that is infused by the delivery system into the body of the user includes insulin. Illustrative systems are disclosed for example in U.S. Pat. Nos. 6,558,351 and 6,551,276; PCT Application Nos. US99/21703 and US99/22993; as well as WO 2004/008956 and WO 2004/009161, all of which are incorporated herein by reference.

The physiological characteristic monitoring apparatus can be used in combination with a wide variety of other devices, for example in a closed loop infusion system designed to control the rate that medication is infused into the body of a user. Such a closed loop infusion system can include a sensor and an associated meter which generates an input to a controller which in turn operates a delivery system (e.g. one that calculates a dose to be delivered by a medication infusion pump). In such contexts, the meter associated with the sensor may also transmit commands to, and be used to remotely control, the delivery system. Such systems can be fully automated with the sensor transmitting information to a processor that determines whether a medication dose is needed, with such processors further being coupled to an infusion pump which then infuses the appropriate medication. Alternatively, the systems can be partially automated, for example where a processor makes a recommendation to the user, with the user's approval then activating the infusion pump. Illustrative systems are disclosed for example in U.S. Pat. Nos. 6,558,351 and 6,551,276; PCT Application Nos. US99/21703 and US99/22993; as well as WO 2004/008956 and WO 2004/009161, all of which are incorporated herein by reference.

Embodiments of the characteristic monitor system of the invention are primarily adapted for use in subcutaneous human tissue. Alternatively, embodiments of the invention can be placed in a variety of other types of physiological milieus, such as muscle, lymph, organ tissue, veins, arteries or the like, as well as being used in related environments such as animal tissue. Embodiments of the invention can provide sensor readings on an intermittent, near-continuous or continuous basis.

Embodiments of the invention include sensing and advanced predictive functions of the monitor which are designed to anticipate unsafe conditions for a user before they occur. In addition, predictive functions can be employed so that a user can obtain feedback to obtain a desired physical objective, such as maximizing athletic performance. Other functions of the monitor include multiple programmable alarms and reminders and diagnostic functions. Advanced alarm functions also include an alarm repeat delay function and a snooze function that can be set by a user. Embodiments of the invention can include advanced display tools to facilitate easy and quick interpretation of information related to the user's condition, including a display function for an alarm history as well as a history of measurements.

2. Glucose Monitor

Figure 1A:
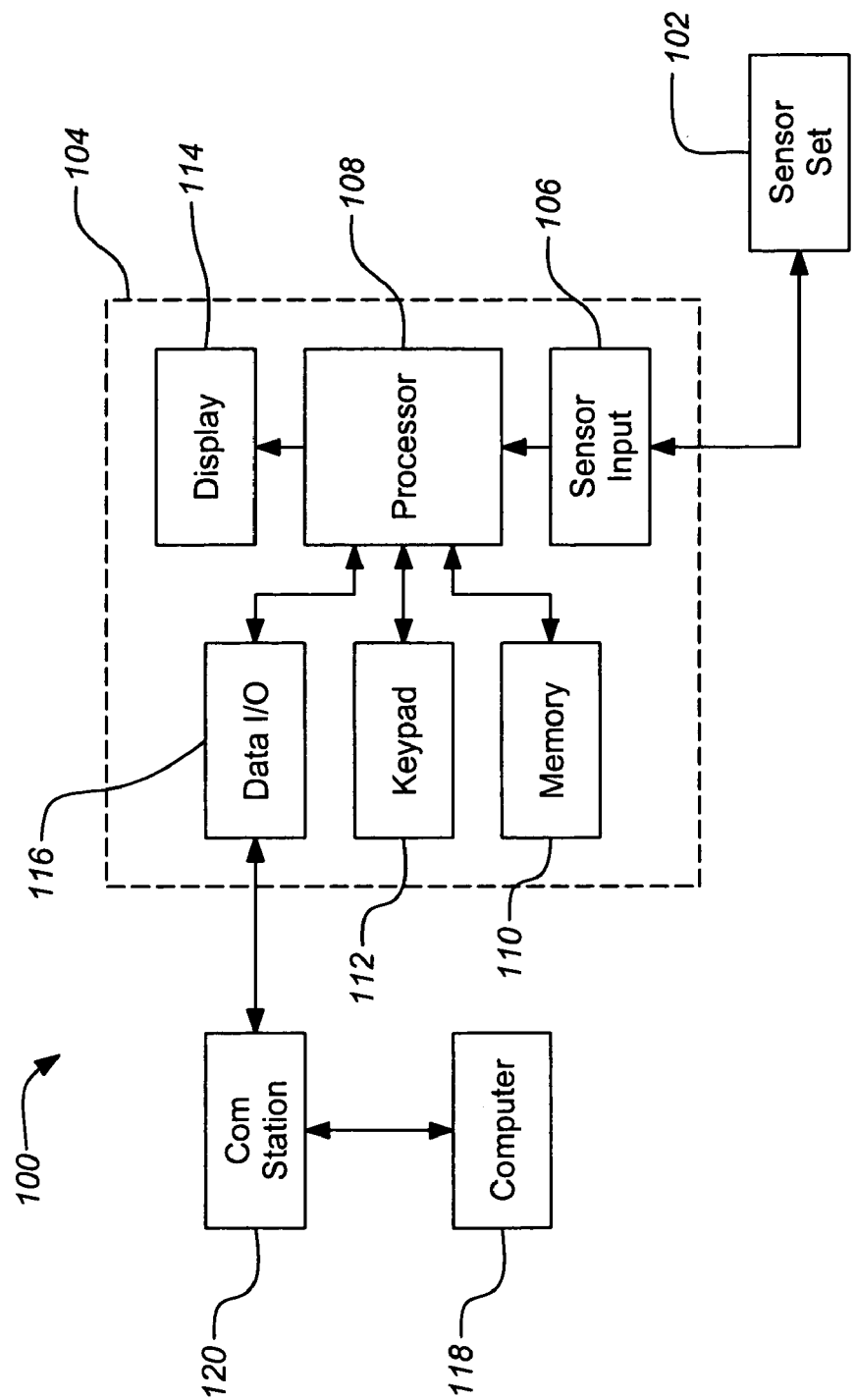
FIG. 1A is a block diagram of a characteristic monitor embodiment of the present invention.

FIG. 1A is a block diagram of a characteristic monitoring system 100 in accordance with an embodiment of the present invention. The characteristic monitoring system 100 generally includes a sensor set 102 that employs a sensor that produces a signal that corresponds to a measured characteristic of the user, such as a blood glucose level. The sensor set 102 communicates these signals to a characteristic monitor 104 that is designed to interpret these signals to produce a characteristic reading or value for the user, i.e. a measurement of the characteristic. The sensor signals enter the monitor 104 through a sensor input 106 and through the sensor input 106 the signals are conveyed to a processor 108. The processor 108 determines and manipulates the sensor readings within the monitor 104. In addition, but not limited to, the characteristic monitor 104 provides additional functions that will aid in the treatment regime to which the characteristic reading applies. For example, but not limited to, the monitor may track meals, exercise and other activities which affect the treatment of diabetes. These additional functions can be combined with or independent from the characteristic readings determined by the monitor 104. Monitors of the invention have a number of embodiments and can for example be coupled to an infusion pump that can further provide a medication to a user. Optionally the monitor is designed to be inconspicuous, for example a monitor design that resembles a wristwatch.

Other components of the monitor 104 support the processor 108 in performing functions. A memory 110 is used to store data and instructions used by the processor 108. A data entry device 112 such as a keypad is used to receive direct input from the user and a display 114 such as a liquid crystal display (LCD), or the like, is used to relate information to the user. In addition, the monitor 104 includes a data port 116, such as a digital input/output (I/O) port.

The data port 116 can be used for the monitor 104 to communicate with a computer 118. To facilitate communication, the monitor 104 may interface with the computer 118 through a communication station 120 that can serve as a docking station for the monitor 104, for example. In some embodiments, the data port 116 within the monitor 104 can be directly connected to the computer 118. Through the communication link, data may be downloaded from the monitor 104, such as stored characteristic readings, settings, programs and other information related to the monitor's function. Thus, advanced analysis can be performed on the computer 118, freeing memory 110 within the monitor 104. Data such as characteristic readings, settings and programs can also be downloaded to the monitor 104. In this way, the monitor 104 can be conveniently reprogrammed without requiring tedious manual entry by the user.

Figure 1B:
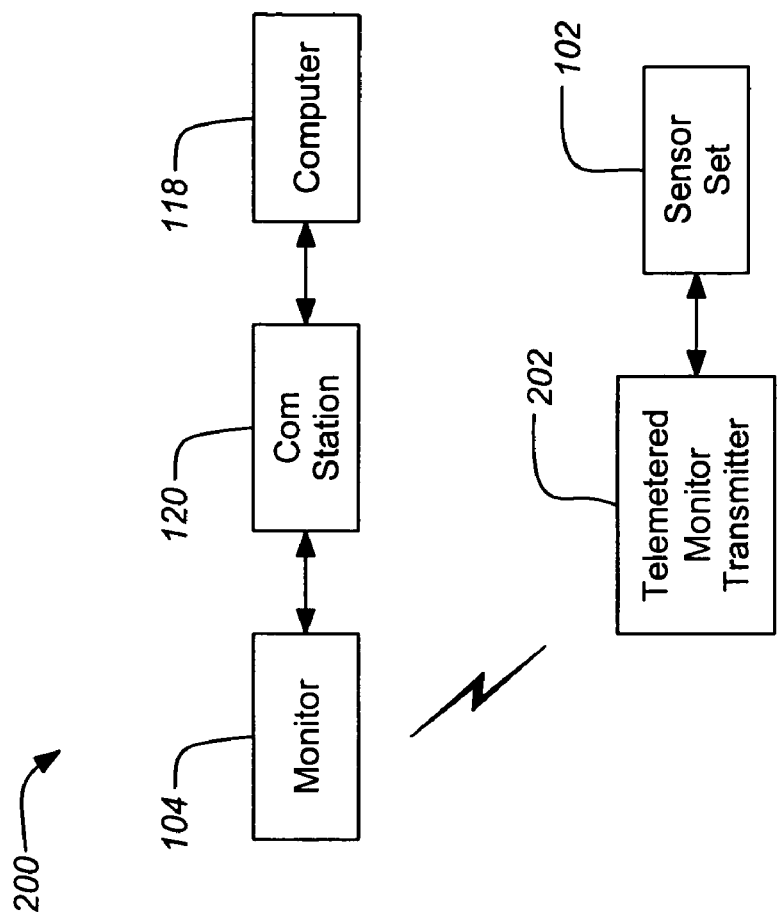
FIG. 1B is a block diagram of a telemetered characteristic monitor embodiment of the present invention.

FIG. 1B is a block diagram of a telemetered characteristic monitoring system embodiment of the invention. In this system embodiment 200, the sensor input 106 of the monitor 104 is a wireless receiver, such as a radio frequency (RF) receiver. The sensor set 102 provides a signal via wired link to a telemetered monitor transmitter 202, where the signal is interpreted and converted to an RF signal. The wireless receiver sensor input 106 of the monitor 104 converts the signal to data understandable to the monitor processor. With some advantages, the telemetered characteristic monitoring system can perform any or all the functions of the characteristic monitoring system of FIG. 1A.

A characteristic monitoring system 100, in accordance with a preferred embodiment of the present invention, includes a sensor set 102 and characteristic monitor device 104. The sensor set 102 generally utilizes an electrode-type sensor. However, in alternative embodiments, the system can use other types of sensors, such as electrically based sensors, chemically based sensors, optically based sensors, or the like. In further alternative embodiments, the sensors can be of a type that is used on the external surface of the skin or placed below the skin layer of the user. Preferred embodiments of a surface mounted sensor utilize interstitial fluid harvested from underneath the skin. In this context for example, real-time interstitial sensor glucose values can be correlated with blood glucose values. The sensor set 102 is connected to the monitor device 104 and provides a signal based upon the monitored characteristic (e.g., blood glucose). The characteristic monitor device 104 utilizes the received signal to determine the characteristic reading or value (e.g., a blood glucose level). In still other embodiments, the sensor may be placed in other parts of the body, such as, but not limited to, subcutaneous, dermal, sub-dermal, inter-peritoneal or peritoneal tissue The telemetered characteristic monitor transmitter 202 generally includes the capability to transmit data. In alternative embodiments, the telemetered characteristic monitor transmitter 202 can include a receiver, or the like, to facilitate two-way communication between the sensor set 102 and the characteristic monitor 104. In alternative embodiments, the characteristic monitor 104 can be replaced with a data receiver, storage and/or transmitting device for later processing of the transmitted data or programming of the telemetered characteristic monitor transmitter 202. In addition, a relay or repeater (not shown) can be used with a telemetered characteristic monitor transmitter 202 and a characteristic monitor 104 to increase the distance that the telemetered characteristic monitor transmitter 202 can be used with the characteristic monitor 104.

For example, a relay can be used to provide information to parents of children using the telemetered characteristic monitor transmitter 202 and the sensor set 102 from a distance. The information can be used when children are in another room during sleep or doing activities in a location remote from the parents. In a related embodiment, a relay can be used to provide information to medical professional and/or related caregiver regarding the physiological status of a user (e.g. a hypoglycemic event) in a situation where that event has not been acknowledged and/or addressed by the user within a specific time parameter (e.g. 15-45 minutes). In one illustrative embodiment, a physiological characteristic monitoring system includes a relay that automatically dials a predetermined telephone number as part of a notification scheme for an event that has not been acknowledged and/or addressed by the user. In further embodiments, the relay can include the capability to sound an alarm. In addition, the relay can be capable of providing telemetered characteristic monitor transmitter 202 data from the sensor set 102, as well as other data, to a remotely located individual via a modem connected to the relay for display on a monitor, pager or the like. The data can also be downloaded through the communication station 120 to a remotely located computer 118 such as a PC, laptop, or the like, over communication lines, by modem, wired or wireless connection. Wireless communication can include for example the reception of emitted radiation signals as occurs with the transmission of signals via RF telemetry, infrared transmissions, optical transmission, sonic and ultrasonic transmissions and the like. As disclosed herein, some embodiments of the invention can omit the communication station 120 and use a direct modem or wireless connection to the computer 118. In further embodiments, the telemetered characteristic monitor transmitter 202 transmits to an RF programmer, which acts as a relay, or shuttle, for data transmission between the sensor set 102 and a PC, laptop, communication station 118, a data processor, or the like. In further alternatives, the telemetered characteristic monitor transmitter 202 can transmit an alarm to a remotely located device, such as a communication station 118, modem or the like to summon help.

In addition, further embodiments can include the capability for simultaneous monitoring of multiple sensors and/or include a sensor for multiple measurements.

A purpose of the characteristic monitoring system 100 is to provide for better treatment and control in an outpatient or a home use environment. For example, the monitoring systems 100, 200 can provide indications of glucose levels, a hypoglycemia/hyperglycemia alarm and outpatient diagnostics. Embodiments of the invention are also useful as an evaluation tool under a physician's supervision.

The characteristic monitor device 104 receives characteristic information, such as glucose data or the like, from the sensor set 102 and displays and/or logs the received glucose readings. Logged data can be downloaded from the characteristic monitor 104 to a PC, laptop, or the like, for detailed data analysis. In further embodiments, the characteristic monitoring system 100, 200 can be used in a hospital environment, or the like. Still further embodiments of the present invention can include one or more buttons to record data and events for later analysis, correlation, or the like. Further buttons can include a sensor on/off button to conserve power and to assist in initializing the sensor set 102. The characteristic monitoring system 200 can also be employed with other medical devices to combine other patient data through a common data network system.

Further embodiments of the sensor set 102 can monitor the temperature of the sensor set 102, which can then be used to improve the calibration of the sensor. For example, for a glucose sensor, the enzyme reaction activity may have a known temperature coefficient. The relationship between temperature and enzyme activity can be used to adjust the sensor values to more accurately reflect the actual characteristic levels. In addition to temperature measurements, the oxygen saturation level can be determined by measuring signals from the various electrodes of the sensor set 102. Once obtained, the oxygen saturation level can be used in calibration of the sensor set 102 due to changes in the oxygen saturation levels and its effects on the chemical reactions in the sensor set 102. For example, as the oxygen level goes lower, the sensor sensitivity can be lowered. In alternative embodiments, temperature measurements can be used in conjunction with other readings to determine the required sensor calibration.

In preferred embodiments, the sensor set 102 facilitates accurate placement of a flexible thin film electrochemical sensor of the type used for monitoring specific blood parameters representative of a user's condition. Preferably, the sensor monitors glucose levels in the body, and can be used in conjunction with automated or semi-automated medication infusion devices of the external or implantable type as described in U.S. Pat. Nos. 4,562,751; 4,678,408; 4,685,903 or 4,573,994 (which are incorporated herein by reference), to control delivery of insulin to a diabetic patient. In addition, the monitor characteristic monitor 104 may typically be integrated into such a medication infusion device so that medication delivery and monitoring are conveniently provided within a single device.

Embodiments of the flexible electrochemical sensor can be constructed in accordance with thin film mask techniques to include elongated thin film conductors embedded or encased between layers of a selected insulative material, such as polyimide film or sheet, and membranes. The sensor electrodes at a tip end of the sensing portion are exposed through one of the insulative layers for direct contact with patient blood or other body fluids, when the sensing portion (or active portion) of the sensor is subcutaneously placed at an insertion site. The sensing portion is joined to a connection portion that terminates in conductive contact pads, or the like, which are also exposed through one of the insulative layers. In alternative embodiments, other types of implantable sensors, such as chemical based, optical based, or the like, can be used. Further description of flexible thin film sensors of this general type are found in U.S. Pat. No. 5,391,250, entitled "METHOD OF FABRICATING THIN FILM SENSORS", which is herein incorporated by reference. The connection portion can be conveniently connected electrically to the monitor 104 or a telemetered characteristic monitor transmitter 202 by a connector block (or the like) as shown and described in U.S. Pat. No. 5,482,473, entitled "FLEX CIRCUIT CONNECTOR", which is also herein incorporated by reference. Thus, in accordance with embodiments of the present invention, subcutaneous sensor sets 102 are configured or formed to work with either a wired or a wireless characteristic monitoring system 100, 200.

A. Glucose Monitor Status Checks

The physiological characteristic monitoring system 100, 200 can perform a status check to confirm that the monitor 104 is operating properly and calibrated to take glucose measurements. The processor 108 determines the status of the monitor for receiving the signal from the sensor set 102. The monitor status is based upon at least one of a plurality of conditions including the sensor activity condition, the sensor calibration condition and the telemetry condition. The display 114 shows different observable indicators depending upon the status of the monitor 104.

Figure 2A:
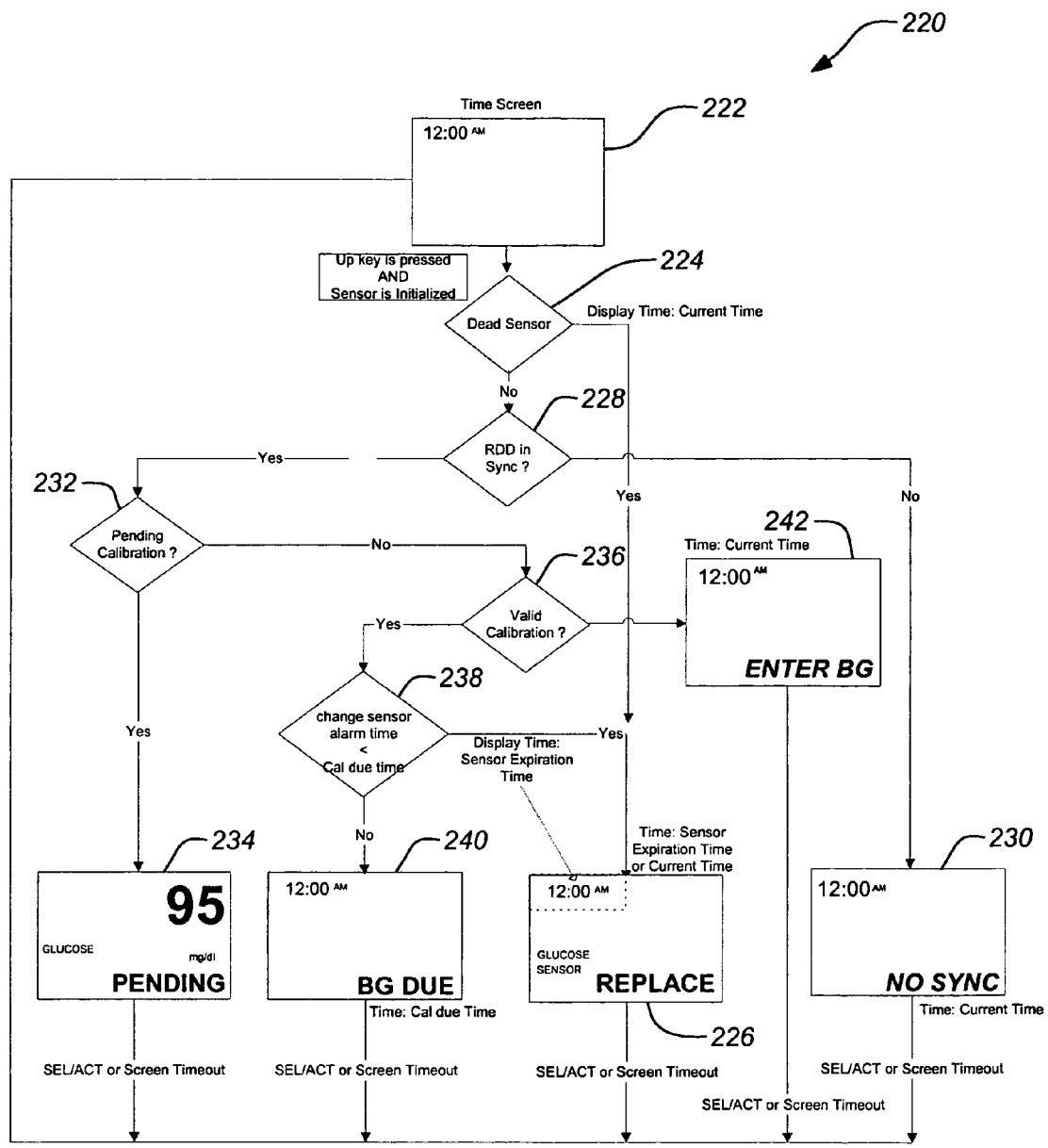
FIG. 2A is a flowchart of a status check algorithm for a characteristic monitor embodiment of the present invention.

FIG. 2A is a flowchart 220 of an exemplary status check algorithm for a characteristic monitor embodiment of the present invention. Beginning at the default time screen 222 showing the current time, a user can press a key (e.g. the UP key) to initiate the status check. The processor 108 first performs a sensor activity condition check 224 to determine if there is an expired or dead sensor. If the sensor is determined to be dead, the display 114 shows a sensor "REPLACE" prompt 226 with the current time, which indicates that the sensor has expired and replacement of the sensor set 102 is required immediately. If the sensor is determined to be active by the sensor activity check 224, the processor 108 performs a telemetry condition check 228 to determine if the monitor 104 is synchronized with the telemetered monitor transmitter 202 coupled to the sensor set 102. If the monitor 104 and the transmitter 202 are not synchronized, a "NO SYNC" indicator 230 is shown on the display 114. If the devices are synchronized, a calibration condition check 232 is performed by the processor 108 to determine first whether a calibration of the sensor set 102 is pending (i.e., whether the monitor 104 is currently processing a previously entered blood glucose reference value, for example from a meter, to calibrate the sensor set 102). If a calibration is pending, the display 114 shows a "PENDING" indicator 234. If a calibration is not pending, the processor 108 checks whether the sensor calibration is currently valid 236. If the calibration is not valid, the display shows an "ENTER BG" indicator 242 with the current time, which indicates that a blood glucose reference value (e.g., from a blood glucose meter) is required by the monitor 104 to calibrate the sensor set 102. If the calibration is valid, the processor 108 then checks that the sensor expiration time is after the next calibration due time 238, and the display 114 shows a "BG DUE" indicator 240 with the time that the next calibration is due. If the sensor expiration time is before the next calibration due time, the display 114 shows the "REPLACE" prompt 226 with the time that the sensor will expire and replacement of the sensor set 102 can be required.

B. Glucose Monitor Calibration Reference Value Entry

Figure 2B:
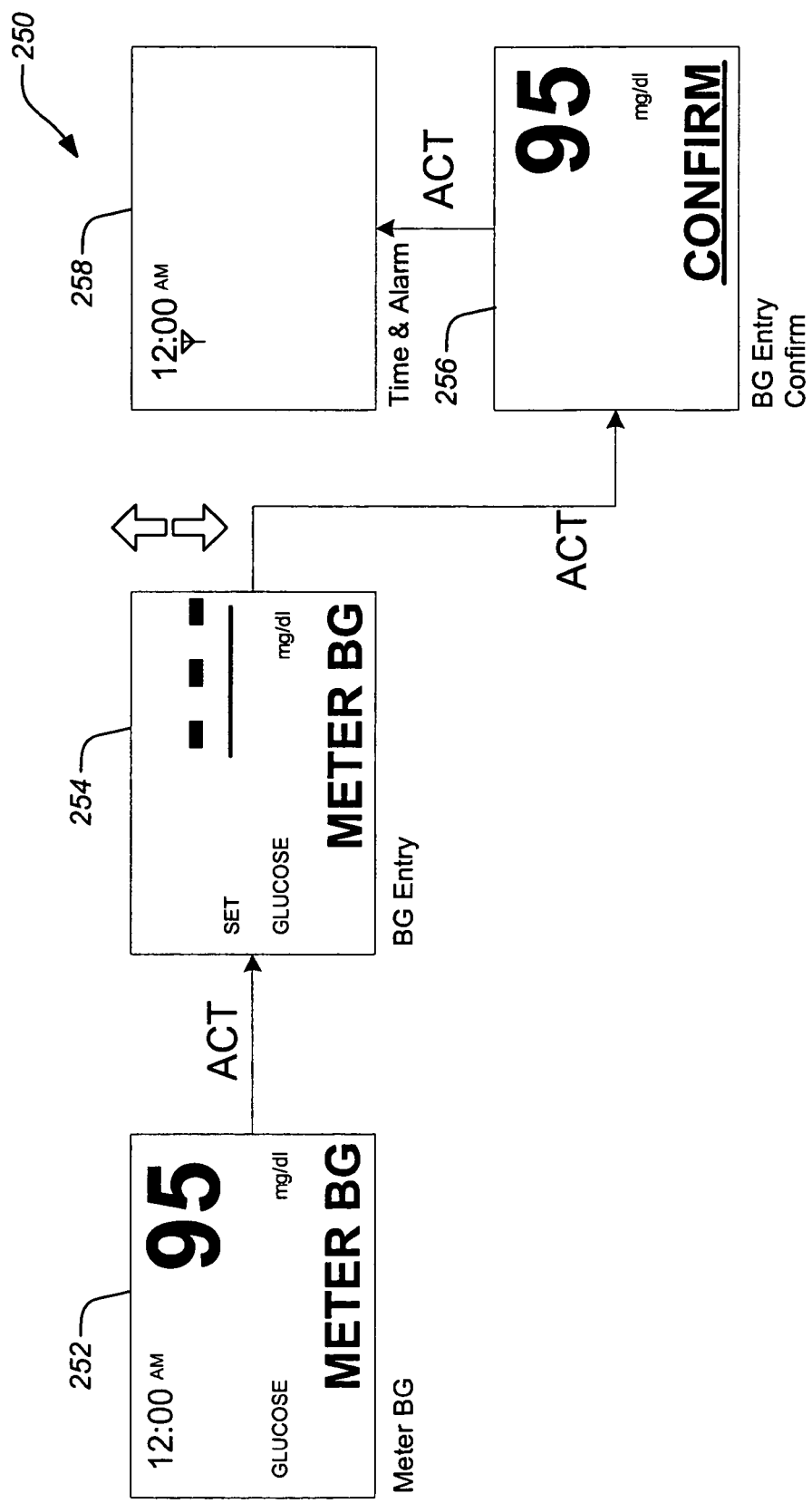
FIG. 2B is a flowchart of screens for entering a reference value to calibrate a characteristic monitor embodiment of the present invention.

FIG. 2B is an exemplary flowchart 250 of screens for entering a reference value to calibrate a characteristic monitoring system 100, 200 in accordance with an embodiment of the present invention. While a calibration is pending or valid as a result of entry of a calibration reference value (e.g., a blood glucose value measured by a blood glucose meter), the display 114 shows the calibration reference value and time of the most recent valid entry in the meter screen 252. In particular embodiments, the time of the most recent valid entry is unaffected by a change in a system time setting of the monitor 104. In other embodiments, the time of the most recent valid entry may be shifted in accordance with a change in a system time setting of the monitor 104. From the meter screen 252, pressing a button (e.g., the ACT/activate button) allows entry of a new calibration reference value in the entry screen 254. After entry of the new value (e.g., using the up and down arrow buttons and then pressing the ACT/activate button), the display 114 shows a confirmation screen 256, which requires confirmation of the value entered (e.g., by pressing the ACT/activate button) to release the display to the default time screen 258.

3. Dynamic Glucose Monitoring Functions

Embodiments of the present invention include different types of continuous glucose monitors that identify trends in blood glucose dynamics to facilitate enhanced treatment of diabetes. In general, a first illustrative monitor can be used to anticipate a glucose "crash" (or other hypoglycemic incident) before the onset of debilitating symptoms. Another illustrative monitor can be used to detect an inadequate nocturnal basal rate and alert the patient in order to avoid an impaired fasting glucose incident. Another illustrative monitor can anticipate hyperglycemic (or hypoglycemic) incidents by detecting trends toward those levels and help the patient avoid such incidents. Another illustrative monitor can assist a patient in maximizing athletic performance in endurance type activities (e.g., a marathon race) by detecting trends toward hypoglycemic levels.

The disclosed embodiments monitor the dynamics of a physiological characteristic such as blood glucose levels. These embodiments utilize this dynamic monitoring to provide functionality including the anticipation of glucose crash and alerting the patient, the detection of inadequate nocturnal basal rate, the anticipation of hyperglycemic (or hypoglycemic) incidents and maximizing athletic performance. All of these features can be implemented in software operating in the monitor's microprocessor and/or designed into an application specific integrated circuit (ASIC) or other specialized circuitry. Also, dynamic glucose monitoring functions use periodic measurements of a glucose level.

A. Monitor for Anticipating a Glucose Crash

In one embodiment of the invention, a monitor anticipates a glucose crash by monitoring trends in glucose levels. For example, the monitor can alert the patient when glucose levels are rapidly decreasing. By monitoring such trends or a rate information of measured glucose levels, the monitor can provide a much better warning system to alert the user with enough time to stabilize and reverse a dangerous physiological condition.

In some embodiments of the invention, the monitor measures glucose more frequently than typical glucose monitoring devices. For example, one embodiment of the invention measures approximately every minute, whereas other monitors measure at a lower rate (e.g., but not limited to, once per 5 minutes). Frequent measurements are taken because of the short time intervals which are evaluated. Alternative embodiments may utilize more frequent measurements, such as, but not limited to, 10 seconds, 1 second, or the like.

In an illustrative embodiment, the monitor periodically measures glucose, analyzes the present trend, determines whether a glucose crash incident is probable and appropriately alerts the patient. At some frequent interval (e.g., but not limited to, once per minute), the device measures the glucose level, applies a smoothing filter to the result, and records the filtered value. The smoothing filter may take a weighted sum of past sensor values (so called finite impulse response—FIR—filter), a weighted sum of past sensor values and past filtered values (so called infinite impulse response—IIR—filters), may use simple clipping algorithms (e.g. limit the percent change in filtered output), or employ models to predict the output (e.g. Weiner and Kalman filter designs). For example, if the most recent (filtered) value is in the "qualifying range", the monitor can calculate the slope of a line fit to the most recent values (most likely, but not limited to, using a Saritzky gulag filter) and determine if the slope is steeper than a selected threshold rate (e.g., but not limited to, 3% or declining at more than 30 mg/dL in ten minutes). If the slope equals or exceeds the threshold rate, a glucose crash incident is likely and the monitor alerts the patient accordingly.

Those skilled in the art will understand that in some embodiments the qualifying range can be a closed range (e.g., but not limited to, between 100 and 150 mg/dL) and in other embodiments the qualifying range can be an open range (e.g., but not limited to, greater than 100 mg/dL). By first identifying whether a most recent value is within the qualifying range, further calculation of the dynamic behavior of the physiologic characteristic can be avoided. Thus, the determination of a glucose crash can be unconcerned with rate magnitudes occurring when the current characteristic value is outside of the range (of course, other alarms, which merely monitor the current characteristic value, can be triggered when the reading is too high or too low). However, in alternate embodiments, the slope can be calculated and compared to the threshold rate with every new value. In further embodiments, multiple qualifying ranges and threshold rates can be applied to evaluate the glucose dynamics and determine triggering a glucose crash warning.

In one preferred embodiment, the monitor determines that a glucose crash is likely if three criteria are met. The criteria are as follows. The first, dG/dT (the rate of glucose level change) is negative, can be considered for example in situations where blood glucose levels are dropping (e.g., but not limited to, when a value pertaining to the rate of glucose change is negative). The second, |dG/dT| exceeds a threshold rate, can be considered in contexts, for example where a specified blood glucose change rate is exceeded for a specified sustained period (e.g., but not limited to, greater than 3% per minute for 10 minutes). The third, G, the glucose level, can be considered for example, when this value begins dropping starting within a specified range, (e.g., but not limited to, 100-150 mg/dL).

In some embodiments, these criteria can be parameterized to allow the user to customize the values. The qualifying range, threshold rate and period can be general values, applied to all users, or determined from factors specific to the individual user. For example, the monitor can include a feature to adjust the qualifying glucose level range, the maximum rate of glucose change, or in some embodiments, the sustained time period length. In addition, in some embodiments, any or all of the dynamic glucose monitoring functions can enabled or disabled, selectively or together.

The following control program pseudo code provides an example of a programming routine performed by the processor of the monitor to implement an embodiment of the invention.

```
REPEAT every minute)
{
    Measure glucose level    g_i
    Filter g_i and store the filtered value g'_i
    IF(g'_i is in range 100-150 mg/dL)
        THEN
            Fit a line to the most recent 10 filtered (or,
alternatively, unfiltered) values
            IF (dG/dT for that line < ( –3% per minute )
                THEN
                    Alert the patient and record in history
                ENDIF
        ENDIF
}
END REPEAT
```

Figure 3A:
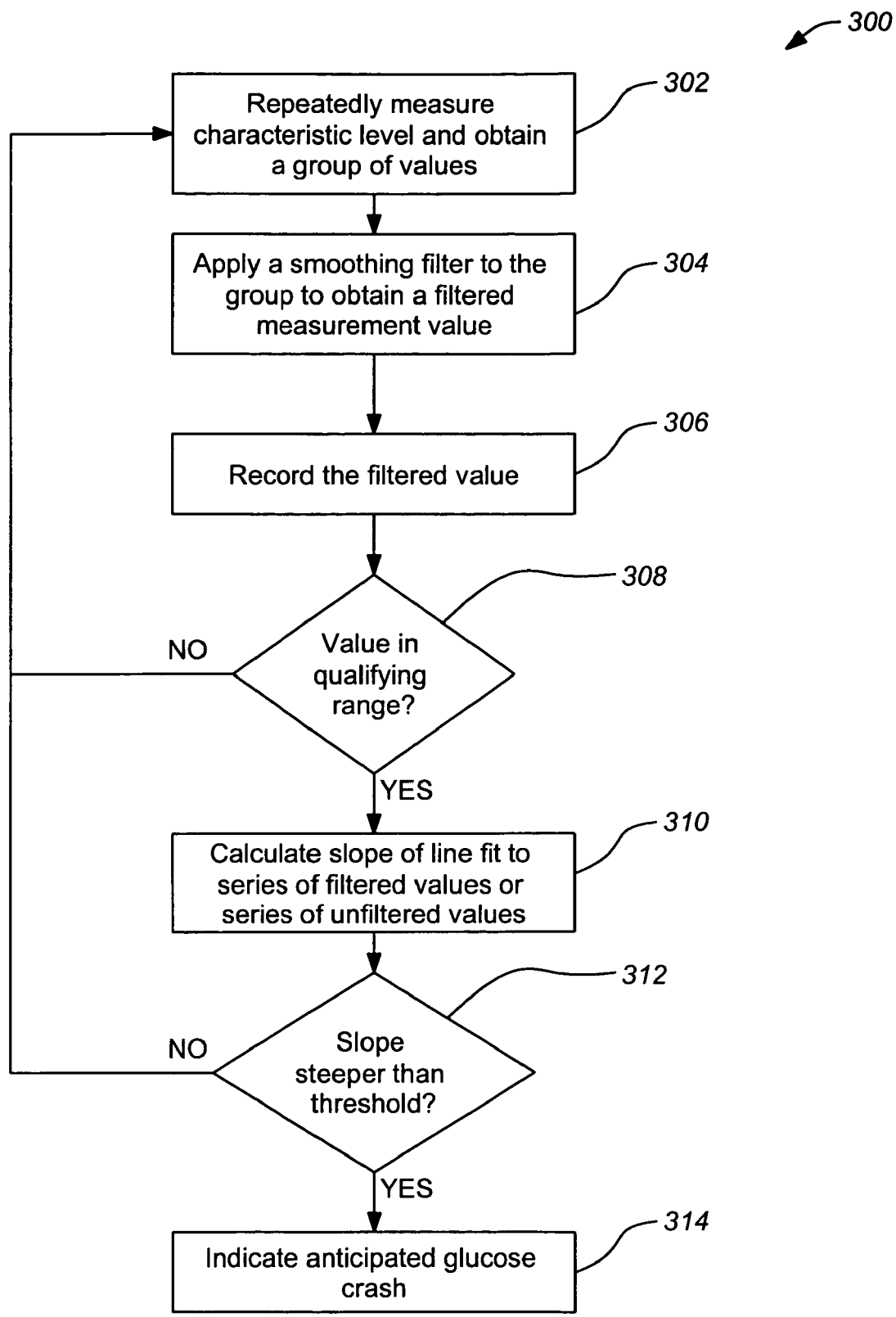
FIG. 3A is a flowchart of a method for anticipating a glucose crash.

FIG. 3A is a flowchart of a method for anticipating a glucose crash 300. At block 302, a characteristic level is repeatedly measured to obtain a group of characteristic level values. Following this at block 304, a smoothing filter can be applied to the group of characteristic level values to produce a filtered measurement value. The filtered measurement value is recorded at block 306. At block 308 it is determined if the recorded value falls within a qualifying range (e.g., but not limited to, between 100 to 150 mg/dL). If not, the process returns to block 302. If the recorded measurement is within the range, a slope of a line fit to a recent series of recorded filtered values is calculated at block 310. The calculated slope is compared to a threshold rate (e.g., but not limited to, –3% per minute) at block 312. If the calculated slope is not steeper than the threshold rate the process returns to block 302. If the slope exceeds the threshold rate, an anticipated glucose crash is indicated at block 314. Alternative embodiments may utilize similar logic for when the glucose level is already outside of the range and continues to drop. In addition in an alternative preferred embodiment of the invention, one can utilize a raw data measurement (e.g. a group of characteristic level values) to determine a derivative as an alternative to using a filtered measurement value to determine a derivative.

B. Monitor for Detecting an Inadequate Nocturnal Basal Rate

In another embodiment of the invention, the characteristic monitor can be used to detect an inadequate nocturnal basal rate. This embodiment generally applies to diabetic patients using an insulin infusion device that continually administers insulin at a patient controlled basal rate. The monitor detects an inadequate basal rate (i.e., but not limited to, "low basal rate" or a "high basal rate"), by monitoring trends in glucose levels. The monitor then alerts a patient in the early morning, when glucose levels are high and relatively steady, low and relatively stable or changing rapidly. This gives the patient time to adjust the basal rate of the infusion device upward or downward to and avoid an impaired fasting glucose incident.

The monitor operates to track the characteristic level rate. For example, every 5 minutes the monitor measures and records the glucose level. Once a day (e.g., but not limited to, 3 hours before to the anticipated wakeup time), the monitor calculates the average blood glucose and the rate of blood glucose change for the previous hour. The monitor can then determine a prediction of the "morning glucose" level at wake up based upon the calculated average blood glucose and the rate of blood glucose change. In one embodiment the "morning glucose" is predicted assuming that the rate of change remains constant, however in other embodiments nonlinear characteristic curves and functions can be applied in making the prediction. If the anticipated "morning glucose" level is greater than a high threshold value (e.g., but not limited to, 126 mg/dL), or less than a low threshold value (e.g., but not limited to, 60 mg/dL), an alarm is sounded. This will allow time for the infusion device basal rate to be adjusted appropriately. In alternative embodiments, different times before anticipated wakeup, different high threshold values, or different low threshold values, may be used.

In some embodiments, the triggering criteria can also be parameterized to allow the user to customize the values. In some embodiments, the user is allowed to set the values for the controlling parameters. For example, the user can set the qualifying low and high glucose levels as well as the anticipated waking time. For each of the settings a default value can be used in the absence of a user setting. For example, a default low glucose level of 60 mg/dL, a default high glucose level of 126 mg/dL and an anticipated waking time of 7:00 AM can be used. In addition, the entire function can be enabled and disabled.

Figure 3B:
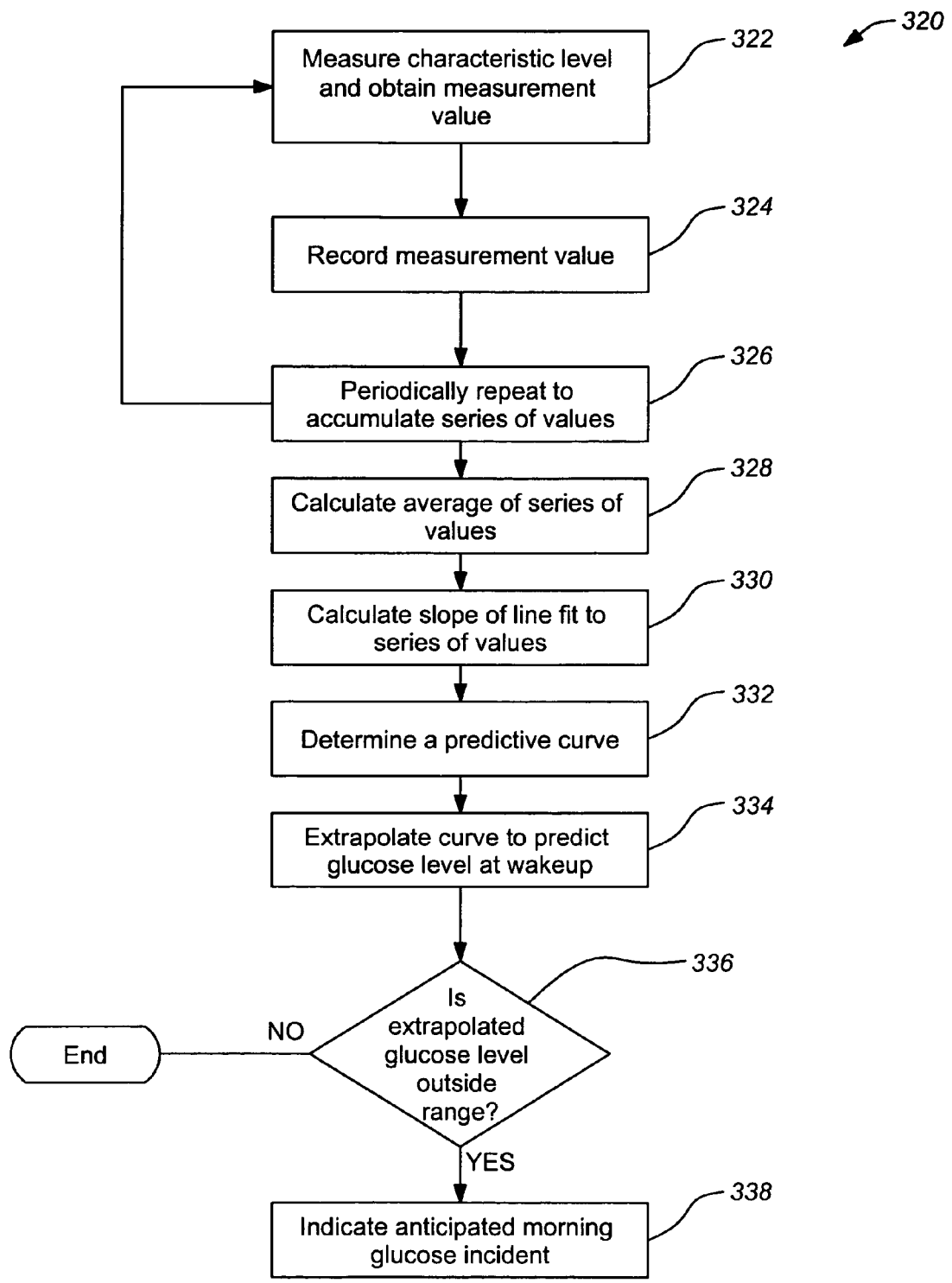
FIG. 3B is a flowchart of a method for detecting an inadequate nocturnal basal rate.

FIG. 3B is a flowchart of a method for detecting an inadequate nocturnal basal rate 320. At block 322, the method begins by measuring a characteristic level to obtain a measurement value. The value is recorded at block 324. Measuring and recording is repeated periodically to obtain a series of values at block 326. At block 328, the average of the series of values is calculated. At block 330, a slope of a line fit to the series of values is calculated. The calculated slope and average of the series of values are then used to determine a predictive curve at block 332. At block 334, the curve is extrapolated to predict a glucose level at wakeup. Those skilled in the art understand that such calculations are not limited to slope y=mx+b, and that, in this context, one can use alternative filtered arrangements as are known in the art. The extrapolation is performed some time before wakeup (e.g., but not limited to, 3 hours prior) to provide enough time to correct any impending negative condition. The predicted glucose level is compared to an acceptable range at block 336. If the predicted glucose value falls within the range, the process ends. If the predicted glucose value falls outside the range, a morning glucose incident is reported at block 338.

C. Monitor for Anticipating Hyperglycemic Incidents

In another embodiment of the invention, a glucose monitor anticipates a hyperglycemic (or hypoglycemic) incident by monitoring trends in glucose levels. The monitor alerts the patient when a "relatively steady increase" (or decrease) in glucose levels occurs. The monitor periodically measures glucose, analyzes the present trend, determines whether a hyperglycemic (or hypoglycemic) incident is probable and appropriately alerts the patient.

In one embodiment, the device measures glucose values at a specific time interval (e.g. once every minute), and then, e.g. at 5 minute intervals, applies a smoothing filter to this group of values and records the filtered value. If the most recent (filtered) value exceeds a threshold value (e.g., but not limited to, 180 mg/dL), the monitor calculates the slope of a line fit to a recent series of recorded values (for example, but not limited to, six values). If the slope is greater than a threshold rate (e.g., but not limited to, 3% per minute), a hyperglycemic incident is likely and the monitor alerts the patient. For hypoglycemic incidents, values and thresholds corresponding to low glucose levels would be used.

The threshold value is applied in a similar manner to the "qualifying range" applied in determining a glucose crash previously discussed. The threshold value effectively operates as an open range (e.g., but not limited to, greater than 180 mg/dL). In other embodiments, the threshold value can be a closed range. Therefore, determining a hyperglycemic incident can be unconcerned with values below the threshold value (as determining a hypoglycemic incident can be unconcerned with values above a threshold value). In one embodiment, a slope calculation can be avoided if the current reading is outside the range. However, in alternate embodiments, the slope can be calculated and compared to the threshold rate with every new reading. In further embodiments, multiple qualifying ranges and threshold rates can be applied to evaluate the glucose dynamics and determine triggering a hyperglycemic (or hypoglycemic) incident warning.

Here again, in some embodiments the criteria can be parameterized to allow the user to customize the controlling values for anticipating hyperglycemic (or hypoglycemic) incidents. For example, some embodiments can allow the user to set the glucose threshold level and/or the threshold rate. Embodiments of the invention can also use default parameters if no user settings are provided (e.g., but not limited to, a threshold level of 180 mg/dL and a maximal rate of 3% per minute). Embodiments of the invention can also enable and disable this function.

Figure 3C:
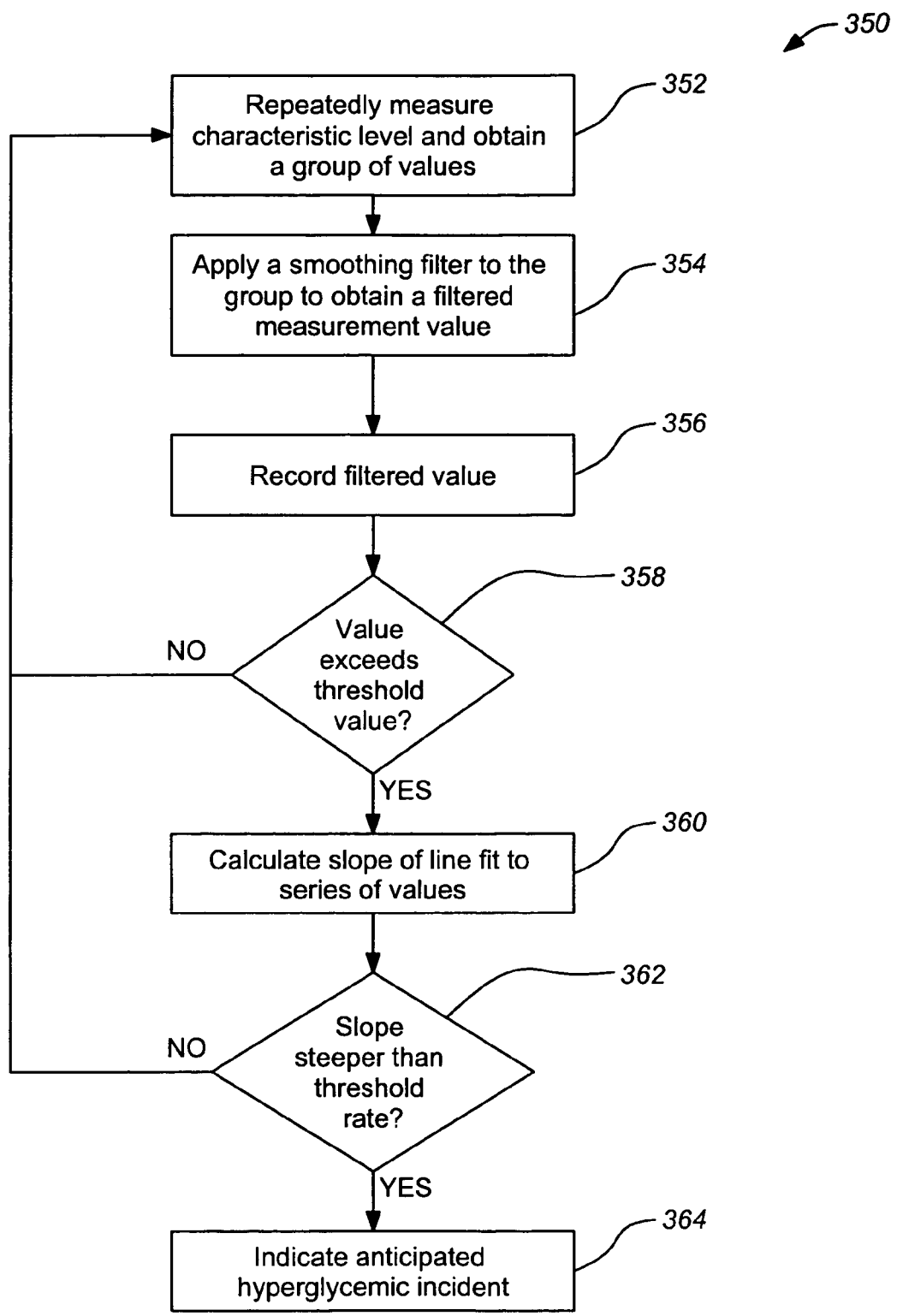
FIG. 3C is a flowchart of a method for anticipating a hyperglycemic incident.

FIG. 3C is a flowchart of a method for anticipating a hyperglycemic incident 350. The method begins at block 352 by repeatedly measuring a characteristic level to obtain a group of values. At block 354, a smoothing filter is applied to the group of values to obtain a filtered measurement value. The filtered value is recorded at block 356. The recorded value is compared to a threshold value at block 358. If the recorded value does not exceed the threshold value (e.g., but not limited to, 180 mg/dL), the process returns to block 352. If the recorded value does exceed the threshold value, a slope of a line fit to a recent series of values is calculated at block 354. The calculated slope is compared to a threshold rate (e.g., but not limited to, +3% per minute) at block 362. If the slope is not steeper than the threshold rate, the process returns to block 352. If the slope is steeper than the threshold rate, an anticipated hyperglycemic incident is reported at block 364. For hypoglycemic incidents, corresponding steps for low glucose levels would be used. As noted previously, estimates of dG/dt may be calculated by a variety of methods known in the art including the slope (and that such calculations are not limited to, for example, determinations based on y=mx+b).

D. Monitor for Maximizing Athletic Performance

Dynamic monitoring can also be used to provide feedback based upon the engaged activity of the user. For example, the monitor can be used to maximize performance during an endurance type activity (e.g., but not limited to, a marathon race). The endurance athlete strives to burn glucose rather than fat and accordingly needs to anticipate low glucose levels and ingest carbohydrates early enough to avoid low glucose levels.

In such embodiments, the monitor anticipates low glucose levels and alerts the athlete to ingest carbohydrates. It is important to note that this embodiment is not strictly anticipating hypoglycemic incidents. Instead it is anticipating low glucose levels where it would otherwise be too late for the athlete to compensate by ingesting carbohydrates and still perform effectively and/or at full capacity.

In one embodiment, once a minute, the device measures a glucose level, applies a smoothing filter and records the filtered value at 5-minute intervals. If the most recent recorded (i.e., filtered) value is in a qualifying range (e.g., but not limited to, 60-140 mg/dL), the processor calculates the slope of a line fit to the most recent six filtered values and determines if the slope is steeper than −1% (i.e., but not limited to, 30 mg/dL in 30 minutes). If the rate of decline exceeds this threshold, a low glucose level is likely and the monitor alerts the athlete accordingly. Thus, for example, but not limited to, to trigger an alarm, the glucose level rate, dG/dT, is negative with a magnitude greater than 1% per minute for 30 minutes beginning in range 60-140 mg/dL.

Similar to the glucose crash monitor, in embodiments for maximizing athletic performance, the qualifying range can be a closed range (e.g., but not limited to, between 60 and 140 mg/dL) or an open range (e.g., but not limited to, less than 140 mg/dL). By first identifying whether a most recent value is within the qualifying range, further calculation of the dynamic behavior of the physiologic characteristic is avoided. However, other alarms which merely monitor the current characteristic value can be triggered when the reading is too high or too low. In alternate embodiments, the slope can be calculated and compared to the threshold rate with every new value. In further embodiments, multiple qualifying ranges and threshold rates can be applied to evaluate the glucose dynamics and determine triggering a low glucose warning.

Here too, these criteria can be parameterized to allow the user to customize the values. Typically, the monitor will allow a user to set the qualifying glucose range and/or enable and disable the function. A default qualifying range (e.g., but not limited to, 60-140 mg/dL) can be used.

Figure 3D:
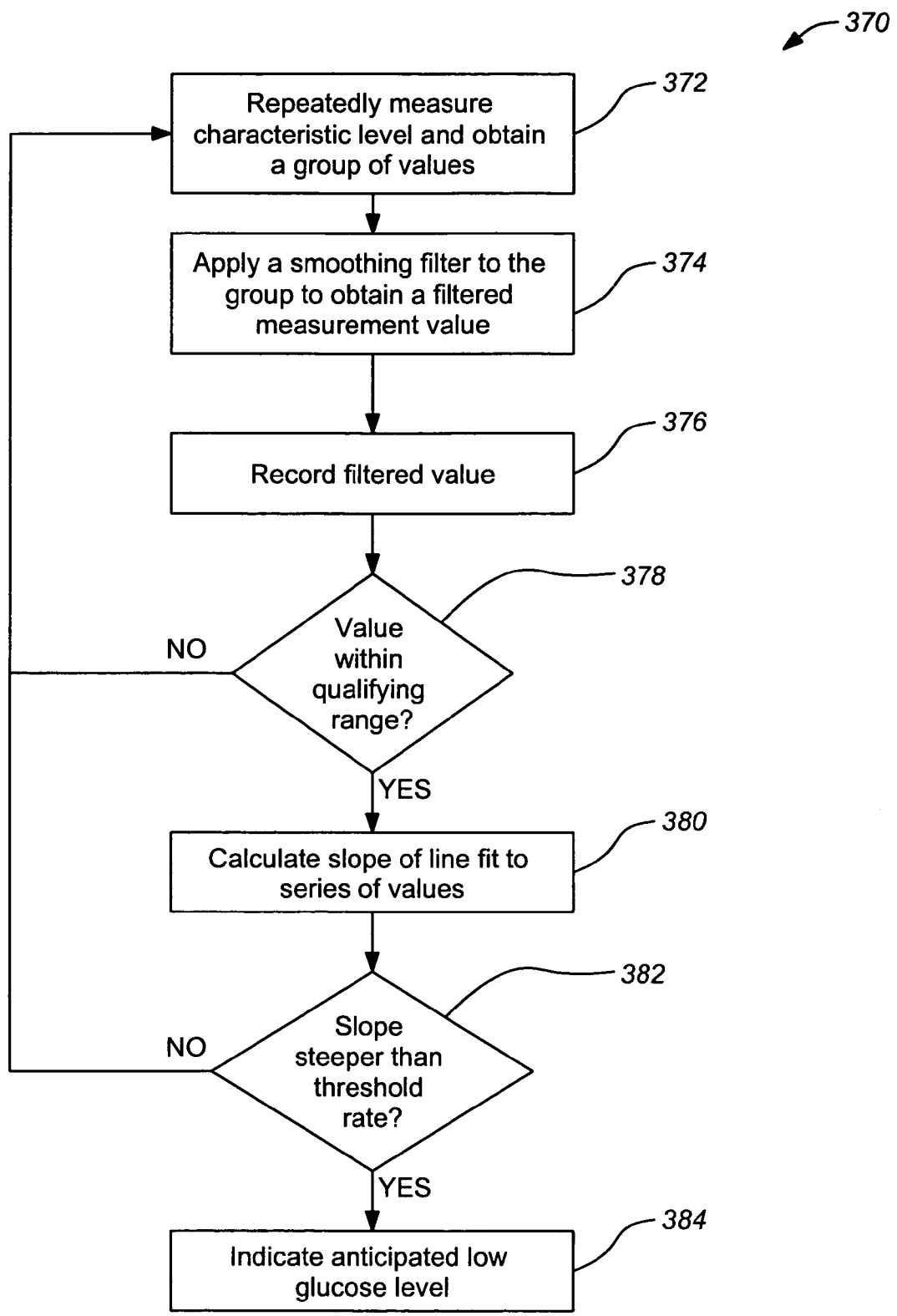
FIG. 3D is a flowchart of a method for maximizing athletic performance.

FIG. 3D is a flowchart of a method for maximizing athletic performance 370. The process begins at block 372, where a characteristic level is repeatedly measured to obtain a group of characteristic level values. Following this at block 374, a smoothing filter can be applied to the group of characteristic level values to produce a filtered measurement value. The filtered measurement value is recorded at block 376. At block 378 it is determined if the recorded value falls within a qualifying range (e.g., but not limited to, between 60 to 140 mg/dL). If not, the process returns to block 372. If the recorded measurement is within the range, a slope of a line fitted to a recent series of recorded filtered values is calculated at block 380. The calculated slope is compared to a threshold rate (e.g., but not limited to, −1% per minute) at block 382. If the calculated slope is not steeper than the threshold rate the process returns to block 372. If the slope exceeds the threshold rate, an anticipated low glucose level is indicated at block 384. As noted previously, estimates of dG/dt may be calculated by slope as well as other methods known in the art.

Glucose Alarm Functions

Embodiments of the invention can utilize various advanced alarm functions. For example, in some embodiments multiple alarms can be independently set by the user. In further embodiments, user input can direct review of the alarm history and also alter the alarm display to suit the user's preference. Alarm settings for embodiments of the invention can also include an alarm snooze or "blackout" period as well as an alarm repeat delay.

A. Multiple Glucose Alarm Functions

Embodiments of the invention can employ multiple alarms that can be independently set by the user. For example, a continuous glucose monitoring system can have multiple alarms for different glucose values. The system can allow a user to set threshold glucose values that define a "narrow" glucose range (as compared to the ordinary alarm limits). If the user's glucose level passes outside the "narrow" range, an alarm can sound. This alarm alerts the user to monitor his glucose levels more closely. The system can sound a second alarm (preferably having a sound distinguishable from the first "narrow" range alarm) in the event the user's glucose level reaches a more dangerous condition requiring immediate action. Alarm indications may be audible, tactile, vibratory, visual, combinations of alarm indications, or the like. In the case of visual alarm indications, but not limited to, green lights can be displayed while the user's glucose level remains within the defined "narrow" range; yellow for the first alarm level; and red for the second alarm level. The visual alarm indications may flash and/or also be combined with other alarm indications.

Although the above example describes a two-layer alarm system, further embodiments of the invention can incorporate multiple alarm layers. In addition, the alarms can be set in ranges, or separate high and low glucose level alarms can be set. Distinctive sounds can be used for each alarm. For example, each successive high glucose level alarm can have, but is not limited to having, a higher pitch. Successive low glucose level alarms can each have, but are not limited to having, lowering pitches. Alternately, intermittent or wavering volumes that also increase in pitch according to the severity of the condition can be used. In still other embodiments, the user can select or program alarm tones and other sounds and assign them to the various alarms. Also, in some embodiments, these distinguishable alarms can also be set at different volume levels. In addition, as discussed above, the alarms are not limited to audible signals; some embodiments of the invention can also utilize visual alarms, such as flashing lights or displays, or tactile alarms, such as vibrating indicators.

In still further embodiments, threshold values and associated alarms can be set according to a schedule. For example, but not limited to, particular alarms can be set to be active only during selected portions of the day.

Figure 4A:
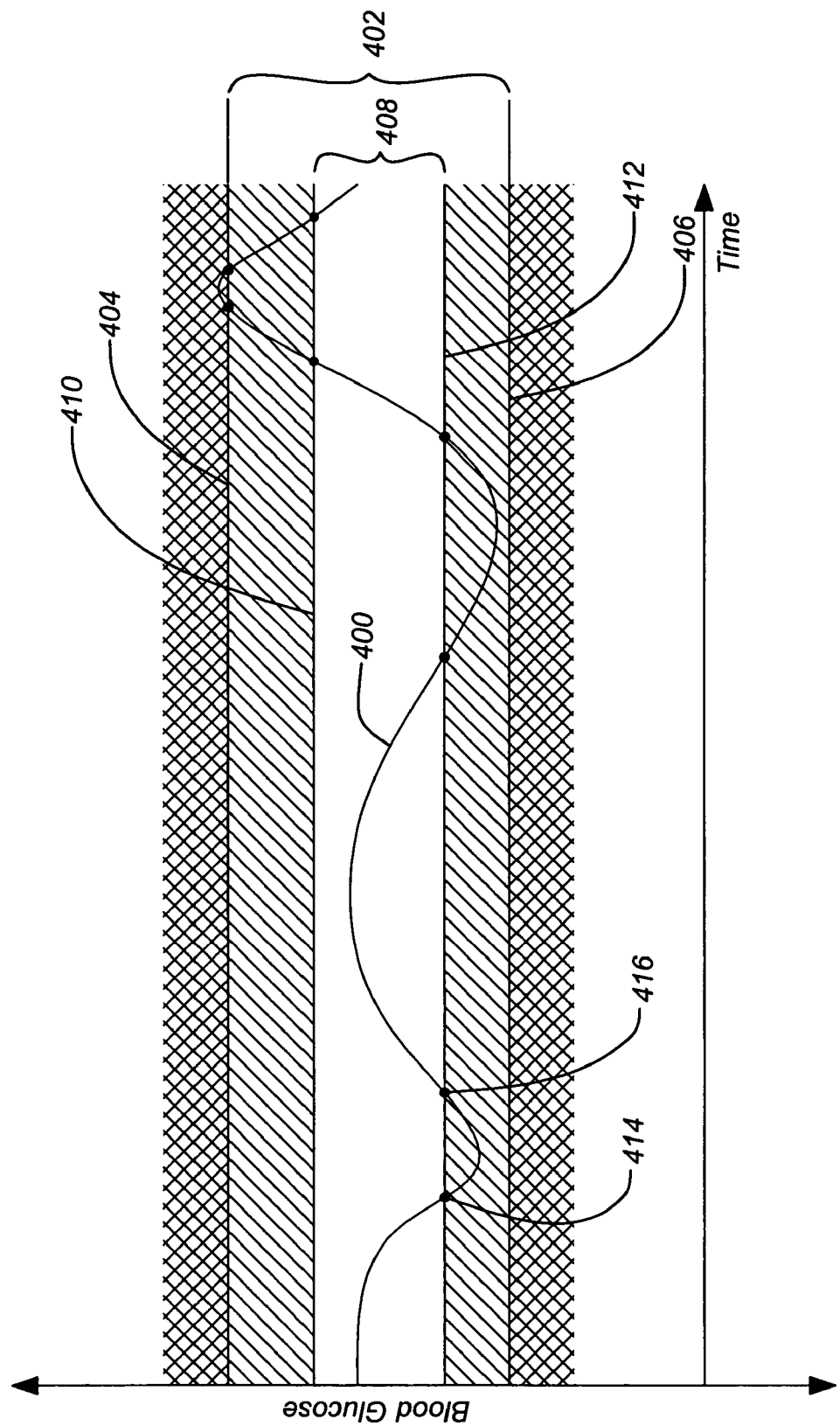
FIG. 4A illustrates a multiple alarm function of the invention.

FIG. 4A illustrates a multiple alarm function of the invention. A plot of the monitored characteristic value 400 (e.g., blood glucose) changing over time is shown. A typical wide alarm range 402 is defined by an upper threshold value 404 and a lower threshold value 406. If the monitored characteristic value 400 should exceed the defined range and cross either threshold, an alarm is initiated to indicate to the user to check his blood glucose. In one embodiment, a distinctive alarm can be associated with the alarm range 402. Thus, the same alarm is produced whether the range 402 is exceeded by passing the upper threshold value 404 or the lower threshold value 406. In other embodiments, distinctive alarms can be assigned to each threshold value 404, 406. In further embodiments of the invention, other alarm ranges can also be set. For example, a second narrower range 408 can be set with a lower upper threshold value 410 than that of the wider range 402; and a higher lower threshold value 412 than that of the wider range 402. As with the wider range 402, an alarm is initiated if the narrower range is exceeded by the monitored characteristic value 400. Here also, alarms can be the same or different for each threshold value 410, 412.

The ability to set different ranges and associated alarms allows the monitor to immediately convey some information about the condition of the user even before checking the actual readings. Particularly, using the narrower range 408 and associated alarms allows the user to know of a negative trend that does not require the same urgency as an alarm triggered by the wider range 402. In effect, the user is able to set multiple alarms, each indicating a different level of urgency and/or different conditions. In some embodiments, threshold values for alarms can also be set independent from ranges.

Instill further embodiments, alarms or indicators can be set according to the direction in which a threshold value is crossed by the monitored characteristic value 400. For example, as the monitored characteristic value 400 crosses a lower threshold value 412 from the narrow range (e.g., but not limited to, at point 414), one type of alarm can be provided. However, when the monitored characteristic value 400 crosses a lower threshold value 412 from the wider range 402 (e.g., but not limited to, at point 416), another type of alarm can be provided. The difference in the alarms is appropriate because only the former case indicates a worsening of the user's condition. In the latter case, the transition actually indicates an improvement in the user's condition. Thus, in some embodiments of the invention, alarms will only be given when crossing a threshold indicates a worsening of the user's condition. In other embodiments, an indicator will also be given when a threshold has been crossed in an improving direction. In these cases, either the same indicator (sound, light, display or other) or different indicators can be used. In a similar manner, reminders can be set to indicate to a user various conditions (not necessarily negative) that will aid in convenient therapy management.

The multiple alarm function of the invention can be readily incorporated with any of the individual alarm functions and settings such as discussed hereafter.

B. Individual Alarm Functions and Settings

In further embodiments of the invention, a physiological characteristic monitor can incorporate various individual alarm functions and settings to enhance convenient operation by a user. As typical of the monitoring system 100, 200 shown in FIGS. 1A and 1B, the monitor includes a sensor input capable of receiving a signal from a sensor, the signal being based on a sensed physiological characteristic value of a user, and a processor for operating an alarm based on user input from an input device. The alarm indicates an alarm condition where the sensed physiological characteristic value exceeds a set range. In preferred embodiments of the invention, the physiological characteristic value is a measurement related to a blood glucose level in the user and the alarm indicates a glycemic condition. Operating the alarm comprises setting parameters of the alarm based on the user input from the input device. For example, the blood glucose level or value that will activate a hypoglycemia or hyperglycemia alarm may be set by the user utilizing the input device. The hypoglycemia alarm may be set to trigger if the user's blood glucose level is less than or equal to 60, 65, or 70 mg/dl (or any other desired level), and the hyperglycemia alarm may be set to trigger if the user's blood glucose level is greater than or equal to 150, 160, or 175 mg/dl (or any other desired level).

Figure 4B:
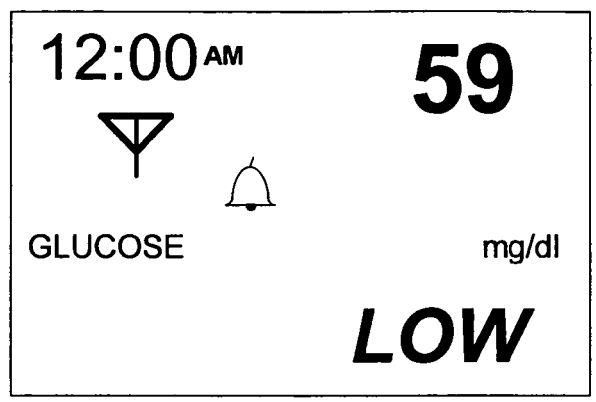
FIGS. 4B and 4C illustrate respectively hypoglycemia and hyperglycemia alarm screens.
Figure 4C:
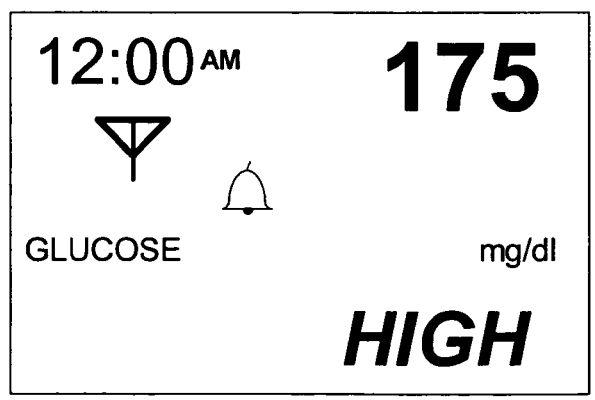

FIGS. 4B and 4C illustrate the hypoglycemia and hyperglycemia alarm screens, respectively. In each case, the display shows the measurement of the concentration of blood glucose indicating the glycemic condition, preferably until the alarm is acknowledged by the user. Furthermore, the display shows a time of the alarm. In particular embodiments, the alarm indicates the glycemic condition only if the monitor is calibrated, although in alternative embodiments, the alarm may indicate the glycemic condition regardless if the monitor is calibrated.

In the illustrated embodiment, the display shows a LOW indicator when the measurement of the concentration of blood glucose is below a specified level for a hypoglycemia alarm, such as 60 mg/dl. Similarly, the display shows a HIGH indicator when the measurement of the concentration of blood glucose is above a specified level for a hyperglycemia alarm, such as 150 mg/dl. In some embodiments, alarm indications may be other visual indicators (e.g., lights, flashing displays, or the like), audible, tactile, and/or vibratory. For example, a hypoglycemia alarm can be indicated by at least two audible descending tones, and a hyperglycemia alarm can be indicated by at least two audible ascending tones.

In further embodiments of the invention, an alarm repeat delay period is employed. Subsequent alarms are prevented for the alarm repeat delay period after the measurement of the concentration of blood glucose first indicates a glycemic condition. For example, the alarm repeat delay period can be less than 20 minutes (e.g. approximately 17.5 minutes) for the glycemic condition comprising a hypoglycemic condition. In another example, the alarm repeat delay period is less than 1 hour (e.g. approximately 52.5 minutes) for the glycemic condition comprising a hyperglycemic condition. In alternative embodiments, the alarm repeat delay period may be other time periods, such as 10 minutes, 15 minutes, 30 minutes, 1½ hours, 2 hours, or the like.

Figure 4D:
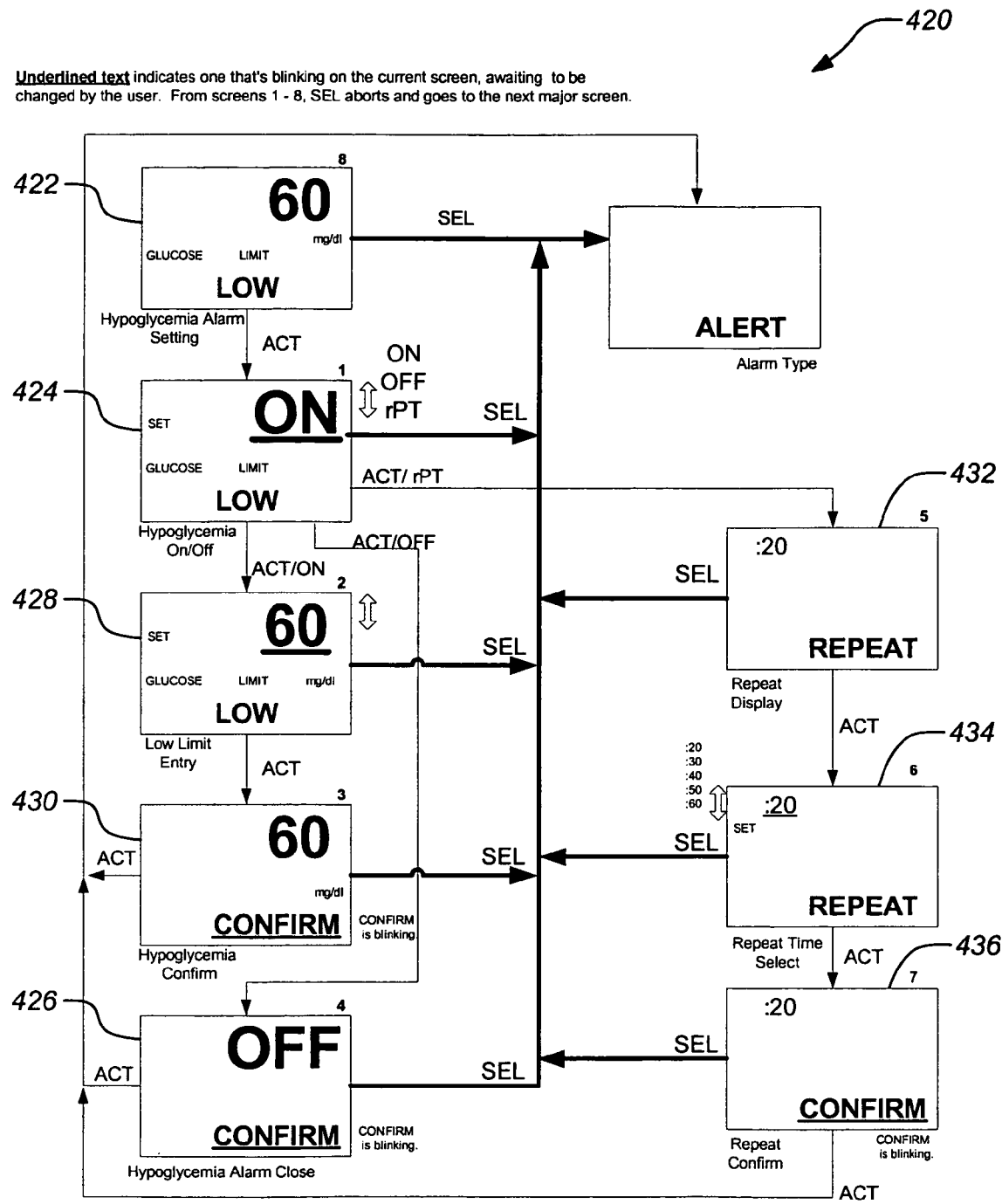
FIGS. 4D and 4E illustrate respectively flowcharts of screens for setting hypoglycemia and hyperglycemia alarms.
Figure 4E:
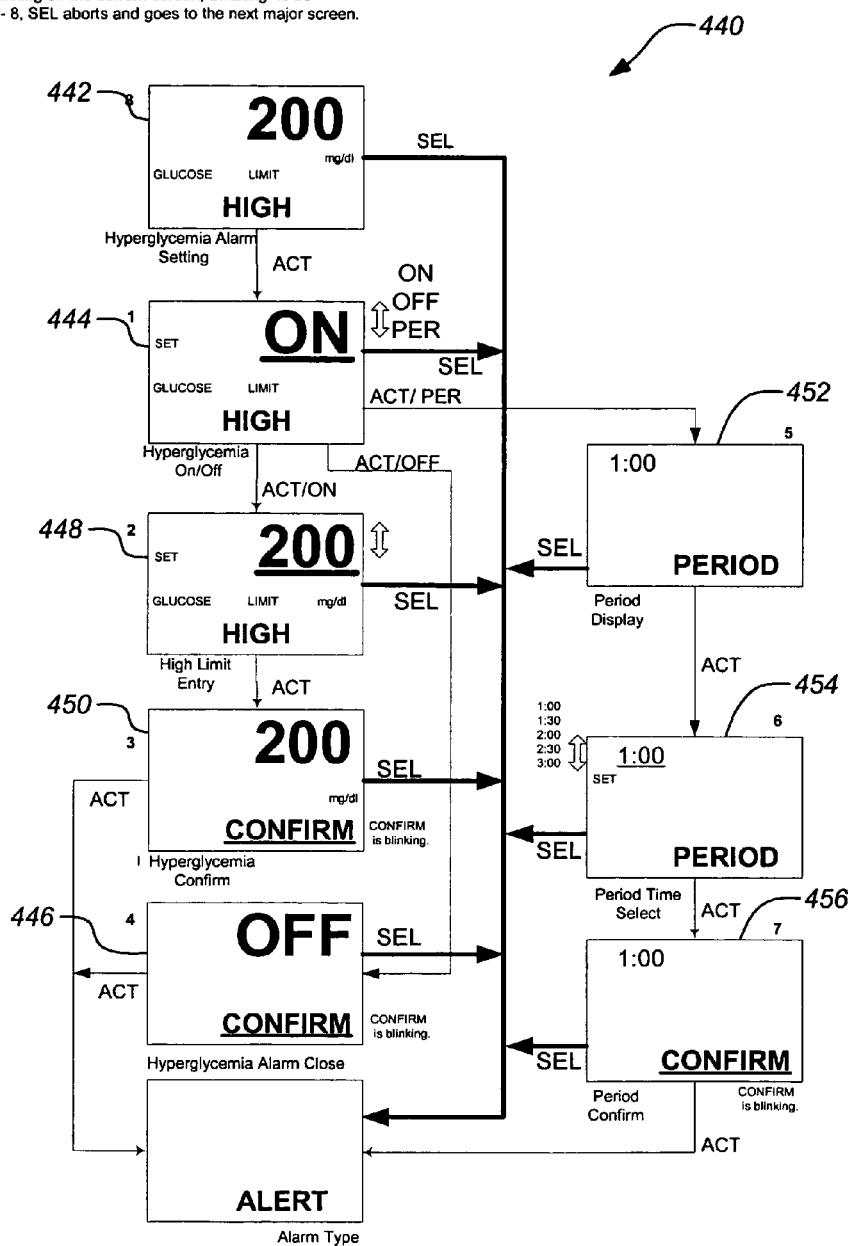

In particular embodiments, the level of the measurement of the concentration of blood glucose from the sensor that will trigger a low limit (or hypoglycemia) alarm or a high limit (or hyperglycemia) alarm can be set based upon input from the user. Particularly, these two alarm levels can be separately set. FIGS. 4D and 4E show exemplary hypoglycemia and hyperglycemia alarm setting algorithms, respectively. FIG. 4D shows an exemplary hypoglycemia alarm setting flowchart 420. To begin setting the hypoglycemia alarm, from the hypoglycemia alarm setting screen 422, the ACT/activate button is pressed, and the hypoglycemia alarm activation screen 424 is entered. From this screen 424, the user can select setting the hypoglycemia alarm on, off or entering the alarm repeat setting function menu. If the user sets the hypoglycemia alarm off and presses the ACT/activate button, an alarm off confirmation screen 426 is presented. If the hypoglycemia alarm is set on and the ACT/activate button is pressed, the low limit entry screen 428 is presented. The low limit entry screen 428 allows the user to scroll through low limit alarm level settings using up and down arrow buttons to specify that the hypoglycemia alarm will trigger if the user's blood glucose level is less than or equal to 60, 65, or 70 mg/dl, or any other desired level. After setting the low limit alarm level, pressing the ACT/activate button again presents a hypoglycemia low limit alarm level confirmation screen 430 for confirming the specified hypoglycemic blood glucose level.

From the hypoglycemia alarm activation screen 424, if the alarm repeat setting function is selected, the alarm repeat display screen 432 is entered, which allows the user to set a period for delaying a repeated check of the hypoglycemia alarm condition. The current alarm repeat delay period is shown in the alarm repeat display screen 432. Pressing the ACT/activate button allows the user to enter the repeat time select screen 434. Alternatively, the alarm repeat display screen 432 may be omitted, and the repeat time select screen 434 is entered once the alarm repeat setting function is selected. In the repeat time select screen 434, the alarm repeat delay period blinks while being set by the user utilizing the input device. The user can scroll through a list of delay increments and select the desired alarm repeat delay period from the list of delay increments. The alarm repeat delay period has a default value of 20 minutes for the hypoglycemia (low limit) alarm level. For convenience, the scrolled list of delay increments can wrap around, beginning again when one end of the list is reached. For the low limit alarm level, the alarm repeat delay period can be selected from a group of values differing in 10 minute increments. For example, the alarm repeat delay period can be selected from 20, 30, 40, 50 and 60 minutes for the low limit alarm level. In alternative embodiments, the alarm repeat delay period may be selected from a group of values differing in other time increments, such as 5, 15, or 20 minutes, or further, may be specified using up and down arrow buttons and then pressing the ACT/activate button. After selecting the alarm repeat delay period, pressing the ACT/activate button displays the alarm repeat delay confirmation screen 436 for confirming the period selection.

FIG. 4E shows an exemplary hyperglycemia alarm setting flowchart 440. From the hyperglycemia alarm setting screen 442, if the ACT/activate button is pressed, the hyperglycemia alarm activation screen 444 is entered. From this screen 444, the user can select setting the hyperglycemia alarm on, off or entering the alarm repeat setting function menu. If the user sets the hyperglycemia alarm off and presses the ACT/activate button, an alarm off confirmation screen 446 is presented. If the hyperglycemia alarm is set on and the ACT/activate button is pressed, the high limit entry screen 448 is presented. The high limit entry screen 448 allows the user to scroll through high limit alarm level settings using up and down arrow buttons to specify that the hyperglycemia alarm will trigger if the user's blood glucose level is greater than or equal to 150, 160, 170, 175, or 180 mg/dl, or any other desired level. After setting the high limit alarm level, pressing the ACT/activate button again presents a hyperglycemia high limit alarm level confirmation screen 450 for confirming the specified hyperglycemic blood glucose level.

The alarm repeat delay period for the hyperglycemia alarm is set in the same manner as that for the hypoglycemia alarm described above with respect to FIG. 4D; however, the alarm repeat delay period is typically set separately for a low limit alarm level and a high limit alarm level because the desired delays are different in each case. In general, the hyperglycemia alarm repeat delay period may be longer than that of the hypoglycemia alarm. From the hyperglycemia alarm activation screen 444, if the alarm repeat setting function is selected, the alarm repeat display screen 452 is entered, which allows the user to set a period for delaying a repeated check of the hyperglycemia alarm condition. The current alarm repeat delay period is shown in the alarm repeat display screen 452. Pressing the ACT/activate button allows the user to enter the repeat time select screen 454. Alternatively, the alarm repeat display screen 452 may be omitted, and the repeat time select screen 454 is entered once the alarm repeat setting function is selected. In the repeat time select screen 454, the hyperglycemia alarm repeat delay period is selected in a manner similar to the hypoglycemia alarm repeat delay period described above with respect to FIG. 4D, and then pressing the ACT/activate button displays the alarm repeat delay confirmation screen 456 for confirming the period selection. The alarm repeat delay period can have a default value of 1 hour for the hyperglycemia (high limit) alarm level. For the high limit alarm level, the alarm repeat delay period can be selected from a group of values differing in 30 minute increments. For example, the alarm repeat delay period can be selected from 1, 1½, 2, 2½ and 3 hours for the hyperglycemia alarm level. In alternative embodiments, the alarm repeat delay period may be selected from a group of values differing in other time increments, such as 15 or 20 minutes or 1 hour, or further, may be specified using up and down arrow buttons and then pressing the ACT/activate button.

As noted above, the multiple alarm function of the invention can be incorporated with various specific alarm features. For example, the alarm repeat delay function can be set differently for hypoglycemic alarms and hyperglycemic alarms of different severities. If a lower threshold hyperglycemic alarm is triggered, a relatively long repeat delay may be invoked. However, if a higher threshold hyperglycemic alarm is triggered, a shorter repeat delay may be used so that the user is warned more frequently because of the severity of his condition.

As disclosed herein, embodiments of the invention that incorporate a plurality specific alarm features can be used to optimize the utility of the alarm functions associated with hypoglycemia and/or hyperglycemia. In an alarm associated with hypoglycemic events for example, one can monitor a plurality of relevant physiological characteristic and can further utilize multiple alarm modes for alerting the user as to the status of the one or more characteristics. For example, an illustrative first alarm can be based upon a detection scheme for physiological glucose levels reaching a predetermined concentration (i.e. a dangerously low concentration). An illustrative second alarm can be based upon a detection scheme for a specific rate in which physiological glucose concentrations are changing in the user. In such situations, embodiments of the invention disclosed herein can provide a first alarm based upon the rate of glucose concentration change in advance of a second alarm that is predicated upon physiological glucose concentrations reaching a predetermined threshold concentration. In such embodiments of the invention, the physiological characteristic threshold criteria for triggering an alarm can be modulated to for example, modulate the period of time between the first and second alarm functions according to the needs of the user.

In certain embodiments of the invention a user can employ a device that monitors both of the above-noted glucose detection schemes simultaneously. In such embodiments the device can employ a combination of the two alerts where the predetermined triggers for the various alarm functions are different. For example it is observed that when both the rate and specific concentrations of glucose are monitored, the rate change detector usually alerts before the fixed threshold change detector but has a higher false alarm rate. Consequently certain embodiments of the invention can employ a combination of the two alerts where the threshold for the physiological parameter that triggers each alert are different. In one such embodiment for example, the fixed concentration threshold parameter can be a higher or more stringent than the rate of concentration change threshold parameter. Such combinations provide devices that exhibit a good sensitivity while minimizing false alerts. In such contexts, one can further use information about both the rate of change and the current value to create a rule or mathematical formula which allows one to maximize the efficiency of detection while minimizing the occurrence of false alerts.

One such illustrative embodiment of the invention is a device, comprising a sensor input capable of receiving at least one signal from a sensor, the signal being based on a plurality of sensed physiological characteristic values of a user of the device; and a processor coupled to the sensor input for operating a plurality of alarms based on the received signal from the sensor; wherein the processor is capable of activating each of the plurality of alarms according to a different sensed physiological characteristic value of the plurality of sensed physiological characteristic values. Preferably, the plurality of sensed physiological characteristic values include the blood glucose concentrations in the user; and the rate of change of blood glucose concentrations in the user over a predetermined time period. In such devices, a first alarm can be activated when glucose concentrations exhibit a predetermined rate of change and a second alarm can be activated when glucose concentrations reach a predetermined value. Optionally the criteria for activating the first alarm are more stringent than the criteria for activating the second alarm. In this context, criteria for activating an alarm are considered to be more stringent when they are based on parameters associated with greater physiological stress (e.g. a higher blood glucose concentration in hyperglycemia and/or a lower blood glucose concentration in hypoglycemia).

In a preferred embodiment of the invention, the processor is capable of activating an alarm based on an evaluation of both the blood glucose concentrations in the user and the rate of change of blood glucose concentrations and the alarm is activated based on a mathematical comparison of the blood glucose concentrations in the user and the rate of change of blood glucose concentrations in the user. In an exemplary embodiment, the alarm is activated when the relationship between the blood glucose concentrations in the user and the rate of change of blood glucose concentrations in the user meet a certain criteria. Optionally such criteria are determined by one or more mathematical formulae or algorithms that are based upon calculations that consider the specific the relationship between the blood glucose concentrations in the user and the rate of change of blood glucose concentrations in situations typically considered dangerous to the user.

Figure 4F:
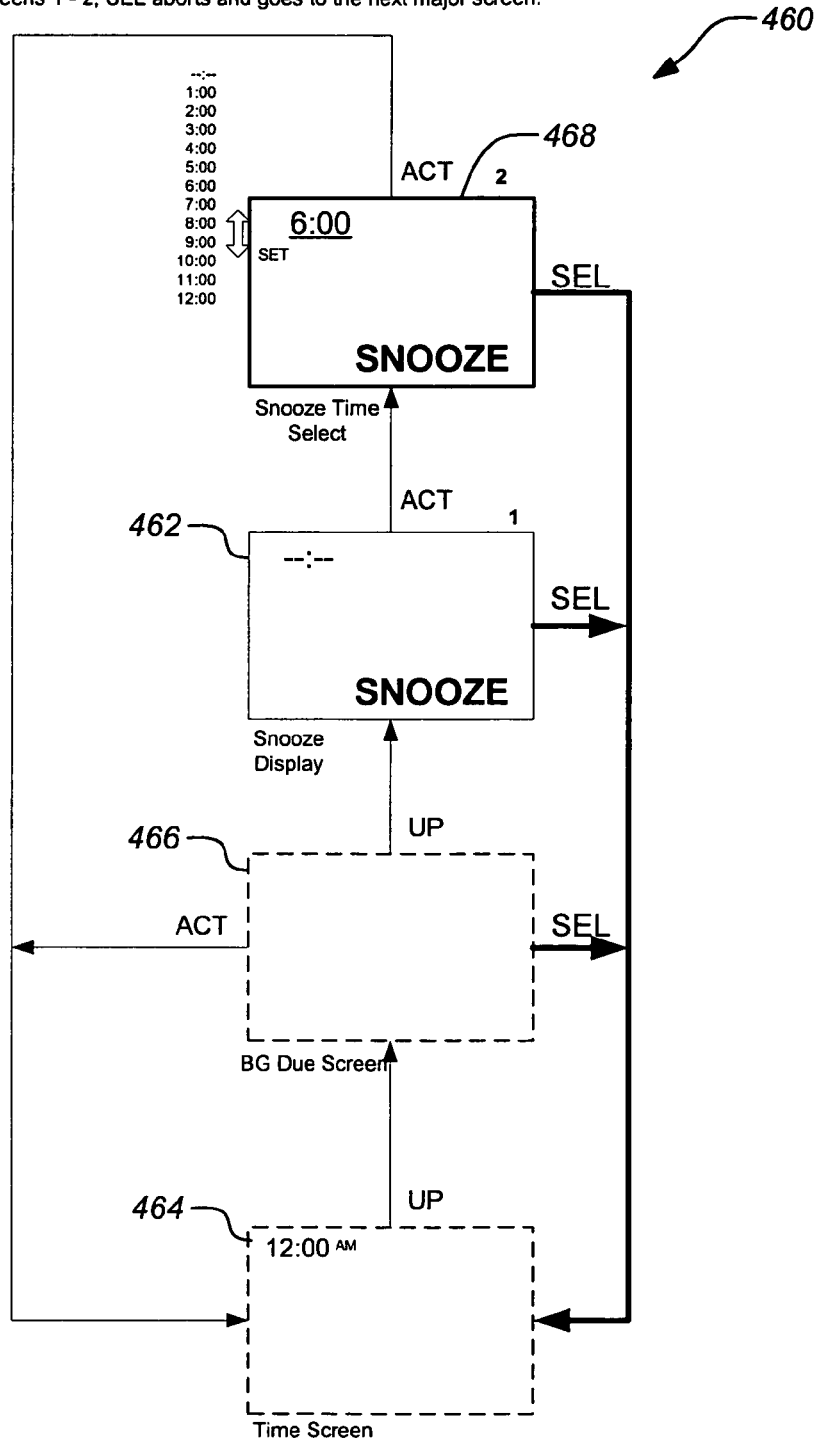
FIG. 4F illustrates a flowchart of screens for setting a hyperglycemia alarm snooze.

FIG. 4F illustrates a hyperglycemia alarm snooze setting flowchart 460. The hyperglycemia alarm snooze function sets an alarm snooze period for temporarily disabling the alarm. The snooze function is set by the user utilizing the input device. In some embodiments, the alarm snooze period is only available for a hyperglycemia alarm, although in other embodiments, the alarm snooze period may also be available for a hypoglycemia alarm. Generally, the snooze function is available only when the snooze period is running and the monitor is calibrated, although in alternative embodiments, the snooze function may be available regardless if the monitor is calibrated. Further, the alarm snooze period is preferably deactivated upon any adjustment of the hyperglycemia alarm setting described above with respect to FIG. 4E. The snooze setting flowchart 460 begins at the snooze display screen 462, which can be entered by scrolling past the default time screen 464 and the BG due screen 466. From the snooze display screen 462, pressing the ACT/activate button will produce the snooze time select screen 468. In this screen 468, a user can select the desired period for the snooze function to operate, and the alarm snooze period blinks while being set by the user utilizing the input device. The alarm snooze period can be set by the user scrolling through a list of snooze period increments and selecting the desired alarm snooze period from the list of snooze period increments. For example, the list of snooze period increments can include 1, 2, 3, 4, 5, 6, 7, 8, 9, 10, 11 and 12 hours, and for convenience, the list of snooze period increments wraps around as it is scrolled by the user. In alternative embodiments, the snooze period may be selected from a list of other time increments, such as 15 or 30 minutes, or further, may be specified using up and down arrow buttons and then pressing the ACT/activate button. When the snooze function is activated, the display shows time remaining of the alarm snooze period and an indicator (e.g. an "S") showing that the snooze function is active.

It may be instructive to note that, although both the alarm repeat delay function and the alarm snooze function prevent alarms for specified periods, they are not the same. One difference between the two functions can generally be identified by how each function is initiated. The alarm repeat delay is initiated (assuming the function is activated and set by the user) in response to a first alarm. In contrast, the alarm snooze function is activated by the user directly, either by directing the monitor to snooze immediately or scheduling a snooze at a specified time. For example, a user may schedule a snooze during sleeping hours that occur at some known time.

Just as with the alarm repeat delay, the multiple alarm function of the invention can also be incorporated with the alarm snooze function. For example, the snooze function can be set differently for hypoglycemic alarms and hyperglycemic alarms of different severities. The snooze function can function normally when a lower threshold hyperglycemic alarm is set (i.e. ignore the alarm). However, when a higher threshold hyperglycemic alarm is set, the snooze function may be overridden due to the severity of the user's condition.

Figure 4G:
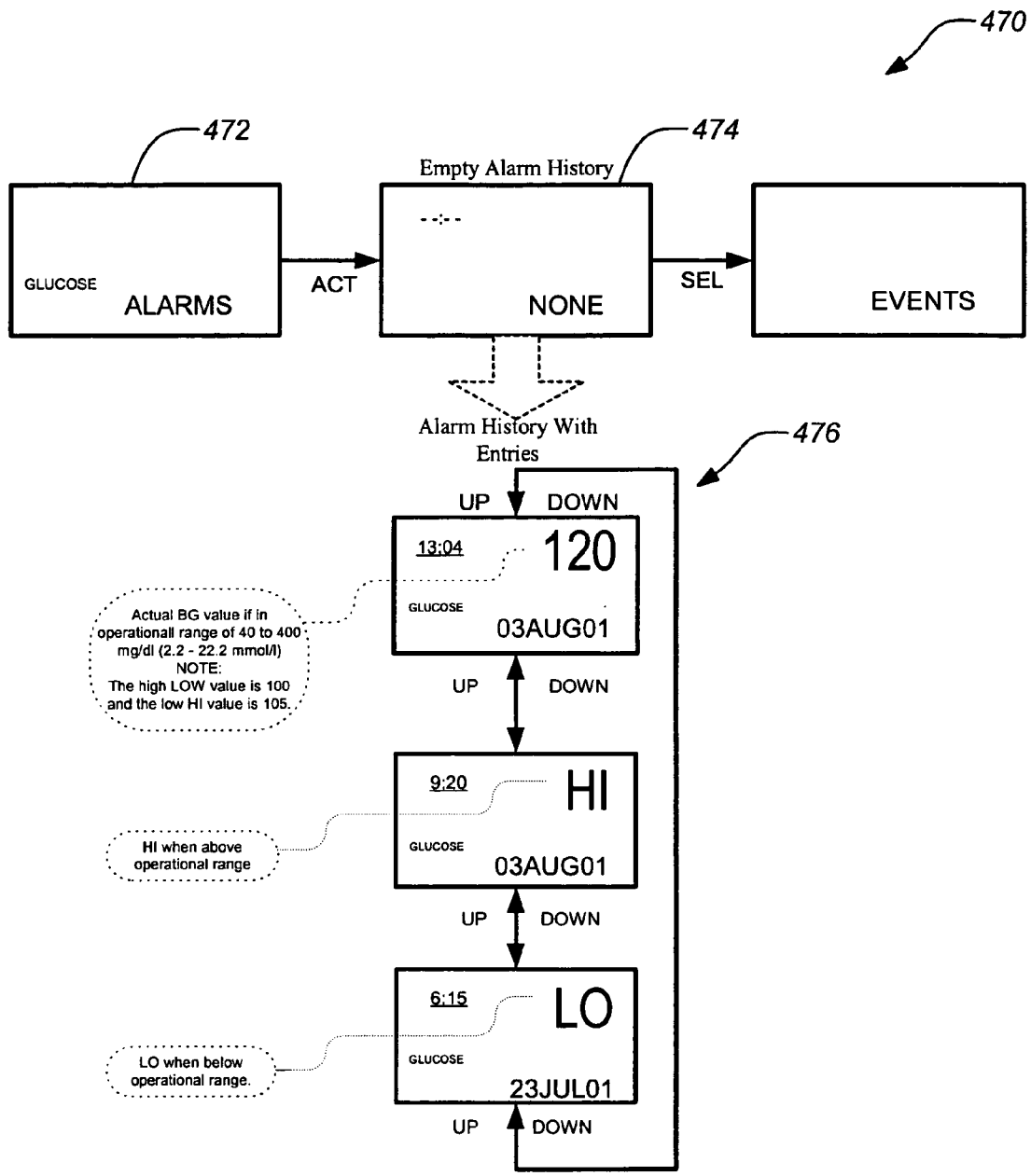
FIG. 4G illustrates a flowchart of screens for reviewing a history of glycemia alarms in accordance with an embodiment of the invention.

FIG. 4G illustrates glycemia alarm history review in accordance with an embodiment of the invention. Operating the alarm history review can allow a user to review a historical list of the alarms indicating a glycemic condition occurrence. The alarm history review flowchart 470 shows the alarm history is entered by pressing the ACT/activate button from the alarms menu screen 472. If no alarm history exists, a screen 474 indicating "NONE" can be displayed. However, if at least one alarm event has occurred, the entries can be displayed in a historical list 476. In one embodiment, the display shows a single glycemic alarm in the historical list at a time. The display shows a physiological characteristic value (e.g. blood glucose value) and time of the glycemic condition occurrence indicated for each alarm in the historical list. The time of the glycemic condition occurrence can also include a date of the alarm. Further, the display can show at least a portion of the time of the glycemic condition occurrence in blinking text. The historical list typically includes a limited number of stored entries. For example, the historical list can comprise the 20 most recent alarms indicating a glycemic condition occurrence. In alternative embodiments, the historical list may include more or less alarms, such as the 10, 15, 30, or 50 most recent alarms.

As part of the display of the historical list, the display can show the blood glucose measurements only within a specified range. For example, the specified range can be the operational range of the sensor, such as from 40 to 400 mg/dl, although the range may span other values, such as from 20 to 600 mg/dl. When a measurement in the historical list is above the specified range, the display shows a HI indicator. Similarly, the display shows a LO indicator for the measurements below the specified range.

C. Interrupted Sleep Alarm and Infusion Device Functions

Some alarm functions are designed to accommodate anticipated temporary behaviors of the users. For example, in the typical case where the characteristic value is a blood glucose level, it has been observed that when a user of the monitor is awakened from sleep by low blood glucose alarm from the monitor, there is often a period of disorientation. The disorientation may be particularly significant because the effect of low blood glucose level is made more severe at night. Consequently, in such a situation the user may begin pushing buttons on the device somewhat randomly in an attempt to quickly issue a bolus from the infusion device. This can result in an incorrect dosage or settings being altered without being realized by the user. In some embodiments of the invention, special functions can be invoked to alleviate the problems associate with this disorientation.

As mentioned previously, in a typical embodiment of the invention, the monitor may be included as part of an infusion device system. In such embodiments, the monitor and the infusion device may both be controlled through the same input device, e.g. keypad 112. In addition, information regarding both the monitor and infusion device may be displayed on the same display 114. Embodiments of the invention problem of night disorientation described above does not only involve a function of the monitor alarm. The function of the infusion device can also be modified.

Any of the functions described below to deal with night disorientation can be set in the monitor and/or infusion device to be invoked in different ways. For example, in one embodiment the user can activate a night mode upon retiring to bed (and deactivate it upon waking). One or more of the functions are activated while in the night mode. In another embodiment, one or more of the functions can be automatically set to operate during a specified period designed to correspond with the user's usual sleep. In any case, the function(s) may be divided into two related embodiments. A first embodiment delays accepting input from the user when an alarm wakes the user. A second embodiment provides an earlier warning to the user when sleeping than when awake. In addition, the two embodiments may also be combined.

A first embodiment of the invention as noted above operates to eliminate mis-operation of monitor and/or infusion device by requiring preventing input until disorientation of the user has abated somewhat. This may be done by an ordinary delay or, preferably by requiring a predetermined input before normal operation is restored. In one example embodiment of the first embodiment, when the night mode is activated and a low blood glucose alarm or shutoff has occurred, operation of the infusion device and/or monitor may be blocked until the user has provided the proper input. Blocking the device(s) operation may be performed by automatically invoking a "block" function that is built into the device (that is normally manually invoked by the user) or a simple keypad/button lockout. Alternately, a separate user "test" can be invoked such that the user must enter a specified key sequence (e.g. a numeric code) before operation of the device(s) is restored. Requiring such user input insures that any disorientation has passed before allowing operations such as delivering medication or altering other settings.

A typical example of this embodiment is a device comprising a sensor input capable of receiving a signal from a sensor, the signal being based on a sensed physiological characteristic value of a user of the device; and a processor coupled to the sensor input for operating an alarm based on the received signal from the sensor, wherein the processor activates the alarm according to a first criteria when the user is awake; and a second criteria when the user is asleep. Such devices are designed for example to adapt to a number of situations in which a user may exhibit different behaviors during time periods when they are typically asleep as compared to time periods when they are typically awake. For example, in the typical case where the characteristic value is a blood glucose level, it has been observed that when a user of the monitor is awakened from sleep by low blood glucose alarm from the monitor, there is often a period of disorientation. The disorientation may be particularly significant because the effect of low blood glucose level is made more severe at night.

In preferred embodiments of the invention, the sensed physiological characteristic is a measurement of glucose and the device provides an alarm warning at an earlier timepoint when the user is asleep as compared to when the user is awake by altering a threshold criteria for the activation an alarm during sleeping hours. Alternatively one can provide an alarm having a different tone or audibility. Exemplary threshold criteria include glucose concentrations reaching a predetermined value; or glucose concentrations exhibiting a predetermined rate of change. Optionally one can provide earlier or different alarm warnings to the user by using multiple alarms. For example the device can activate the alarm to provide earlier alarm warning by monitoring a rate of change in the sensed physiological characteristic value and adjusting an alarm threshold value when the rate exceeds a predetermined rate limit.

In the second embodiment, the likelihood night disorientation can be reduced by providing an earlier warning to the user regarding a low blood glucose level. In some embodiments, this may be characterized a purpose driven application of the multiple alarm function described above. Different alarm thresholds may be set to be active at different times. For example, a higher low blood glucose alarm threshold is set for sleeping hours than for waking hours. Alternately, the night alarm level (e.g. a higher low blood glucose alarm threshold)

can be manually activated upon retiring to sleep and cancelled upon waking as mentioned above. Multiple alarm thresholds (e.g. two levels of low blood glucose alarms) may also be applied within the night mode as well.

A typical example of this embodiment is a device comprising a sensor input capable of receiving a signal from a sensor, the signal being based on a sensed physiological characteristic value of a user; and a processor coupled to the sensor input for operating an alarm based on the sensed physiological characteristic value of the user from the received signal from the sensor; wherein the processor activates the alarm and delays accepting input from the user when the alarm awakens the user. In an illustrative embodiment of the invention, the physiological characteristic value is a blood glucose measurement and delaying accepting input from the user is applied to a low blood glucose alarm or a high blood glucose alarm. In preferred embodiments of the invention, the processor delays accepting input from the user until the user provides a predetermined input such as entering a numeric code or executing a button sequence. Optionally, delaying accepting input from a user who is most likely asleep when the alarm sounds is set according to a schedule based on a time of day, or alternatively, is set by the user before sleeping.

In further examples of the second embodiment, an early warning regarding a low blood glucose level to the user may be provided through a dynamic measurement, as described above. Employing a dynamic measurement (e.g. monitoring a rate change of the blood glucose level) enables the monitor to better anticipate a low blood glucose level. See section 3, above. In this case, a fast declining blood glucose rate, e.g. −2.0 mg/dL per minute or greater (which may be indicated by a single down arrow on the graphical display) will cause an adjustment in the low blood glucose alarm threshold value. For example, the fast declining blood glucose rate can trigger a low blood glucose threshold value to be raised by 6 mg/dL. Thus, the low blood glucose alarm will sound sooner than it otherwise would without the adjustment based on the fast declining blood glucose rate, allowing the user to wake up and make a correction with less chance of disorientation. Similarly, an even greater declining rate, e.g. a −4.0 mg/dL or greater (which may be indicated by a double down arrow on the graphical display) will cause a greater adjustment in the low blood glucose alarm threshold value. For example, this sharp declining blood glucose rate can trigger a blood glucose threshold value to be raised by 12 mg/dL, providing an even earlier warning than the first fast declining blood glucose rate. In the case of multiple alarms with different thresholds, the adjustment(s) may be applied to all of the low blood glucose alarms so that the same set of alarms operate but at adjusted levels.

As has been previously discussed in section 3, the dynamic measurement is can be applied to anticipate low (or high) blood glucose levels before they actually occur. This is useful whether the user is awake or asleep. In the case of an awakened user, however, it is important to provide somewhat more warning because of the possibility of disorientation as described above. Accordingly, a dynamic measurement and adjustment applied in a night mode may employ either a lower rate level or a greater threshold adjustment or both than that used in a normal (day) mode.

5. Advanced Blood Glucose Reminder Functions

Another aspect of the invention allows the user to set reminders that can be provided by the monitor. The reminders can be alarm signals (including, but not limited to, auditory, visual, tactile, etc.) that are initiated after a timer has run to prompt the user to take action or merely inform the user of a particular status. The reminder is started (i.e. the timer is initiated), when an event occurs and/or certain conditions are met. The alarm signals can be the same or different based upon the triggering events or conditions. These reminders can be used to further assist the user in managing insulin delivery for optimum results. For example, but not limited to, reminders can be set for event markers, blood glucose values, reference values, high or low sensor measurements.

Characteristic monitors and infusion devices can use event markers that place tags in the data for events the user experiences (e.g., but not limited to, meals, exercise, and high or low blood glucose). For example, but not limited to, when an infusion device identifies a high or low blood glucose event marker, it can start a timer that reminds the user to check blood glucose levels. This is intended to make therapy safer by encouraging more frequent checks during times that the patient may be at risk from hypoglycemia or hyperglycemia. In addition, this feature can also be applied to characteristic monitors. For example, but not limited to, a characteristic monitor that is used to show low or high blood glucose tags can have a timer set to remind a user to check their blood glucose levels at a later time.

In addition, a reminder timer can be set that is triggered if a blood glucose value is entered. For example, but not limited to, the reminder can be if the user enters a low or high blood glucose value into the monitor as a reference or calibration value.

A reminder timer can also be triggered by a user providing a reference value to the monitor. Thus, the user can be reminded to supply a new reference value after a minimum time period has elapsed. In this way calibration of the monitor is assured.

A blood glucose reminder can also be triggered by high or low measurement from the sensor. Thus, the monitor will request a blood glucose reference value during an excursion away from the normal range of values. The trigger for this reminder can be tempered by setting a minimum time between reminders to avoid pestering the user. This reminder can be used to provide more robust data for curve fitting as correlation improves with variability in the data pairs. The reminder promotes more frequent data collection during more critical periods (e.g., but not limited to, when blood glucose is too high or too low) and therefore the interpolated curve for this period is more reliably representative of the true curve.

One aspect behind the use of these reminders is that they also serve to prevent redundant and excessive alarms for the user. For example, if the timer is removed from the previously described high or low measurement reminder, the result would be a simple hypoglycemia or hyperglycemia alarm. Using a reminder, however, the message is not that the user's blood glucose is out of range. Rather, the reminder's message is to check the user's blood glucose with a meter, or the like. If a user's blood glucose is very near an alarm triggering threshold, an alarm might be triggered repeatedly as the value passes back and forth across the threshold. A reminder will set a timer, preventing duplicative warnings for a short period of time, but reminding the user to check blood glucose again when that period has expired. This can provide a better or easier path through the regulatory process. Thus, reminders are less likely to become a nuisance to the user and also prompt more useful data collection. In alternative embodiments, the alarm is triggered again, regardless of the presence of a time, if the glucose level continues to change in the direction of the trend.

Figure 5:
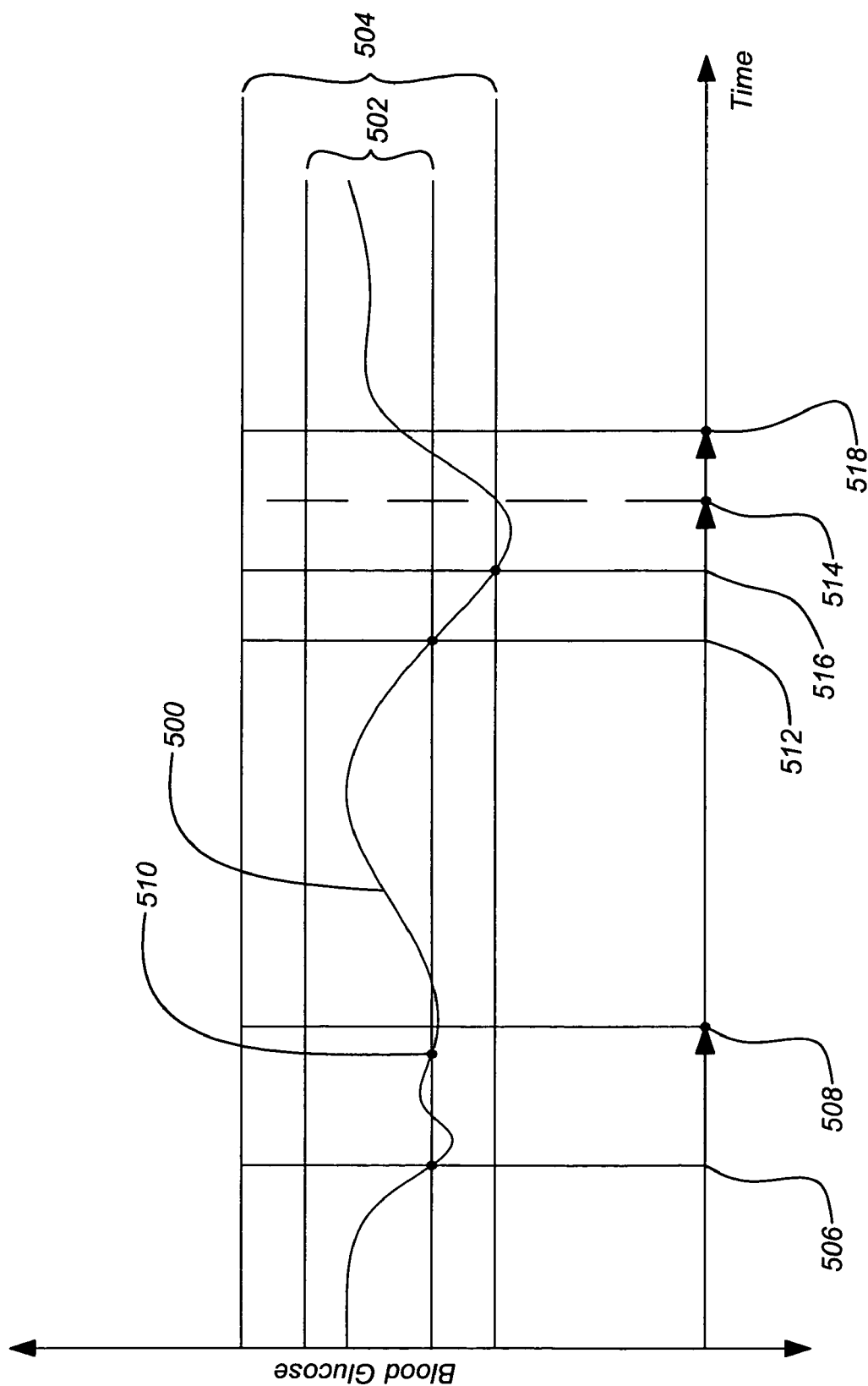
FIG. 5 illustrates a reminder function of an embodiment of the invention.

FIG. 5 illustrates a reminder function of the invention triggered by high or low characteristic values. A plot of a monitored characteristic value 500 (such as, but not limited to, blood glucose) is shown. One or more ranges 502, 504 define safe characteristic values (e.g., but not limited to, a first range 502 being a warning range and a second range 504 being a critical range), such as can be employed using multiple alarms as previously described. When a range is exceeded (e.g., but not limited to, at time 506), an alarm can be triggered but also a timer is started such that a reminder is also initiated after its expiration (e.g., but not limited to, at time 508). Over the timer period further occurrences of exceeding the threshold (e.g., but not limited to, at point 510) will not result in a duplicative alarm.

However, the situation can be somewhat different when the intervening triggering event is not identical to the first triggering event. For example, if a first range 502 is exceeded (e.g., but not limited to, at time 512) and a timer is started, but before a reminder can be issued (e.g., but not limited to, at time 514) a second range 504 is exceeded (e.g., but not limited to, at time 516), then the second alarm can be issued and the timer can be restarted. No reminder can be indicated at the theoretical expiration of the first timer (e.g., but not limited to, at time 514), but a reminder can be issued at the expiration of the second timer (e.g., but not limited to, at time 518). In this case, exceeding the second range overrides the first reminder because the second alarm is a different, albeit related, condition. As previously described, however, the use of reminders is not limited to monitoring high and low characteristic values. In a similar manner, reminders can be triggered by user's supplied reference values for calibration as well as event markers entered into the monitor.

6. Glucose Monitoring Information Management

Another aspect of the invention is to provide meaningful retrospective information to the patient using the sensor. In particular, a retrospective display of one or more physiological values can provide significantly useful data. As disclosed, the retrospective displays can be designed in a variety of ways to provide various useful information. For example, but not limited to, as the sleeping user receives no benefit from a real-time display, a retrospective view of data is important. While a simple listing of previous values has value, it can be time consuming to review, provides information that is difficult to visualize and comprehend and requires significant memory space within the device. Providing useful information that is easy to understand and that can be stored within a small memory space is very important. The ability to review data from the previous sleep period is particularly helpful to a user with nocturnal hypoglycemia or "dawn effect", as there is typically no witness to the real-time display. These measures can be even more important in cases where the alarm system can exhibit many false positives and/or false negatives, which might otherwise frustrate the user and lead to non-use of the monitor.

The following advanced data presentation tools can be used to conveniently and efficiently store and display useful information on a screen for a user to review while the monitor is in use. The tools provide useful information while requiring only a minimal amount of memory space. These data presentation tools can also be used in any retrospective analysis package, such as software running on a computer or network designed to analyze trends and provide advise regarding a treatment regime.

The tools operate by processing that compares actual reading to high and low value limits (e.g., but not limited to, acceptable blood glucose ranges). For example, but not limited to, the limits can be the adjustable hypoglycemic and hyperglycemic alarm thresholds of a monitor. Alternately, for standardization, the tools can be applied to a fixed definition of a target blood glucose range that is independent of the hyperglycemic and hypoglycemic alarm thresholds for the particular user/monitor.

Figure 6A:
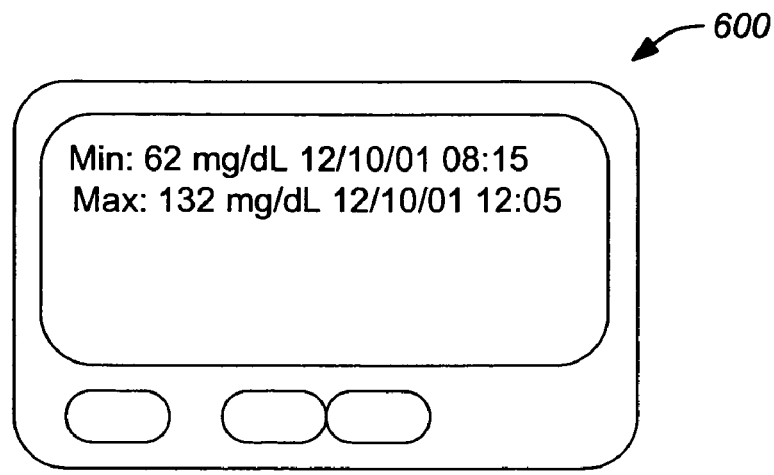
FIG. 6A illustrates minimum and maximum data presentation.
Figure 6B:
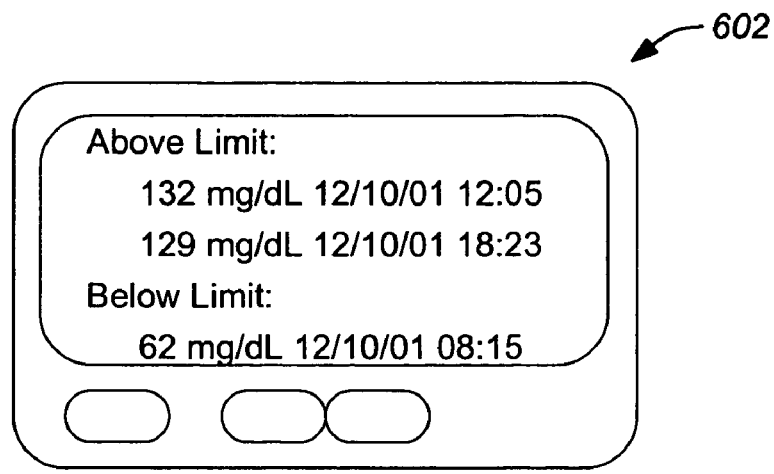
FIG. 6B illustrates excursion data presentation.

FIG. 6A illustrates one minimum and maximum data presentation. A display of the minimum and maximum values 600 of the characteristic monitor that have been measured for the user can be displayed on the monitor. The minimum value and maximum values can be conveniently displayed along with the date and time of their occurrence. Such a display 600 is useful, but becomes more useful when combined with an excursion count, a distribution of values, and/or integrated values as discussed below FIG. 6B illustrates an excursion data presentation. The number of excursions above or below the respective blood glucose limits is also very useful to have summarized for the user. An excursion display 602 provides good information, particularly when there are no alarms active on the monitor (either because the monitor is not turned on or alarms are not being employed by the user). A display 602 of the number of excursions above the hyperglycemic limit and the number of excursions below hypoglycemic limit give the user an idea of performance of a treatment program at a glance. A high number of incidents exceeding either limit indicate a need for improvements.

Figure 6C:
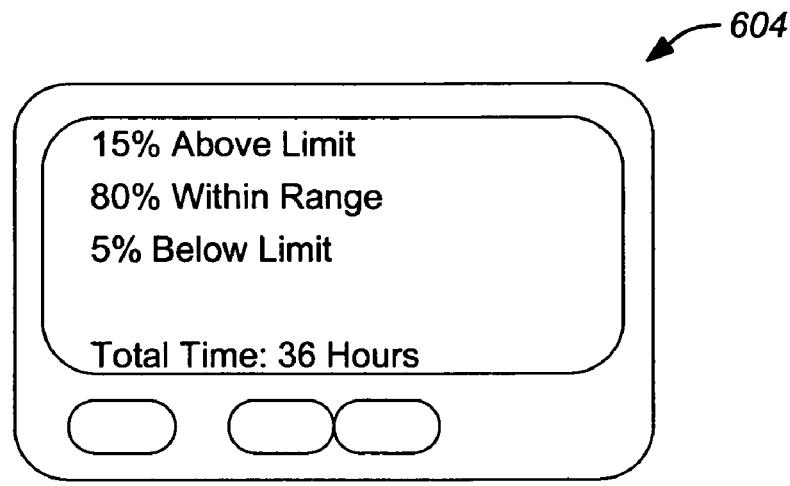
FIG. 6C illustrates characteristic value distribution data presentation.

FIG. 6C illustrates a characteristic value distribution data presentation. A simple distribution of sensor values offers a very powerful tool. In a preferred embodiment, the distribution is described in percentages that are automatically scaled with the duration of monitor use. Optionally, a monitor can include the total time of use with a percentage distribution. Awareness of a total time provides perspective for reviewing the percentage distribution. A time based distribution can also be used, but requires the total time to be included in the analysis as a reference. A distribution can also be presented based upon the total number of readings, but requires the total time is required in the analysis.

For example, but not limited to, the display can show a percentage of readings above a hyperglycemic alarm level, a percentage of readings below a hypoglycemic alarm level and a percentage of readings of readings within alarm range as shown in FIG. 6C. Optionally, the total time covered in the analysis can also be displayed. Similarly, an alternate display can show the time spent above a hyperglycemic alarm level, the time spent below a hypoglycemic alarm level and the time spent within alarm range (not shown). As mentioned, the time base display requires a known total time as part of the analysis. Finally, a display can also include the number of readings above hyperglycemic alarm level, the number of readings below a hypoglycemic alarm level and the number of readings within alarm range (not shown).

Figure 6D:
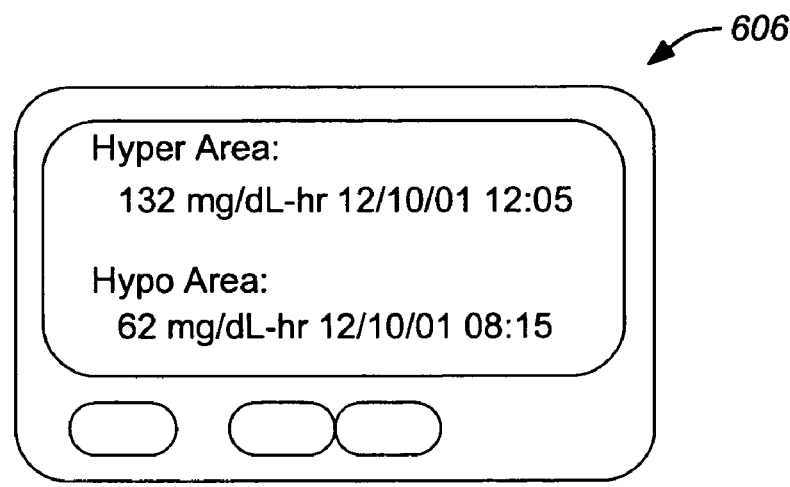
FIG. 6D illustrates integrated characteristic value data presentation.

FIG. 6D illustrates an integrated characteristic value data presentation. Performing an integration of the readings outside the alarm levels with respect to time can provide a measure of the hypoglycemic and hyperglycemic events' severity. In addition, these results can also be scaled these by a total sensor time to provide a measure that is duration independent.

For example, a "hyperglycemic area" can be calculated as the sum of the differences between the readings and the hyperglycemic alarm limit. A "hypoglycemic area" can be calculated from the sum of all the differences between the hypoglycemic alarm limit and the readings. A "hyperglycemic index" is calculated by taking the "hyperglycemic area" and dividing it by the duration of sensor use. Similarly, the "hypoglycemic index" can be calculated by taking the "hypoglycemic area" divided by the duration of sensor use.

Various alarms and/or monitoring aspects discussed above may be combined or utilized with other alarms and/or monitoring aspects. The possible embodiments and/or combinations should not be limited to the specific embodiments described above.

7. Real-Time Glucose Display and History

In other embodiments of the invention, a physiological characteristic monitor 104 is used for reviewing a history of measurements of the sensed characteristic value based on user input from an input device with a display for showing the history of the measurements of the sensed characteristic value. As discussed above with respect to the alarm history, the display may show the measurements only within a specified range, such as the operational range of the sensor (e.g. 40 to 400 or 20 to 600 mg/dl). Outside the specified range, a HI or LO indicator is shown.

Figure 7:
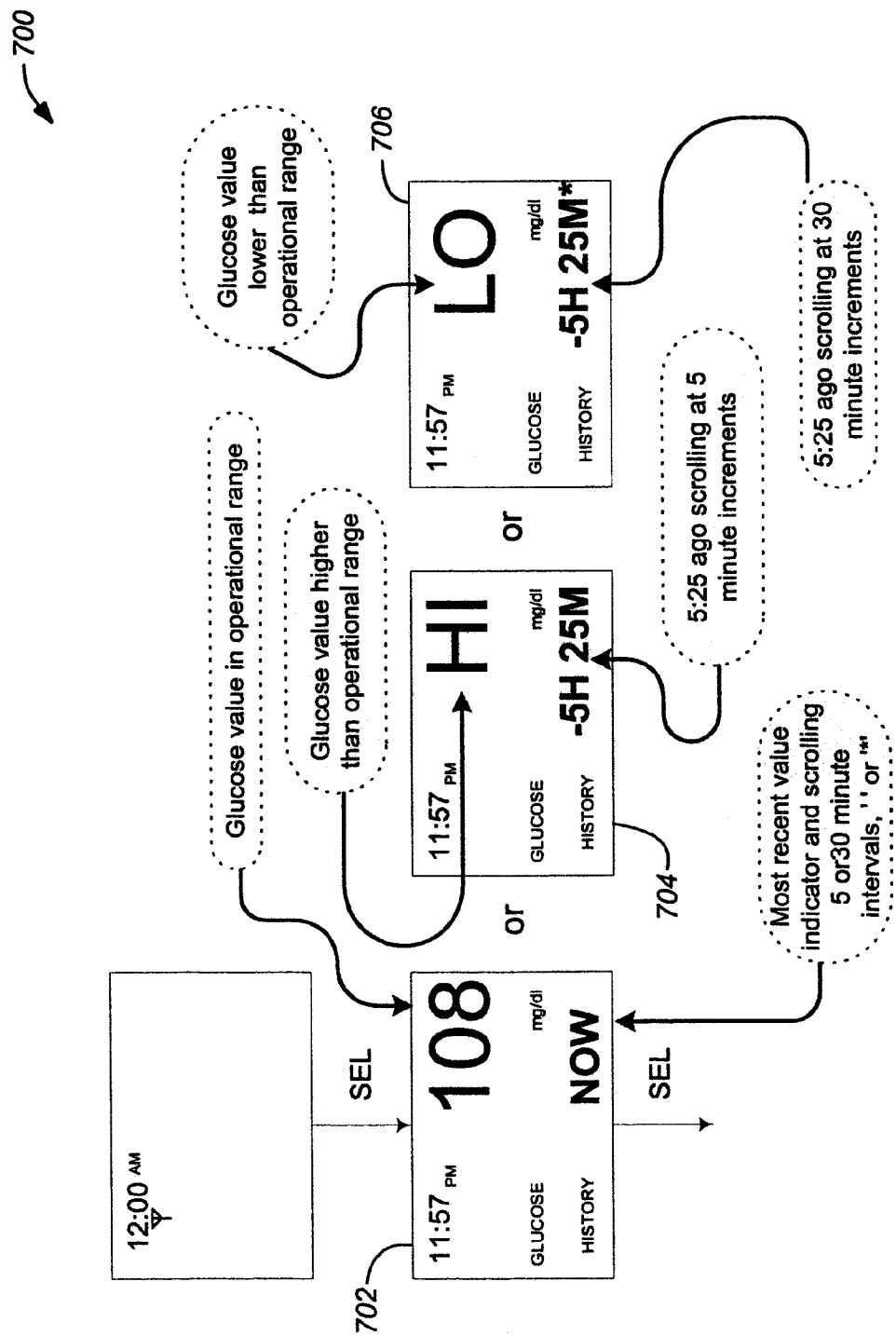
FIG. 7 illustrates screens for viewing real-time and historical measurements of a physiological characteristic value in an embodiment of the invention.

FIG. 7 illustrates the real-time and history display 700 of an embodiment of the invention. Three exemplary screens 702, 704, 706 are shown for the display of real-time or historical measurement data. The in-range screen 702 is used when the measurement is within the specified range; the actual measurement is shown. The high screen 704 (showing a HI indicator) is used when the measurement is above the specified range, and the low screen 706 (showing a LO indicator) is used when the measurement is below the specified range. The display shows a no measurement indicator where no value was recorded in the history.

The user input also directs scrolling through a history of the measurements of the sensed characteristic value. In a typical embodiment, the display shows a single measurement at a time. The display shows a time of acquisition by the sensor for each measurement in the history. In the example in-range screen 702, the current measurement is being shown, indicated by the "NOW" indicator. The time of acquisition can be shown as a value relative to a most recent measurement of the history. For example, the high and low screens 704, 706 each show values measured 5 hours and 25 minutes before the current time interval. Alternatively, the actual date and time of the measurement may be shown.

The history of the measurements of the sensed characteristic value can be scrolled through in even time increments. In further embodiments, the even time increment can have a selectable size (e.g. selectable between 5 minute or 30 minute increments), and the selected time increment can be indicated on the display as the history is reviewed. The history itself can comprise a fixed total period from the present backward. For convenience, scrolling through the history wraps around after an end of the history is reached.

In further embodiments of the invention, when no measurement is currently available, the NOW indicator can be replaced by a status message indicating no calibration, noise or a missed measurement.

8. Graphical Display of Measurements of Characteristic Values

In further embodiments of the invention, a graphical display is employed in the monitor 104 (which may be combined with an infusion device) to allow for a user to readily apprehend the current and historical measurements of the characteristic value tracked by the monitor 104.

Embodiments of the invention include devices which display data from measurements of a sensed physiological characteristic (e.g. blood glucose concentrations) in a manner and format tailored to allow a user of the device to easily monitor and, if necessary, modulate the physiological status of that characteristic (e.g. modulation of blood glucose concentrations via insulin administration). One illustrative embodiment is a device comprising a sensor input capable of receiving a signal from a sensor, the signal being based on a sensed physiological characteristic value of a user; a memory for storing a plurality of measurements of the sensed physiological characteristic value of the user from the received signal from the sensor; and a display for presenting a text and/or graphical representation of the plurality of measurements of the sensed physiological characteristic value (e.g. text, a line graph or the like, a bar graph or the like, a grid pattern or the like or a combination thereof). Preferably, the graphical representation displays real time measurements of the sensed physiological characteristic value. Such devices can be used in a variety of contexts, for example in combination with other medical apparati. In preferred embodiments of the invention, the device is used in combination with at least one other medical device (e.g. a glucose sensor) and receives a signal from this device that is transmitted via a wired or wireless connection. Wireless communication can include for example the reception of emitted radiation signals as occurs with the transmission of signals via RF telemetry, infrared transmissions, optical transmission, sonic and ultrasonic transmissions and the like. Most preferably, the device is an integral part of a medication infusion pump (e.g. an insulin pump). Typically in such devices, the physiological characteristic values includes a plurality of measurements of blood glucose.

In typical embodiments of the invention, the physiological characteristic value measurement is displayed in a graphical format, a text format or a combination thereof. For example, the graphical representation can comprise a color coded set of one or more indicators of the status of the physiological characteristic. In a specific embodiment, the graphical representation comprises one or more trend indicators, indicating an approximate rate trend in the sensed physiological characteristic value over a recent series of the plurality of measurements (e.g. the four most recent measurements of the sensed physiological characteristic value). Optionally the graphical representation further comprises a vertical cursor which allows a user to alternatively select measurements of a sensed physiological characteristic value from the graphical format or from a text format. For example, the display can include a scrolling vertical cursor, allowing individual Blood Glucose measurements in the graphics plot to be selected, with the Blood Glucose value and the time the measurement was made displayed in a text portion of the screen.

The display for presenting a graphical representation of the plurality of measurements of the sensed physiological characteristic value can comprise a number of different formats in which to display the various physiological characteristic values. For example, in embodiments of the invention where the graphical representation comprises one or more trend indicators, the trend indicators can include an indicator of a past measurement, a current measurement or a combination thereof. Preferably embodiments include a continuous screen update, with the graphics display updated upon receipt of each telemetered blood glucose value. In certain formats, the trend indicators comprise a color coded set of indicators. The graphical display can be modulated to indicate to the user whether it is day or night. For example, when the time range shows the 24 hour period the graphical plot daytime hours can be displayed with a light background and night time hours can displayed with a dark background. In embodiments where the time range shows the 24 hour period, noon and midnight on the graphical plot can each be marked by a vertical line. In such a 24 hour graph, optionally night is indicated by reverse graph (e.g. white dots on black background).

In a specific illustrative embodiment of the invention, the physiological characteristic value can be a blood glucose measurement and the color coded set of indicators can comprise a grid of nine indicators including three rate trend categories including going down, stable and going up and three current measurement categories including low, in zone and high where a single rate trend category and a single current measurement category are indicated simultaneously. Optionally in such embodiments, going down and low and going up and high can be indicated in red; going down and high and going up and low can be indicated in yellow; going down and in zone, going up and in zone, stable and high and stable and low can be indicated in orange; and stable and in zone can be indicated in green.

In yet another illustrative embodiment of the invention, the physiological characteristic value is a blood glucose measurement and the graphical representation comprises a graphical plot of at least a portion of the plurality of measurements of the sensed blood glucose measurement where a horizontal axis comprises a time scale and a vertical axis comprises a blood glucose measurement scale. Optionally, the graphical plot can comprise a color coded set of indicators. For example, a color coded set of indicators can comprise horizontal bands corresponding to various levels of danger (e.g. hyperglycemia or hypoglycemia) corresponding to each of the plurality of measurements of the sensed blood glucose measurement. Optionally, the color coded set of indicators can comprise a color of the graphical plot indicating a current danger level corresponding to a current blood glucose measurement. In certain embodiments of the invention, the graphical plot can be continuously updated in real-time such that the shown portion of the plurality of measurements of the sensed blood glucose measurement comprises a most recent period.

In other embodiments where a graphical representation comprises one or more trend indicators, the trend indicators can comprise about five symbols indicating for example a fast increasing rate, a moderate increasing rate, a negligible rate change, a moderate decreasing rate and/or a fast decreasing rate, respectively. The symbols can comprise any one of a variety of suitable symbols, for example arrows, with two up arrows, a single up arrow, no indicator, a single down arrow and two down arrows, corresponding respectively to for example, the fast increasing rate, the moderate increasing rate, the negligible rate change, the moderate decreasing rate and the fast decreasing rate. In one such embodiment of the invention, the physiological characteristic value is a blood glucose measurement and the fast increasing rate is at least approximately +3 mg/dl, the moderate increasing rate is between approximately +3 mg/dl and +1 mg/dl, the negligible rate change is between approximately +1 mg/dl and −1 mg/dl, the moderate decreasing rate is between approximately −1 mg/dl and −3 mg/dl and the fast decreasing rate equal or exceeding −3 mg/dl. In an illustrative embodiment, trend indicators indicate the average glucose rate of change over the last 4 measurements: Double up arrow for an average increase equal to or greater than 3 mg/dl. Single up arrow for an average increase less than 3 and equal to greater than 1 mg/dl. No arrow for an average increase or decrease less then 1 mg/dL. Single down arrow for an average decrease less than 3 and equal to greater than 1 mg/dl. Double down arrow for an average decrease equal to or greater than 3 mg/dl.

In typical embodiments of the invention, the display is tailored to a specific set of criteria that are associated with an analyte to be sensed. For example, in a display tailored to provide information on blood glucose, the blood glucose measurement scale can be selectively displayed in mg/dl or mmol/l. In the context of the analyte itself for example, the blood glucose measurement scale can comprise a fixed measurement range from approximately 0 to 310 mg/dl or approximately 0 to 17.2 mmol/l. In addition, the time scale can comprise a time range selectively changed to show different periods of a plurality of blood glucose measurements. In an illustrative example, the time range is selectively changed as either a 3 hour period or a 24 hour period. Optionally, the time range shows the 3 hour period the graphical plot comprises approximately 36 blood glucose measurements, each approximately five minutes apart. In certain embodiments of the invention, when the time range shows the 3 hour period each hour of the graphical plot is marked by a vertical line. In a specific embodiment, when the time range shows the 24 hour period the graphical plot comprises approximately 72 blood glucose measurements, each approximately 20 minutes apart.

9. Illustrative Specific Embodiment of the Invention

The invention disclosed herein has a number of specific embodiments. The following describes a specific preferred embodiment of the invention comprising a insulin infusion device having an monitor that provides a display of physiological glucose values and a user interface.

In this specific embodiment, software associated with the device can allow the entry of a number of user values such as a "Sensor ON/OFF" function that allows the user to turn the sensor on or off. When the sensor is turned ON, features such as those described below can be enabled. When the Sensor is turned off, the options will not be displayed in the pump menus. Options include a Sensor Transmitter ID Number which allows the user to enter the ID number of the sensor transmitter. Another option is a Low Glucose Level which allows the user to select the Low Glucose Alarm Level. This parameter can have a minimum of 50 mg/dl. It can have a maximum equal to 10 mg/dl below the High Glucose Level set by the User. The default can be 50 mg/ml. It can provide a visual feedback of the new selection. Another option is a Low Glucose Snooze which can define the time period between the first Low Glucose Alarm and any subsequent Low Glucose alarm. It can have a minimum of 5 minutes and a maximum of 60 minutes. The default can be 20 minutes. Another option is a Low Glucose Suspend which allows allow the user to select the Low Glucose Suspend Level. The default can be Off. If turned On, this parameter can have a minimum of 40 mg/dl. It can have a maximum equal to 10 mg/dl below the Low Glucose Level set by the User (see previous paragraph), up to 120 mg/ml. Once turned on, the default can be 40 mg/ml. It can provide a visual feedback of the new selection. Another option is a High Glucose Level which allows allow the user to select the High Glucose Alarm Level. The default can be Off. If turned On, this parameter can have a minimum equal to 10 mg/dl above the Low Glucose Level set by the User (see previous two paragraphs). It can have a maximum of 400 mg/dl. Once turned on, the default can be 200 mg/ml. It can provide a visual feedback of the new selection. Another option is a High Glucose Snooze which can define the time period between the first High Glucose Alarm and any subsequent High Glucose alarm. It can have a minimum of 5 minutes and a maximum of 180 minutes. The default can be 60 minutes. Another option is a Glucose Format which can allow the user to select glucose values to be displayed in units of mg/dl or mmol/l. The default can be mg/dl. It can provide a visual feedback of the new selection. Another option is a Communication Failure Alert Period (Missed Data) which can allow the user to set the time period that will lapse between the loss of communications and a loss of communications alarm. This parameter can have a minimum value of 5 minutes and a maximum value of 40 minutes. After 40 minutes, the pump can re-sync automatically. If the re-sync fails, a Link Error alarm is generated and the communication stops. The default can be 30 minutes. Another option is a Calibration Reminder, a value which can define the time before the sensor Calibration is required to remind the user. The minimum value can be Off. The Maximum value can be 4 hours. The default value can be 1 hour.

In this preferred embodiment, the following sensor trend values can be utilized in the glucose calculations. A first sensor trend value is a High Positive Trend Threshold which can define the High Positive Trend Threshold limit that will result in a display of two up arrows. The value can be 3 mg/dl per minute averaged over 20 minutes. This can be defined as a change between the current glucose value and the 20-minute-old glucose value. Another sensor trend value is a Low Positive Trend Threshold which can define the Low Positive Trend Threshold limit that will result in a display of one up arrow. The value can be 1 mg/dl per minute. Another sensor trend value is a Low Negative Trend Threshold which can define the Low Negative Trend Threshold limit that will result in a display of one down arrow. The value can be −1 mg/dl per minute. Another sensor trend value is a High Negative Trend Threshold which can define the High Negative Trend Threshold limit that will result in a display of two down arrows. The value can be −3 mg/dl per minute. Another sensor trend value is a Glucose Calibration/Calculation which can calibrate the glucose value using the raw data from the sensor. Optionally a mathematical formula or algorithm is used in this calculation. For example, the glucose can be calculated by multiplying the glucose raw data value by the calibration factor.

This preferred embodiment of the invention includes a Glucose Graphical History Screen which can be activated by pushing the ESC key, and can stay active for some period of time (e.g. 2 minutes) before transitioning to the default "Idle" screen. This can display information including the current glucose level as measured by the Sensor, displayed in units selected by the user. These can be displayed graphically in 5-minute intervals, with each data point 2 pixels wide. The most recent data can be on the right side of the display. An alphanumeric display of the glucose data or reasons that the data is not displayed can be included. The current value of High Glucose Level set by the user can be displayed as a dashed line on the graph. The current value of Low Glucose Level set by the user can be displayed as a dashed line on the graph. Glucose Trend Indicator: High or Low Glucose Trend can be displayed as a single or double up arrow while the user is viewing the Current Glucose Value.

The device can compare the trend magnitude received from the sensor with a trend threshold value and display arrows on the screen based on the following rules: if the trend information is greater than or equal to the High Positive Trend Threshold, the screen can display two arrows pointing up; if the trend magnitude is less than the High Positive Trend Threshold and greater than or equal to the Low Positive Trend Threshold, the screen can display one arrow pointing up; if the trend magnitude is less than the Low Positive Trend Threshold and greater than or equal to the Low Negative Trend Threshold, the screen can display no arrows; if the trend magnitude is less than the Low Negative Trend Threshold and greater than or equal to the High Negative Trend Threshold, the screen can display one arrow pointing down; if the trend information from the sensor is less than the High Negative Trend Threshold, the screen can display two arrows pointing down.

The screen can display the time of the sensor value measurement, for example in the form of time markers. There can be a vertical dashed line at each clock hour on the 3-hour display. There can be a vertical dashed line at Noon and Midnight on the 24-hour display. The graphic screen can display a visual indication of data above and below the range of the display screen. The terms "HIGH" and "LOW" can be displayed in the alphanumeric display. The graphic screen can visually display the time of any boluses within the time displayed on the graph. This can be done with a bar at the bottom of the screen.

The screen can include a cursor. Consequently, the user can scroll a vertical cursor left and right through the points on the graph, and the time, and the glucose value for each data point can be displayed. This can be done using the up and down buttons. When displaying data that is not the current value, the screen can have a different appearance to alert the user that the data is historical, not current. This may be done by flashing the numbers or using an inverse font. It can also display the term "History". The user can be able to change the screen from a 3 hour width to a 24 hour width by pushing a single button. In this mode, the screen can display 24 hours of data at 20-minute intervals. In this display, each time period can be only one pixel wide. The display can incorporate features to identify to the user that this is a 24-hour display, not the three-hour display. This may be done by putting the night hours (6 pm to 6 am) in inverse font, placing the terms "3 hour" or "24 hour" on the display, both, or another method. There can be a vertical line at Noon and Midnight.

The device can further include a calibration glucose entry which allows the user to enter the reference glucose values from an external meter reading. The frequency of this entry can be based on the sensor calibration requirements. The User can get a reminder at a user selectable time period prior to the required entry time. The measurement can be entered manually or can be communicated to the device via a wired or wireless connection. Wireless communication can include for example the reception of emitted radiation signals as occurs with the transmission of signals via RF telemetry, infrared transmissions, optical transmission, sonic and ultrasonic transmissions and the like. When the Paradigm™ Link meter is used, the glucose measurement is sent to the pump automatically via RF. Alternatively, one can use an embodiment of the invention disclosed herein in combination with any one of the wide variety of other medical devices known in the art such as those produced by Therasense, Roche, Bayer or Abbot laboratories.

The device can have a number of alarm functions. When an alarm condition occurs, the pump can display the alarm to the user on the pump screen and via the selected alert mechanism. The pump can provide the ability to clear the display and return to the action previously in progress. A cleared sensor or glucose alarm can not be reissued for a user specified time after the user clears the alarm. Alarm conditions include a communications error alarm where the alarm can be set when the pump doesn't receive valid data for the time period specified by the use, a sensor low battery alarm which can activate when the sensor transmitter sends a low battery signal, a sensor dead battery alarm which can activate when the sensor transmitter sends a dead battery signal, a low glucose alarm which can be set when the current glucose level is equal to or below the low glucose level set by the user, and a shutoff limit alarm which can be set when the current glucose level is equal to or below the shutoff limit level set by the user and which can suspend pumping and warn the user following the alarm protocol. The error message can be similar to "low glucose—pumping suspended", a high glucose alarm which can be set when the current glucose level is equal to or above the high glucose level set by the user, a calibration required alarm which can be set when 12 hours have elapsed since the last reference glucose value has been entered (this time period can be determined based on the sensor calibration requirements), a sensor end of life alarm which can be set when the pump calculates that the sensor has reached its end of life, a calibration needed alarm which can inform the user a calibration is needed in short period of time. The user can set the time delay between this alarm and the calibration required alarm. The device also includes a glucose alarm history where the pump can display the sensor glucose alarm values as a tabular display of time and alarm information, with the ability to scroll forward and backward in time. This function can be combined with other history tables.

The Pump can also display the user entered glucose calibration values as a tabular display of time and alarm information, with the ability to scroll forward and backward in time. This can include user entered values as well as the values sent automatically via RF. The device sending the value can be a device such as a Paradigm link meter or any one of the wide variety of other appropriate medical devices known in the art such as those produced by Therasense, Roche, Bayer or Abbot laboratories. This function may be combined with other history tables. The pump can allow the user to conveniently access sensor information and settings. The sensor status screen can include the following information: communication status; next calibration; sensor age; sensor isig value; transmitter battery status; transmitter software version; transmitter serial number; and pump serial number. The sensor settings screen can include the following information: sensor is on or off; high glucose setting; high glucose snooze time; low glucose setting; low glucose snooze time; low glucose shutoff limit; alarm snooze; calibration required reminder time; BG units selection; and transmitter serial number.

The pump can store the most recent 3 days of sensor raw data, and computed glucose values of the last 30 days. The pump can support the download of either the complete database of memory or selected block specific sections of data via the comlink or meter. The download time can be minimized with a goal that it can not exceed two (2) minutes for the sensor data. The pump can download either its complete database of memory or selected block specific sections of memory via the comlink or meter. The download time can be minimized with a goal that it can not exceed four (4) minutes for the pump. The pump can communicate using telemetry.

This concludes the description including the preferred embodiments of the present invention. The foregoing description including the preferred embodiment of the invention has been presented for the purposes of illustration and description. It is not intended to be exhaustive or to limit the invention to the precise form disclosed. Many equivalent modifications and variations are possible in light of the above teaching.

It is intended that the scope of the invention be limited not by this detailed description, but rather by the claims appended hereto. The above specification, examples and information provide a description of the manufacture and use of the apparatus and method of the invention. Since many embodiments of the invention can be made without departing from the scope of the invention, the invention resides in the claims hereinafter appended. Throughout this application, various publications are referenced. The disclosures of these publications are hereby incorporated by reference herein in their entireties.

What is claimed is:

1. A device, comprising:
a sensor input capable of receiving a signal from a sensor, the signal being based on a sensed physiological characteristic value of a user of the device, wherein the sensed physiological chatacteristic is a measurement of glucose; and
a processor coupled to the sensor input for operating an alarm based on the received signal from the sensor;
wherein the processor activates the alarm according to:
a first criteria when the user is awake; and
a second criteria when the user is asleep.

2. The device of claim 1, wherein the device provides an alarm warning at an earlier timepoint when the user is asleep as compared to when the user is awake by altering a threshold criteria for the activation an alarm during sleeping hours, wherein the threshold criteria includes:
glucose concentrations reaching a predetermined value; or
glucose concentrations exhibiting a predetermined rate of change.

3. The device of claim 2, wherein providing earlier alarm warning to the user is applied to multiple alarms.

4. The device of claim 2, wherein activating the alarm to provide earlier alarm warning is performed by monitoring a rate of change in the sensed physiological characteristic value and adjusting an alarm threshold value when the rare exceeds a predetermined rate limit.

5. The device of claim 4, wherein the physiological characteristic value is a blood glucose measurement, providing earlier warning to the user is applied to a low blood glucose alarm and the rate limit comprises a. declining blood glucose rate.

6. The device of claim 5, wherein the rate limit is between approximately −2.0 mg/dl and approximately −4.0 mg/dl.

7. The device of claim 2, wherein adjusting the alarm threshold criteria comprises raising a low blood glucose alarm threshold.

8. The device of claim 7, wherein the low blood glucose alarm threshold is raised by approximately 6 mg/dl.

9. The device of claim 7, wherein the low blood glucose alarm threshold is raised by approximately 12 mg/dl.

10. The device of claim 7, wherein the low blood glucose alarm threshold is raised by approximately 6 mg/dl and the rate limit is approximately −2.0 mg/dl.

11. The device of claim 7, wherein the low blood glucose alarm threshold is raised by approximately 12 mg/dl the rate limit is approximately −4.0 mg/dl.

12. The device of claim 2, wherein activating the alarm to provide earlier warning is set according to a schedule based on a time of day.

13. The device of claim 2, wherein activating the alarm to provide earlier warning is set by the user before sleeping.

14. The device of claim 1, wherein the processor delays accepting input from the user when the processor activates the alarm according to the second criteria.

15. A device, comprising:
a sensor input capable of receiving a signal from a sensor, the signal being based on a sensed physiological characteristic value of a user; and
a processor coupled to the sensor input for operating an alarm based on the sensed physiological characteristic value of the user from the received signal from the sensor;
wherein the processor activates the alarm and delays accepting input from the user when the alarm awakens the user.

16. The device of claim 15, wherein the physiological characteristic value is a blood glucose measurement and delaying accepting input from the user is applied to a low blood glucose alarm.

17. The device of claim 15, wherein the physiological characteristic value is a blood glucose measurement and delaying accepting input from the user is applied to a high blood glucose alarm.

18. The device of claim 15, wherein delaying accepting input from the user is applied to a plurality of alarm based on a plurality of sensed physiological characteristic values.

19. The device of claim 15, wherein delaying accepting input from the user is set according to a schedule based on a time of day.

20. The device of claim 15, wherein delaying accepting input from the user is set by the user before sleeping.

21. The device of claim 15, wherein the processor delays accepting input from the user until the user provides a predetermined input.

22. The device of claim 21, wherein the predetermined input comprises entering a numeric code or executing a button sequence.

23. The device of claim 15, wherein the processor activates the alarm to provide earlier warning to the user when sleeping than when the users is awake.

24. A device, comprising:
a sensor input capable of receiving at least one signal from a sensor, the signal being based on a plurality of sensed physiological characteristic values of a user of the device; and
a processor coupled to the sensor input for operating a plurality of alarms based on the received signal from the sensor, wherein;
the processor is capable of activating each of the plurality of alarms according to a different sensed physiological characteristic value of the plurality of sensed physiological characteristic values;
the plurality of sensed physiological characteristic values include:
blood glucose concentrations in the user; and
the rate of change of blood glucose concentrations in the user over a predetermined time period;
a first alarm is activated when glucose concentrations exhibit a predetermined rate of change and a second alarm is activated when glucose concentrations reach a predetermined value; and
the criteria for activating the first alarm are more stringent than the criteria for activating the second alarm.

25. The device of claim 24, wherein the processor is capable of activating one of the plurality of alarms based on an evaluation of both the blood glucose concentrations in the user and the rate of change of blood glucose concentrations.

26. The device of claim 25, wherein the alarm is activated based on a mathematical comparison of the blood glucose concentrations in the user and the rate of change of blood glucose concentrations in the user.

27. The device of claim 24, further including a relay that automatically dials a predetermined telephone number as part of a notification scheme for an event that has not been acknowledged and/or addressed by the user.

* * * * *

UNITED STATES PATENT AND TRADEMARK OFFICE
CERTIFICATE OF CORRECTION

| | | |
|---|---|---|
| PATENT NO. | : 7,399,277 B2 | Page 1 of 1 |
| APPLICATION NO. | : 10/860114 | |
| DATED | : July 15, 2008 | |
| INVENTOR(S) | : Saidara et al. | |

It is certified that error appears in the above-identified patent and that said Letters Patent is hereby corrected as shown below:

<u>Column 40</u>:

Claim 4, line 18, please delete "rare" and insert --rate--; and

<u>Column 41</u>:

Claim 18, line 2, please delete "alarm" and insert --alarms--.

Signed and Sealed this

Sixteenth Day of November, 2010

David J. Kappos
*Director of the United States Patent and Trademark Office*